(12) United States Patent
Monia et al.

(10) Patent No.: US 7,919,472 B2
(45) Date of Patent: Apr. 5, 2011

(54) ENHANCED ANTISENSE OLIGONUCLEOTIDES

(75) Inventors: Brett P. Monia, Encinitas, CA (US); Andrew M. Siwkowski, Carlsbad, CA (US); Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 263 days.

(21) Appl. No.: 11/231,243

(22) Filed: Sep. 19, 2005

(65) Prior Publication Data

US 2006/0063730 A1 Mar. 23, 2006

Related U.S. Application Data

(66) Substitute for application No. 60/611,100, filed on Sep. 17, 2004.

(60) Provisional application No. 60/663,442, filed on Mar. 18, 2005, provisional application No. 60/718,685, filed on Sep. 19, 2005, provisional application No. 60/718,684, filed on Sep. 19, 2005.

(51) Int. Cl.
*A01N 43/04* (2006.01)
*C12Q 1/68* (2006.01)
*C12N 15/63* (2006.01)
*C07H 21/02* (2006.01)
*C07H 21/04* (2006.01)

(52) U.S. Cl. ......... 514/44; 435/6; 435/91.1; 435/91.31; 435/455; 536/23.1; 536/24.31; 536/24.5

(58) Field of Classification Search ............. 435/6, 91.1, 435/91.31, 455; 514/44; 536/23.1, 24.5, 536/24.31
See application file for complete search history.

(56) References Cited

U.S. PATENT DOCUMENTS

| | | | |
|---|---|---|---|
| 5,801,154 A | | 9/1998 | Baracchini et al. |
| 5,872,242 A | | 2/1999 | Monia et al. |
| 5,985,558 A | | 11/1999 | Dean et al. |
| 6,133,246 A | * | 10/2000 | McKay et al. ............. 514/44 |
| 6,228,642 B1 | * | 5/2001 | Baker et al. ............. 435/375 |
| 6,248,724 B1 | | 6/2001 | Moore et al. |
| 2001/0016575 A1 | | 8/2001 | Miraglia et al. |
| 2002/0004490 A1 | * | 1/2002 | Dean et al. ................. 514/44 |
| 2003/0022848 A1 | | 1/2003 | Baker et al. |
| 2003/0203862 A1 | | 10/2003 | Miraglia et al. |
| 2005/0014257 A1 | | 1/2005 | Crooke et al. |
| 2005/0026192 A1 | * | 2/2005 | Moore et al. ............. 435/6 |
| 2005/0043524 A1 | | 2/2005 | Bhanot et al. |
| 2005/0053981 A1 | | 3/2005 | Swayze et al. |
| 2005/0074801 A1 | | 4/2005 | Monia et al. |
| 2005/0142581 A1 | | 6/2005 | Griffey et al. |

FOREIGN PATENT DOCUMENTS

| WO | WO 00/49937 A2 | 8/2000 |
|---|---|---|
| WO | WO 2005/005599 A2 | 1/2005 |
| WO | WO/2005/023825 | 3/2005 |
| WO | WO 2005/023986 A2 | 3/2005 |
| WO | WO 2005/023995 A2 | 3/2005 |

* cited by examiner

*Primary Examiner* — Jane Zara
(74) *Attorney, Agent, or Firm* — Jones Day

(57) ABSTRACT

Described herein are gap-widened antisense oligonucleotides having improved therapeutic index as compared to 5-10-5 MOE gapmer antisense oligonucleotides of the same sequence. Also described are methods of reducing a target RNA in an animal using the gap-widened antisense oligonucleotides of the present invention. Further, are methods for selecting a gap-widened antisense oligonucleotides.

20 Claims, 6 Drawing Sheets

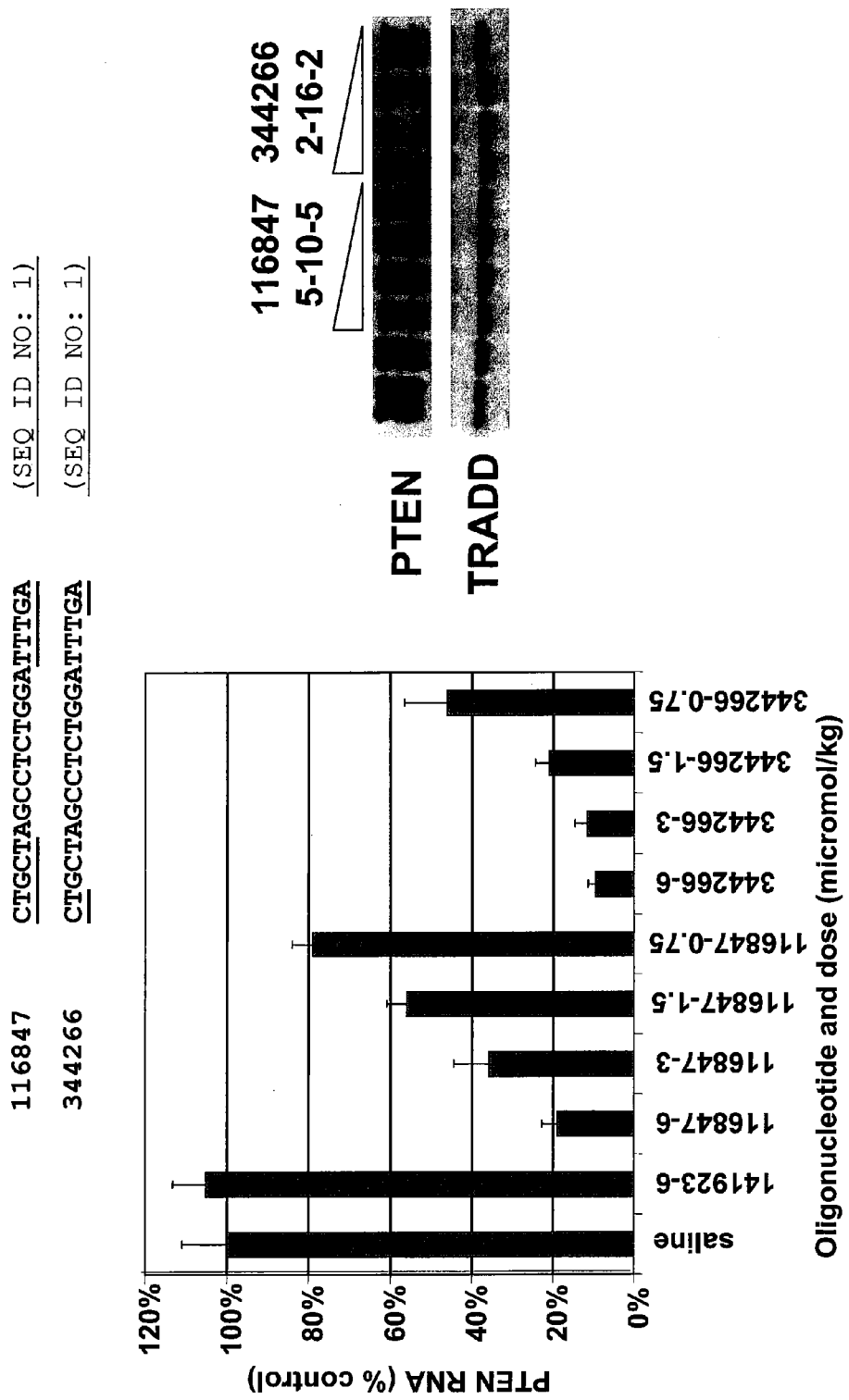

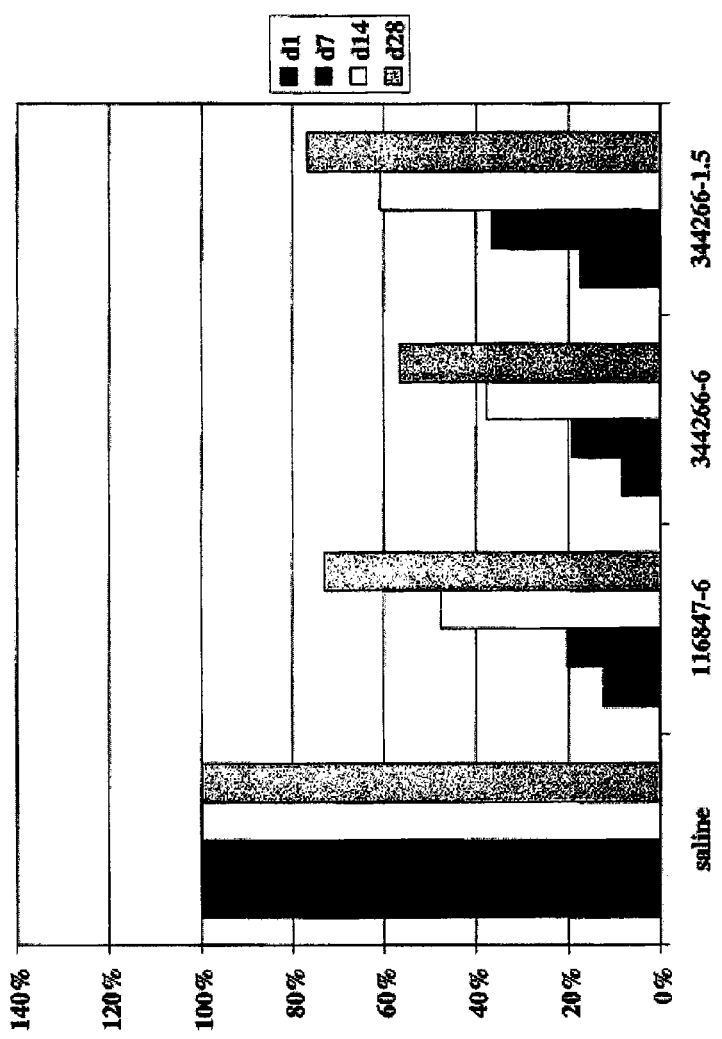
Figure 2: 344266 supports similar persistence of action compared to 116847

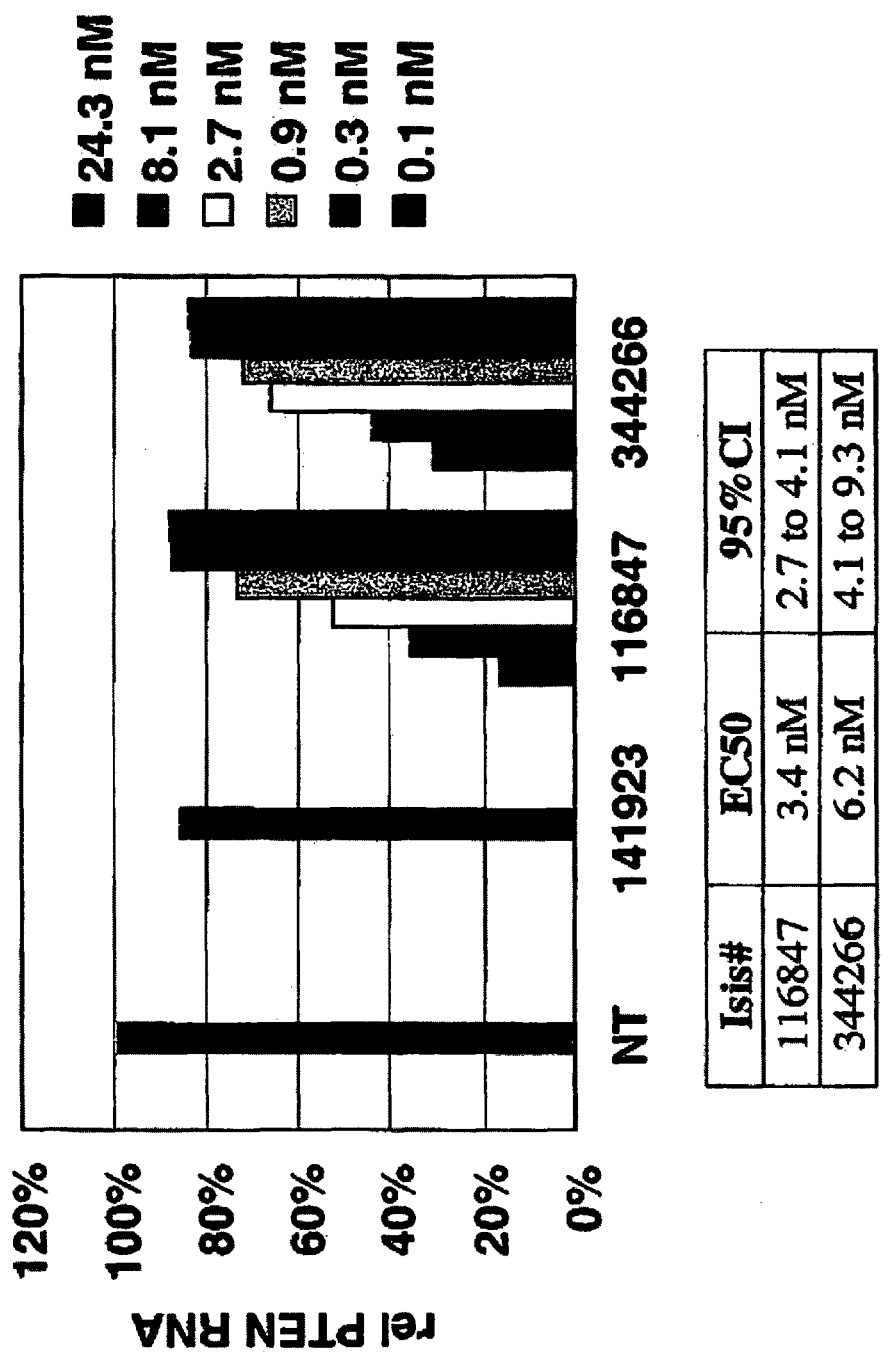
Figure 3: In vitro comparison of 5-10-5 and 2-16-2 versions of 116847 in bEND cells

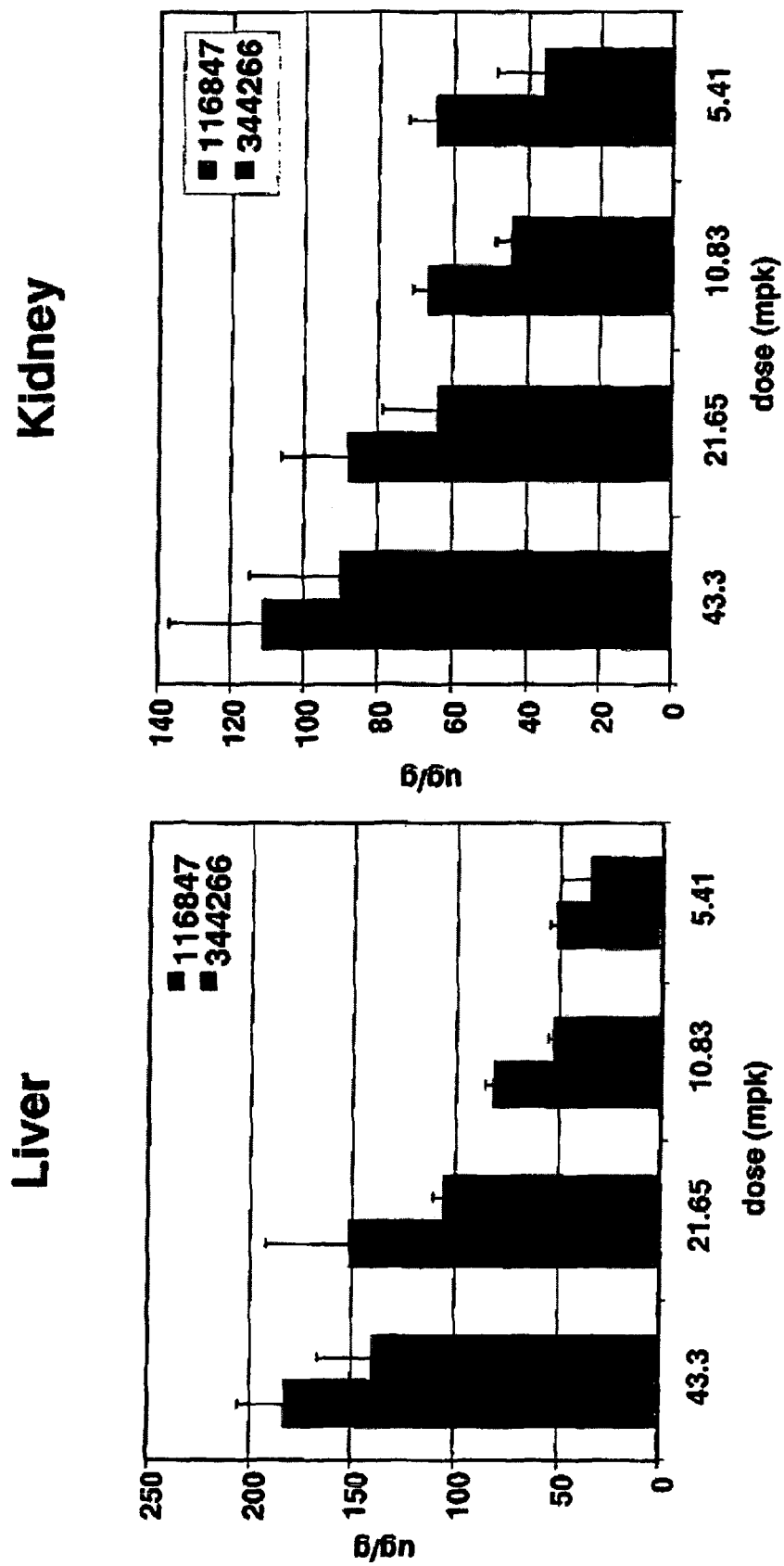
Figure 4: Liver and kidney concentrations (5-10-5 vs. 2-16-2)

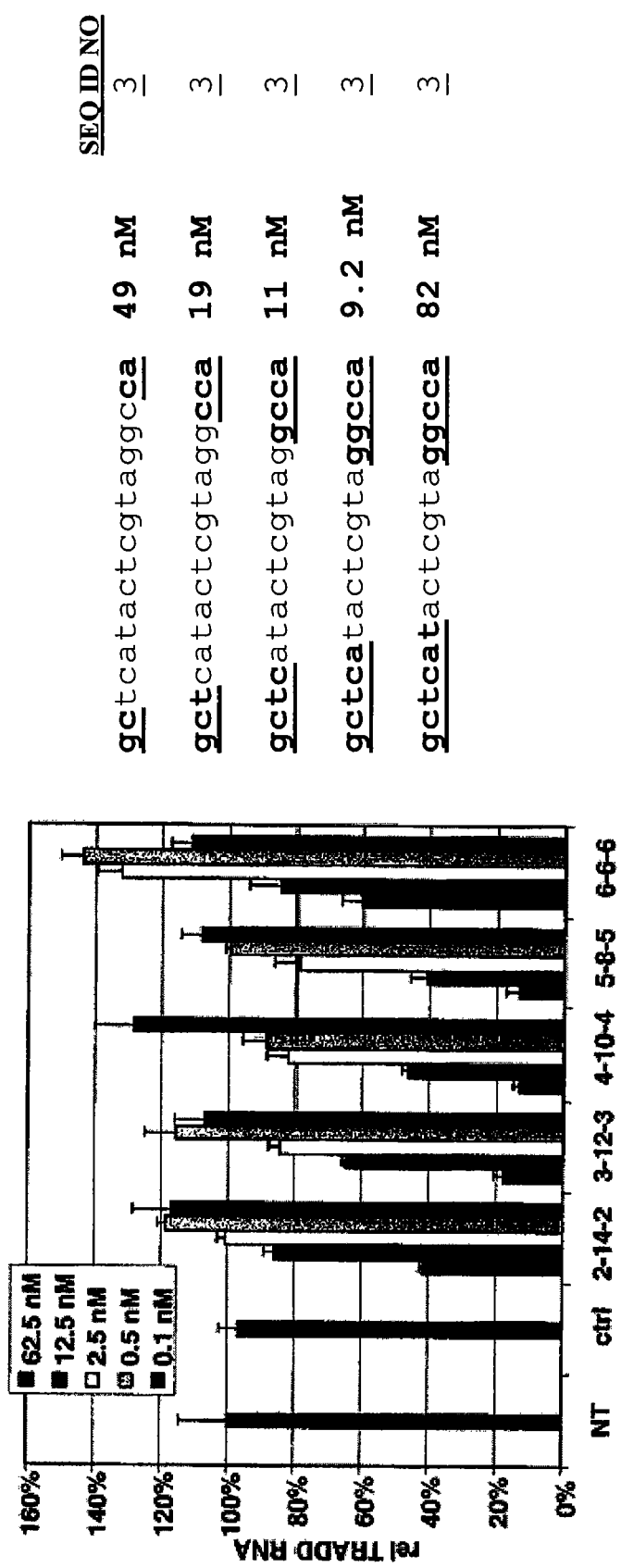
Figure 5: mTRADD MOE gapmer gap walk in bEND cells

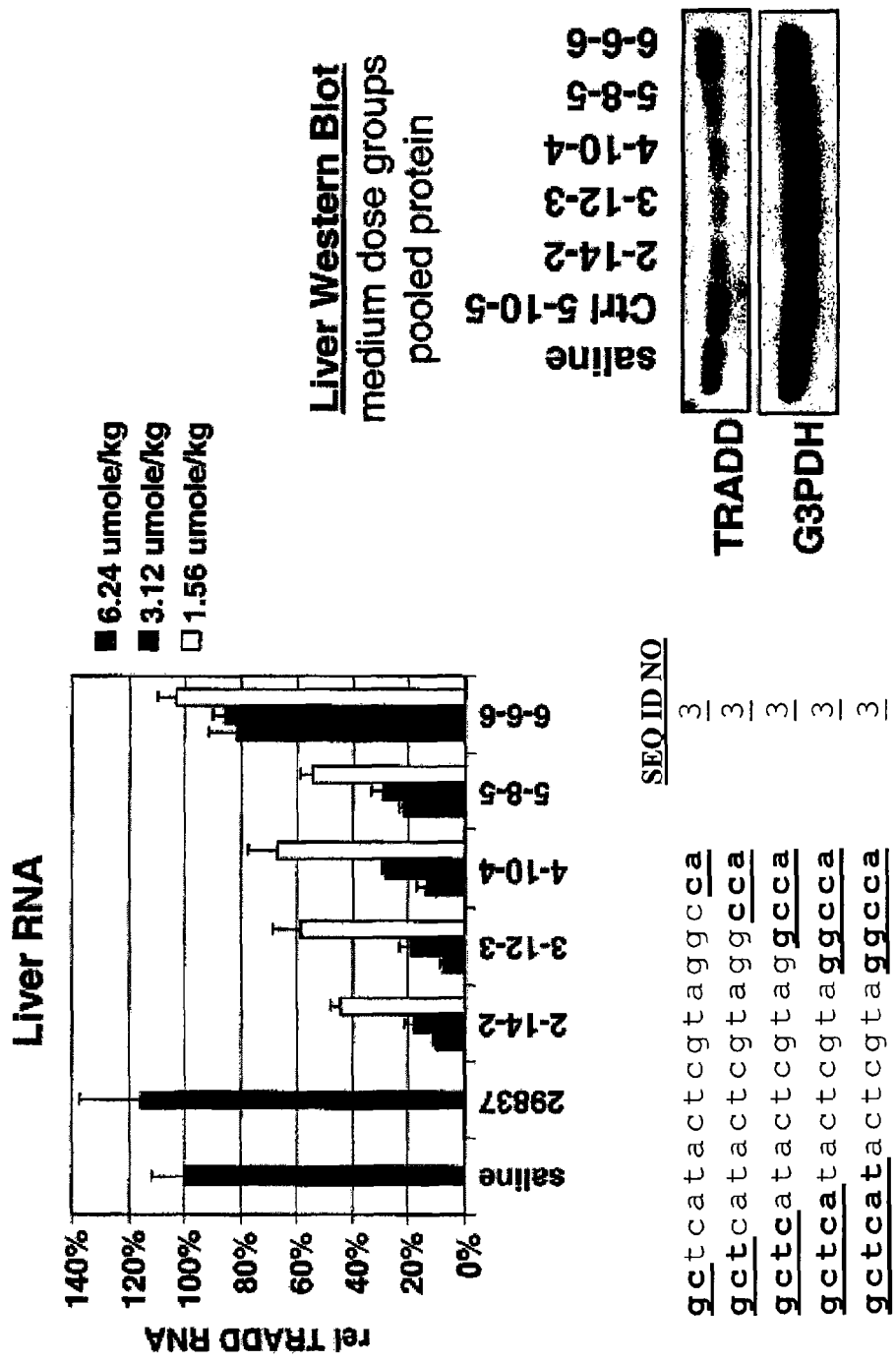
Figure 6: mTRADD MOE gapmer gap walk-target reduction in vivo

ENHANCED ANTISENSE OLIGONUCLEOTIDES

CROSS-REFERENCE TO RELATED APPLICATIONS

This application claims the priority to U.S. Application No. 60/611,100 filed on Sep. 17, 2004 and to U.S. Application No. 60/663,442 filed on Mar. 18, 2005, each of which is herein incorporated by reference in its entirety. The instant application is also related to U.S. Application 60/718,685, and U.S. Application 60/718,684, each of which was filed on the same day as the instant application and is herein incorporated by reference in its entirety.

SEQUENCE LISTING

A paper copy of the sequence listing and a computer-readable form of the sequence listing, on diskette, containing the file named CORE0051USSEQ.txt, which was created on Sep. 19, 2005, are herein incorporated by reference.

FIELD OF THE INVENTION

The present invention provides chimeric antisense compounds having enhanced in vivo potency and thus an improved therapeutic index. The compounds described herein have widened deoxy gaps and enhanced in vivo potency which is unexpected based on their in vitro activity.

BACKGROUND OF THE INVENTION

Antisense oligonucleotides are accepted therapeutic modalities and many thousands of patients have been treated with antisense compounds. The original "first generation" antisense compounds employed in the first antisense clinical trials were oligodeoxynucleotides having 2'-deoxy ribonucleotides and phosphorothioate internucleoside linkages. Subsequently, chimeric "second generation" antisense oligonucleotides exhibited a marked improvement in potency over first generation antisense oligonucleotides. Second generation antisense oligonucleotides are chimeric oligonucleotides typically having a 2'-deoxy "gap" region flanked by "wings" having nucleotides with 2'-modified ribonucleotides, referred to as "gapmers." The most widely used of the "second generation" antisense motifs is often referred to as a "MOE gapmer" in which the 2'-modified ribonucleotide is a 2'-O-methoxyethyl (2'-MOE or simply MOE) modification, and each of the internucleotide linkages is a phosphorothioate. Predominantly, second generation oligonucleotides have a length of 20 nucleotides of which the 5 nucleotides at each terminus are 2'-MOE nucleotides and the center ten nucleotides are 2'-deoxyribonucleotides. These second generation oligonucleotides are referred to as "5-10-5 MOE gapmers" have a 5-10-5 wing-gap-wing motif. Chimeric antisense compounds with other arrangements of modifications have also been made. "Hemimers," are chimeric compounds in which there is a single 2'-modified "wing" adjacent to (on either the 5', or the 3' side of) a 2'-deoxy gap have been described (Geary et al., 2001, J. Pharm. Exp. Therap., 296, 898-904).

SUMMARY OF THE INVENTION

The present invention is directed to "gap-widened" antisense oligonucleotides having a gap region of greater than 11 2'deoxyribonucleotides flanked by two "wing" regions having from one to eight nucleotides which do not support RNase H activity. The gap-widened antisense oligonucleotide of the present invention have been shown to have an improved therapeutic index as compared to a corresponding antisense oligonucleotide having a 5-10-5 MOE gamer antisense oligonucleotide with the same sequence. The gap-widened antisense oligonucleotides of the present invention exhibit increased in vivo potency or improved tissue exposure as compared with the corresponding 5-10-5 MOE gapmer antisense oligonucleotide with the same sequence. Most interestingly, there is a lack of correlation between the in vitro potency and the in vivo potency of the gap-widened antisense oligonucleotides described herein. The gap-widened antisense oligonucleotides of the present invention are 18 to 24 nucleotides in length. In particular, the gap-widened antisense oligonucleotides of the present invention have wing regions having 2'-O-(2-methoxyethyl) ribonucleotides.

In an additional embodiment of the present invention is a method of reducing expression of a target RNA in an animal in need of reducing expression of said target RNA, comprising administering to said animal a gap-widened antisense oligonucleotide 18 to 24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl) ribonucleotides, having an improved therapeutic index as compared to a corresponding 5-10-5 MOE gapmer antisense oligonucleotide having a gap region of 10 contiguous 2'-deoxyribonucleotides and a first wing region and a second wing region flanking the gap region of 5 2'-O-(2-methoxyethyl) ribonucleotides. The improvement in therapeutic index is characterized by equal or increased potency coupled with a reduction in tissue concentration, or increased potency coupled with equal tissue exposures as compared to a corresponding 5-10-5 MOE gapmer antisense oligonucleotide of the same sequence. In addition, the improvement in therapeutic index may be characterized by an increased liver to kidney concentration ratio as compared to a corresponding 5-10-5 MOE gapmer antisense oligonucleotide of the same sequence. In particular, the method of the present invention is useful in reducing the expression of RNA targets expressed in the kidney, liver, or adipose tissues. The method of the present invention is also useful in reducing the expression of target RNA associated with a metabolic or cardiovascular disease or condition. The method of the present invention is useful wherein the metabolic disease or condition is selected from diabetes, hepatic steatosis, fatty liver disease, non-alcoholic steatohepatitis, metabolic syndrome, obesity, or the like. In addition, the method of the present invention is useful wherein the cardiovascular disease or condition is selected from hypercholesterolemia, atherosclerosis, hyperlipidemia, familial hypercholesterolemia, or the like.

An additional method of the present invention is a method of selecting a gap-widened antisense oligonucleotide with an improved therapeutic index, the method comprising:

screening in vitro a plurality of antisense oligonucleotides targeting a human RNA and having a single wing-gap-wing motif;

identifying a parent antisense oligonucleotide from the plurality of antisense oligonucleotides having a potent in vitro activity;

synthesizing a plurality of gap-widened antisense oligonucleotides having the same sequence as the parent antisense oligonucleotide, wherein said gap-widened antisense oligonucleotide is 18 to 24 nucleotides in length comprising a gap region having greater than 11 contiguous 2'-deoxyribonucleotides; and a first wing region and a second wing region flanking the gap region, wherein each of said first and second wing regions independently has 1 to 8 2'-O-(2-methoxyethyl) ribonucleotides;

testing said plurality of gap-widened antisense oligonucleotides in a plurality of animals;

obtaining potency and tissue concentration data from said testing step; and determining an optimized gap-widened oligonucleotide wing-gap-wing motif with an improved therapeutic index, improved potency, reduced tissue exposure, or reduced toxicity, or a combination thereof as compared to the parent antisense oligonucleotide.

In one embodiment, the method of selecting a gap-widened antisense oligonucleotide further comprises the step of designing a rodent sequence analogous or a non-human primate sequence to said parent antisense oligonucleotide. In one embodiment, the step of determining the optimized gap-widened antisense oligonucleotide wing-gap-wing motif with an improved therapeutic index includes identifying a gap-widened antisense oligonucleotide which has equal or increased potency as compared to the parent antisense oligonucleotide.

In the step of screening, each of said antisense oligonucleotides has the same wing-gap-wing motif selected from 2-16-2, 3-14-3, 4-12-4, or 5-10-5. In a further embodiment, the wing portions of the gap-widened antisense oligonucleotides are 2'-O-(2-methoxyethyl) ribonucleotides. In particular, the step of screening is performed in primary hepatocytes, HepG2, bEND, or HeLa cells. In the step of identifying, the potent in vitro activity is greater than 50% reduction in the target mRNA expression as compared to a saline control. In alternate embodiments, in the step of identifying, the potent in vitro activity is greater than 30%, greater than 40%, greater than 50%, greater than 60%, greater than 70%, greater than 80%, or greater than 90%

In the step of synthesizing, the gap-widened antisense oligonucleotides each have different wing-gap-wing motifs. In particular, the gap-widened antisense oligonucleotides have gaps of 12, 13, 14, 15, 16, 17, or 18 2'-deoxyribonucleotides in length. In the step of testing, the animals are selected from rodents such as mice and rats, and non-human primates, such as cynomolgous monkeys.

In the step of obtaining, the tissue concentration data are concentrations of full-length gap-widened antisense oligonucleotides particularly measured in the liver, kidney, or adipose tissue. In one embodiment, each optimized gap-widened antisense oligonucleotide is selected because of equal or improved potency data. In another embodiment, each optimized gap-widened antisense oligonucleotide is selected because of reduced tissue exposure. In another embodiment, each optimized gap-widened antisense oligonucleotide is selected because of reduced toxicity. In another embodiment, each optimized gap-widened antisense oligonucleotide is selected because of improved therapeutic index. In another embodiment, each optimized gap-widened antisense oligonucleotide is selected because of reduced tissue exposure, reduced toxicity, improved potency, or a combination thereof.

The gap-widened antisense oligonucleotides described herein may have various wing-gap-wing motifs selected from: 1-16-1, 2-15-1, 1-15-2, 1-14-3, 3-14-1, 2-14-2, 1-13-4, 4-13-1, 2-13-3, 3-13-2, 1-12-5, 5-12-1, 2-12-4, 4-12-2, 3-12-3, 1-11-6, 6-11-1, 2-11-5, 5-11-2, 3-11-4, 4-11-3, 1-17-1, 2-16-1, 1-16-2, 1-15-3, 3-15-1, 2-15-2, 1-14-4, 4-14-1, 2-14-3, 3-14-2, 1-13-5, 5-13-1, 2-13-4, 4-13-2, 3-13-3, 1-12-6, 6-12-1, 2-12-5, 5-12-2, 3-12-4, 4-12-3, 1-11-7, 7-11-1, 2-11-6, 6-11-2, 3-11-5, 5-11-3, 4-11-4, 1-18-1, 1-17-2, 2-17-1, 1-16-3, 1-16-3, 2-16-2, 1-15-4, 4-15-1, 2-15-3, 3-15-2, 1-14-5, 5-14-1, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-18-1, 1-17-2, 2-17-1, 1-16-3, 1, 2-16-2, 1-15-4, 4-15-1, 2-15-3, 3-15-2, 1-14-5, 2-14-4, 4-14-2, 3-14-3, 1-13-6, 6-13-1, 2-13-5, 5-13-2, 3-13-4, 4-13-3, 1-12-7, 7-12-1, 2-12-6, 6-12-2, 3-12-5, 5-12-3, 4-12-4, 1-11-8, 8-11-1, 2-11-7, 7-11-2, 3-11-6, 6-11-3, 4-11-5, 5-11-4, 1-19-1, 1-18-2, 2-18-1, 1-17-3, 3-17-1, 2-17-2, 1-16-4, 4-16-1, 2-16-3, 3-16-2, 1-15-5, 2-15-4, 4-15-2, 3-15-3, 1-14-6, 6-14-1, 2-14-5, 5-14-2, 3-14-4, 4-14-3, 1-13-7, 7-13-1, 2-13-6, 6-13-2, 3-13-5, 5-13-3, 4-13-4, 1-12-8, 8-12-1, 2-12-7, 7-12-2, 3-12-6, 6-12-3, 4-12-5, 5-12-4, 2-11-8, 8-11-2, 3-11-7, 7-11-3, 4-11-6, 6-11-4, 5-11-5, 1-20-1, 1-19-2, 2-19-1, 1-18-3, 3-18-1, 2-18-2, 1-17-4, 4-17-1, 2-17-3, 3-17-2, 1-16-5, 2-16-4, 4-16-2, 3-16-3, 1-15-6, 6-15-1, 2-15-5, 5-15-2, 3-15-4, 4-15-3, 1-14-7, 7-14-1, 2-14-6, 6-14-2, 3-14-5, 5-14-3, 4-14-4, 1-13-8, 8-13-1, 2-13-7, 7-13-2, 3-13-6, 6-13-3, 4-13-5, 5-13-4, 2-12-8, 8-12-2, 3-12-7, 7-12-3, 4-12-6, 6-12-4, 5-12-5, 3-11-8, 8-11-3, 4-11-7, 7-11-4, 5-11-6, 6-11-5, 1-21-1, 1-20-2, 2-20-1, 1-20-3, 3-19-1, 2-19-2, 1-18-4, 4-18-1, 2-18-3, 3-18-2, 1-17-5, 2-17-4, 4-17-2, 3-17-3, 1-16-6, 6-16-1, 2-16-5, 5-16-2, 3-16-4, 4-16-3, 1-15-7, 7-15-1, 2-15-6, 6-15-2, 3-15-5, 5-15-3, 4-15-4, 1-14-8, 8-14-1, 2-14-7, 7-14-2, 3-14-6, 6-14-3, 4-14-5, 5-14-4, 2-13-8, 8-13-2, 3-13-7, 7-13-3, 4-13-6, 6-13-4, 5-13-5, 1-12-10, 10-12-1, 2-12-9, 9-12-2, 3-12-8, 8-12-3, 4-12-7, 7-12-4, 5-12-6, 6-12-5, 4-11-8, 8-11-4, 5-11-7, 7-11-5, 6-11-6, 1-22-1, 1-21-2, 2-21-1, 1-21-3, 3-20-1, 2-20-2, 1-19-4, 4-19-1, 2-19-3, 3-19-2, 1-18-5, 2-18-4, 4-18-2, 3-18-3, 1-17-6, 6-17-1, 2-17-5, 5-17-2, 3-17-4, 4-17-3, 1-16-7, 7-16-1, 2-16-6, 6-16-2, 3-16-5, 5-16-3, 4-16-4, 1-15-8, 8-15-1, 2-15-7, 7-15-2, 3-15-6, 6-15-3, 4-15-5, 5-15-4, 2-14-8, 8-14-2, 3-14-7, 7-14-3, 4-14-6, 6-14-4, 5-14-5, 3-13-8, 8-13-3, 4-13-7, 7-13-4, 5-13-6, 6-13-5, 4-12-8, 8-12-4, 5-12-7, 7-12-5, 6-12-6, 5-11-8, 8-11-5, 6-11-7, or 7-11-6. In a particular embodiment, the gap-widened antisense oligonucleotides of the present invention have a 2-16-2, 3-14-3, or 4-12-4 wing-gap-wing motif.

Another aspect of the present invention is the use of a gap-widened antisense oligonucleotide 18-24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl) ribonucleotides, having an improved therapeutic index as compared to a corresponding 5-10-5 antisense oligonucleotide having a gap region of 10 contiguous 2'-deoxyribonucleotides and a first wing region and a second wing region flanking the gap region of 5 2'-O-(2-methoxyethyl) ribonucleotides in the manufacture of a medicament for the treatment of disorders and diseases related to target RNA levels. Another embodiment of the present invention is a pharmaceutical composition comprising a gap-widened antisense oligonucleotide 18-24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2-methoxyethyl) ribonucleotides, having an improved therapeutic index as compared to a corresponding 5-10-5 antisense oligonucleotide having a gap region of 10 contiguous 2'-deoxyribonucleotides and a first wing region and a second wing region flanking the gap region of 5 2'-O-(2-methoxyethyl) ribonucleotides and optionally a pharmaceutically acceptable carrier, diluent, enhancer or excipient. Another embodiment of the present invention is a gap-widened antisense oligonucleotide 18-24 nucleotides in length comprising: a gap region having greater than 11 contiguous 2'-deoxyribonucleotides; and a first wing region and a second wing region flanking the gap region, wherein each of said first and second wing regions independently have 1 to 8 2'-O-(2methoxyethyl) ribonucleotides, having lower kidney accumulation as compared to a corresponding 5-10-5 antisense oligonucleotide having a gap region of 10 contiguous 2'-deoxyribonucleotides and a first wing region and a second wing region flanking the gap region of 5 2'-O-(2-methoxyethyl) ribonucleotides as measured by plasma protein binding capacity of said gap-widened antisense oligonucleotide. Also provided is a method of modulating gene expression in an animal comprising the step of contacting said animal with the pharmaceutical composition. Another embodiment is a method of modulating gene expression in an animal comprising the step of contacting said animal with a gap-widened antisense oligonucleotide of the invention wherein the accumulation of the gap-widened antisense oligonucleotide in the kidney is less compared to a corresponding 5-10-5 antisense oligonucleotide having a gap region of 10 contiguous 2'-deoxyribonucleotides and a first wing region and a second wing region flanking the gap region of 5 2'-O-(2-methoxyethyl) ribonucleotides. In one embodiment, the kidney accumulation is measured by plasma protein binding capacity of said gap-widened antisense oligonucleotide.

Another embodiment of the present invention is a method of reducing levels of a preselected RNA target in the liver of an animal comprising administering to said animal a chimeric antisense compound 11 to 80 nucleobases in length which is targeted to said preselected RNA target wherein said chimeric antisense compound comprises a first gap region consisting of at least 10 contiguous 2'-deoxynucleotides and a wing region which consists of from 1 to 4 contiguous nucleosides or nucleoside analogs which are not substrates for RNaseH. In particular embodiments, said first gap region consists of at least 11, at least 12, at least 13, at least 14, at least 15, at least 16, at least 17, or at least 18 contiguous 2'-deoxynucleotides. In one embodiment, the chimeric antisense compound comprises second wing region which consists of from 1 to 7 contiguous nucleosides or nucleoside analogs which are not substrates for RNase H, and wherein said gap region is located between said first wing region and said second wing region. In another embodiment, the chimeric antisense compound is a chimeric antisense oligonucleotide, and the nucleosides or nucleoside analog which is not a substrate for RNase H is a nucleotide having a 2' modification of the sugar moiety. In one embodiment, the nucleotide having a 2' modification of the sugar moiety is a 2'-O-methoxyethyl nucleotide. In some embodiments the compound is a 2-16-2 MOE gapmer, a 3-12-3 MOE gapmer, a 3-10-7 MOE gapmer or a 7-10-3 MOE gapmer. In one embodiment, the chimeric antisense oligonucleotide has at least one phosphorothioate backbone linkage.

Another embodiment of the present invention is a pharmaceutical composition for use in reducing levels of a preselected RNA target in the liver of an animal comprising a chimeric antisense compound targeted to said preselected RNA target, wherein said chimeric antisense compound comprises a first gap region consisting of at least 10 contiguous 2'-deoxynucleotides and a wing region which consists of from 1 to 4 contiguous nucleosides or nucleoside analogs which are not substrates for RNase H.

BRIEF DESCRIPTION OF THE DRAWINGS

FIG. 1. Depicts a comparison of in vivo effects of a 5-10-5 MOE gapmer (SEQ ID NO:1) and the corresponding gap-widened 2-16-2 MOE gapmer (SEQ ID NO:1).

FIG. 2. Depicts a comparison the persistence of target mRNA modulation of a 5-10-5 MOE gapmer (SEQ ID NO:1) and the corresponding gap-widened 2-16-2 MOE gapmer (SEQ ID NO:1).

FIG. 3. Depicts a comparison of in vitro effects of a 5-10-5 MOE gapmer and the corresponding gap-widened 2-16-2 MOE gapmer.

FIG. 4. Depicts a comparison of the concentrations of a 5-10-5 MOE gapmer and the corresponding gap-widened 2-16-2 MOE gapmer in liver and kidney tissues.

FIG. 5. Depicts a comparison of the in vitro effects of oligonucleotides having the same sequence (SEQ ID NO:3) but varied wing-gap-wing motifs.

FIG. 6. Depicts a comparison of the in vivo effects of oligonucleotides having the same sequence (SEQ ID NO:3) but varied wing-gap-wing motifs.

DETAILED DESCRIPTION OF THE INVENTION

Certain gap sizes are optimal for in vivo efficacy of antisense compounds. Surprisingly, improved potency (3-10× improvement) in mouse or rat liver has been demonstrated for gap-widened antisense oligonucleotides compared to standard 5-10-5 MOE gapmer (for example, 2-16-2, 2-14-2, 3-12-3 gapmers) antisense oligonucleotides. This has been shown for several distinct antisense targets and this improved potency is not observed in cultured cells transfected with the same gap-widened antisense oligonucleotides. Thus the "gap-widened" motifs appear to convey some benefit to in vivo potency, particularly in the liver. It is demonstrated herein that chimeric antisense compounds having a gap of greater than eleven contiguous deoxynucleotides flanked by wing regions consisting of from 1 to 4 nucleotides which are not substrates for RNase H are particularly effective at reducing target RNA levels in vivo, particularly in the liver.

Therapeutic Index

Therapeutic index is a measure which relates the dose of a drug required to produce a specified effect to that which produces an undesired effect. In one embodiment, improved therapeutic index of a gap-widened antisense oligonucleotide is characterized by equal or increased potency and a reduction in tissue concentration. In another embodiment, improved therapeutic index of a gap-widened antisense oligonucleotide is characterized by increased potency and equal tissue concentrations as compared to a corresponding 5-10-5 antisense oligonucleotide. In another embodiment, improved therapeutic index of a gap-widened antisense oligonucleotide is characterized by increased potency and decreased toxicity as compared to a corresponding 5-10-5 antisense oligonucleotide. In another embodiment, improved therapeutic index of a gap-widened antisense oligonucleotide is characterized by comparable potency and decreased toxicity as compared to a corresponding 5-10-5 antisense oligonucleotide. In some embodiments, the toxicity is renal toxicity. In some embodiments, the toxicity is hepatic toxicity.

Indications

An embodiment of the present invention is a method of treating a disease or condition wherein a target RNA is associated with said disease or condition by administering a compound of the invention. Another embodiment of the present invention is a method of preventing or delaying the onset of a disease or condition wherein a target RNA is associated with said disease or condition by administering a compound of the invention. Diseases or conditions include metabolic and cardiovascular diseases or conditions. In some embodiments, the disease or condition is metabolic syndrome, diabetes, obesity, hyperlipidemia, hypercholesterolemia, hypertriglyceridemia, Type 2 diabetes, diet-induced obesity, hyperglycemia, or insulin resistance. In one embodiment, the disease or condition is hepatic steatosis. In some embodiments, the steatosis is steatohepatitis or NASH. In some embodiments, the disease or condition is familial hypercholesterolemia, nonfamilial hypercholesterolemia, mixed dyslipidemia, dysbetalipoproteinemia, atherosclerosis, coronary artery disease, myocardial infarction, hypertension, carotid artery diseases, stroke, cerebrovascular disease, carotid artery disease, stroke, cerebrovascular disease, peripheral vascular disease, thrombosis, or arterial aneurism.

NAFLD and Metabolic Syndrome

The term "nonalcoholic fatty liver disease" (NAFLD) encompasses a disease spectrum ranging from simple triglyceride accumulation in hepatocytes (hepatic steatosis) to hepatic steatosis with inflammation (steatohepatitis), fibrosis, and cirrhosis. Nonalcoholic steatohepatitis (NASH) occurs from progression of NAFLD beyond deposition of triglycerides. A second-hit capable of inducing necrosis, inflammation, and fibrosis is required for development of NASH. Candidates for the second-hit can be grouped into broad categories: factors causing an increase in oxidative stress and factors promoting expression of proinflammatory cytokines. It has been suggested that increased liver triglycerides lead to increased oxidative stress in hepatocytes of animals and humans, indicating a potential cause-and-effect relationship between hepatic triglyceride accumulation, oxidative stress, and the progression of hepatic steatosis to NASH (Browning and Horton, *J. Clin. Invest.*, 2004, 114, 147-152). Hypertriglyceridemia and hyperfattyacidemia can cause triglyceride accumulation in peripheral tissues (Shimamura et al., *Biochem. Biophys. Res. Commun.*, 2004, 322, 1080-1085).

"Metabolic syndrome" is defined as a clustering of lipid and non-lipid cardiovascular risk factors of metabolic origin. It is closely linked to the generalized metabolic disorder known as insulin resistance. The National Cholesterol Education Program (NCEP) Adult Treatment Panel III (ATPIII) established criteria for diagnosis of metaolic syndrome when three or more of five risk determinants are present. The five risk determinants are abdominal obesity defined as waist circumference of greater than 102 cm for men or greater than 88 cm for women, triglyceride levels greater than or equal to 150 mg/dL, HDL cholesterol levels of less than 40 mg/dL for men and less than 50 mg/dL for women, blood pressure greater than or equal to 130/85 mm Hg and fasting glucose levels greater than or equal to 110 mg/dL. These determinants can be readily measured in clinical practice (*JAMA*, 2001, 285, 2486-2497).

HbA1c

HbA1c is a stable minor hemoglobin variant formed in vivo via posttranslational modification by glucose, and it contains predominantly glycated NH2-terminal β-chains. There is a strong correlation between levels of HbA1c and the average blood glucose levels over the previous 3 months. Thus HbA1c is often viewed as the "gold standard" for measuring sustained blood glucose control (Bunn, H. F. et al., 1978, Science. 200, 21-7). HbA1c can be measured by ion-exchange HPLC or immunoassay; home blood collection and mailing kits for HbA1c measurement are now widely available. Serum fructosamine is another measure of stable glucose control and can be measured by a colorimetric method (Cobas Integra, Roche Diagnostics).

Cardiovascular Risk Profile

Conditions associated with risk of developing a cardiovascular disease include, but are not limited to, history of myocardial infarction, unstable angina, stable angina, coronary artery procedures (angioplasty or bypass surgery), evidence of clinically significant myocardial ischemia, noncoronary forms of atherosclerotic disease (peripheral arterial disease, abdominal aortic aneurysm, carotid artery disease), diabetes, cigarette smoking, hypertension, low HDL cholesterol, family history of premature CHD, obesity, physical inactivity, elevated triglyceride, or metabolic syndrome (Jama, 2001, 285, 2486-2497; Grundy et al., Circulation, 2004, 110, 227-239).

EXAMPLES

Example 1

Oligonucleotide Sequences and Targets

TABLE 1

Oligonucleotide sequences (all are PS backbone) Modified nucleotides are shown in Bold (2'MOE unless otherwise indicated) and all cytosines are 5-methylcytosines

| ISIS No. | Target | Sequence | SEQ ID NO | Motif |
|---|---|---|---|---|
| 116847 | PTEN | CTGCTAGCCTCTGGATTTGA | 1 | 5-10-5 |
| 344266 | PTEN | CTGCTAGCCTCTGGATTTGA | 1 | 2-16-2 |
| 141923 | None (scrambled) | CCTTCCCTGAAGGTTCCTC | 2 | 5-10-5 |
| 117405 | TRADD | GCTCATACTCGTAGGCCA | 3 | 4-10-4 |
| 325589 | TRADD | GCTCATACTCGTAGGCCA | 3 | 5-8-5 |
| 325590 | TRADD | GCTCATACTCGTAGGCCA | 3 | 6-6-6 |
| 29837 | None (scrambled) | TCGATCTCCTTTTATGCCCG | 4 | 5-10-5 |
| 325593 | mTRADD | CGCTCATACTCGTAGGCCAG | 112 | 3-10-7 |
| 325594 | TRADD | CGCTCATACTCGTAGGCCAG | 112 | 7-10-3 |
| 325584 | TRADD | CGCTCATACTCGTAGGCCAG | 112 | 5-10-5 |
| 113715 | PTP1B | GCTCCTTCCACTGATCCTGC | 113 | 5-10-5 |
| 344177 | PTP1B | GCTCCTTCCACTGATCCTGC | 113 | 3-14-3 |
| 372350 | GCCR | TCTGTCTCTCCCATATACAG | 5 | 2-16-2 |
| 372376 | GCCR | TGTTTCTGTCTCTCCCATAT | 6 | 2-16-2 |
| 372331 | GCCR | CTTTTGTTTCTGTCTCTCCC | 7 | 2-16-2 |
| 372341 | GCCR | ATCACTTTTGTTTCTGTCTC | 8 | 2-16-2 |
| 352983 | GCCR | GTTTGCAATGCTTTCTTCCA | 9 | 2-16-2 |
| 372365 | GCCR | TGAGGTTTGCAATGCTTTCT | 10 | 2-16-2 |
| 372387 | GCCR | CTATTGAGGTTTGCAATGCT | 11 | 2-16-2 |
| 372316 | GCCR | CGACCTATTGAGGTTTGCAA | 12 | 2-16-2 |
| 372310 | GCCR | CTGGTCGACCTATTGAGGTT | 13 | 2-16-2 |
| 372315 | GCCR | CTGTGGTATACAATTTCACA | 14 | 2-16-2 |
| 372326 | GCCR | CTTTGGTCTGTGGTATACAA | 15 | 2-16-2 |
| 372339 | GCCR | GTCAAAGGTGCTTTGGTCTG | 16 | 2-16-2 |

TABLE 1-continued

Oligonucleotide sequences (all are PS backbone) Modified nucleotides are shown in Bold (2'MOE unless otherwise indicated) and all cytosines are 5-methylcytosines

| ISIS No. | Target | Sequence | SEQ ID NO | Motif |
|---|---|---|---|---|
| 372322 | GCCR | GGTTTAGTGTCCGGTAAAAT | 17 | 2-16-2 |
| 372361 | GCCR | CTTTTTCTGTTTTCACTTGG | 18 | 2-16-2 |
| 372308 | GCCR | TTCTCTTTGCTTAATTACCCC | 19 | 2-16-2 |
| 372304 | GCCR | CAGTTTCTCTTGCTTAATTA | 20 | 2-16-2 |
| 352984 | GCCR | GCCCAGTTTCTCTTGCTTAA | 21 | 2-16-2 |
| 372372 | GCCR | TTTATTACCAATTATATTTG | 22 | 2-16-2 |
| 372327 | GCCR | ACATTTTATTACCAATTATA | 23 | 2-16-2 |
| 372311 | GCCR | GCAGACATTTTATTACCAAT | 24 | 2-16-2 |
| 372352 | GCCR | AATGGCAGACATTTTATTAC | 25 | 2-16-2 |
| 372337 | GCCR | CAGAAATGGCAGACATTTTA | 26 | 2-16-2 |
| 372323 | GCCR | TGAACAGAAATGGCAGACAT | 27 | 2-16-2 |
| 372347 | GCCR | CCATGAACAGAAATGGCAGA | 28 | 2-16-2 |
| 372383 | GCCR | CACACCATGAACAGAAATGG | 29 | 2-16-2 |
| 372348 | GCCR | TACTCACACCATGAACAGAA | 30 | 2-16-2 |
| 372363 | GCCR | GAGGTACTCACACCATGAAC | 31 | 2-16-2 |
| 372334 | GCCR | TCCAGAGGTACTCACACCAT | 32 | 2-16-2 |
| 372359 | GCCR | GTCCTCCAGAGGTACTCACA | 33 | 2-16-2 |
| 372344 | GCCR | ATCTGTCCTCCAGAGGTACT | 34 | 2-16-2 |
| 372307 | GCCR | GTACATCTGTCCTCCAGAGG | 35 | 2-16-2 |
| 372370 | GCCR | AGTGGTACATCTGTCCGTCCA | 36 | 2-16-2 |
| 372374 | GCCR | TCATAGTGGTACATCTGTCC | 37 | 2-16-2 |
| 372355 | GCCR | CATGTCATAGTGGTACATCT | 38 | 2-16-2 |
| 372385 | GCCR | TATTCATGTCATAGTGGTAC | 39 | 2-16-2 |
| 372319 | GCCR | GCTGTATTCATGTCATAGTG | 40 | 2-16-2 |
| 372366 | GCCR | GGATGCTGTATTCATGTCAT | 41 | 2-16-2 |
| 372330 | GCCR | AAAGGGATGCTGTATTCATG | 42 | 2-16-2 |
| 372333 | GCCR | TGAGAAAGGGATGCTGTATT | 43 | 2-16-2 |
| 372358 | GCCR | TGGTGGAATGACATTAAAAA | 44 | 2-16-2 |
| 372381 | GCCR | GAATTGGTGGAATGACATTA | 45 | 2-16-2 |
| 372377 | GCCR | GAGCTTACATCTGGTCTCAT | 46 | 2-16-2 |
| 372309 | GCCR | AGGAGAGCTTACATCTGGTC | 47 | 2-16-2 |
| 372388 | GCCR | ATGGAGGAGAGCTTACATCT | 48 | 2-16-2 |
| 372321 | GCCR | CTGGATGGAGGAGAGCTTAC | 49 | 2-16-2 |
| 372312 | GCCR | GAGCTGGATGGAGGAGAGCT | 50 | 2-16-2 |
| 372324 | GCCR | TGTCCTTCCACTGCTCTTTT | 51 | 2-16-2 |
| 372332 | GCCR | GTGCTGTCCTTCCACTGCTC | 52 | 2-16-2 |
| 372335 | GCCR | AATTGTGCTGTCCTTCCACT | 53 | 2-16-2 |
| 372342 | GCCR | AGGTAATTGTGCTGTCCTTC | 54 | 2-16-2 |
| 372345 | GCCR | CGGCATGCTGGGCAGTTTTT | 55 | 2-16-2 |
| 372356 | GCCR | ATAGCGGCATGCTGGGCAGT | 56 | 2-16-2 |
| 372305 | GCCR | CGATAGCGGCATGCTGGGCA | 57 | 2-16-2 |
| 372367 | GCCR | ATTCCAGCCTGAAGACATTT | 58 | 2-16-2 |
| 372353 | GCCR | GTTCATTCCAGCCTGAAGAC | 59 | 2-16-2 |
| 372364 | GCCR | TTCTTTGTTTTCGAGCTTC | 60 | 2-16-2 |
| 372340 | GCCR | TTTTTTCTTTGTTTTCGAG | 61 | 2-16-2 |
| 372369 | GCCR | CAGGAACTATTGTTTTGTTA | 62 | 2-16-2 |
| 372378 | GCCR | TGCAGGAACTATTGTTTTGT | 63 | 2-16-2 |
| 372317 | GCCR | GAGCTATCATATCCTGCATA | 64 | 2-16-2 |
| 372351 | GCCR | AACAGAGCTATCATATCCTG | 65 | 2-16-2 |
| 372389 | GCCR | CTGGAACAGAGCTATCATAT | 66 | 2-16-2 |
| 372362 | GCCR | TTCACTGCTGCAATCACTTC | 67 | 2-16-2 |
| 372328 | GCCR | CCATTTCACTGCTGCAATCA | 68 | 2-16-2 |
| 372338 | GCCR | TTGCCCATTTCACTGCTGCA | 69 | 2-16-2 |
| 372349 | GCCR | ATAATCAGATCAGGAGCAAA | 70 | 2-16-2 |
| 372373 | GCCR | ATTAATAATCAGATCAGGAG | 71 | 2-16-2 |
| 372360 | GCCR | GCTCATTAATAATCAGATCA | 72 | 2-16-2 |
| 372384 | GCCR | CTCTGCTCATTAATAATCAG | 73 | 2-16-2 |
| 372380 | GCCR | CATTCTCTGCTCATTAATAA | 74 | 2-16-2 |
| 372320 | GCCR | AGCATGTGTTTACATTGGTC | 75 | 2-16-2 |
| 372371 | GCCR | AAGGTTTTCATACAGAGATA | 76 | 2-16-2 |
| 372382 | GCCR | CAGTAAGGTTTTCATACAGA | 77 | 2-16-2 |
| 372306 | GCCR | GAAGCAGTAAGGTTTTCATA | 78 | 2-16-2 |
| 372343 | GCCR | GAGAGAAGCAGTAAGGTTTT | 79 | 2-16-2 |
| 372313 | GCCR | GCTTTTCCTAGCTCTTTGAT | 80 | 2-16-2 |
| 372325 | GCCR | ATGGCTTTTCCTAGCTCTTT | 81 | 2-16-2 |
| 372336 | GCCR | ATGGTCTTATCCAAAATGT | 82 | 2-16-2 |
| 372318 | GCCR | ACTCATGGTCTTATCCAAAA | 83 | 2-16-2 |
| 372375 | GCCR | CAATACTCATGGTCTTATCC | 84 | 2-16-2 |
| 372346 | GCCR | AATTCAATACTCATGGTCTT | 85 | 2-16-2 |
| 372386 | GCCR | ATGATTTCAGCTAACATCTC | 86 | 2-16-2 |
| 372354 | GCCR | GTGATGATTTCAGCTAACAT | 87 | 2-16-2 |
| 372357 | GCCR | GAATATTTGGTATCTGATT | 88 | 2-16-2 |

TABLE 1-continued

Oligonucleotide sequences (all are PS backbone) Modified nucleotides are shown in Bold (2'MOE unless otherwise indicated) and all cytosines are 5-methylcytosines

| ISIS No. | Target | Sequence | SEQ ID NO | Motif |
|---|---|---|---|---|
| 372368 | GCCR | ATTTGAATATTTTGGTATCT | 89 | 2-16-2 |
| 372379 | GCCR | TTCCATTTGAATATTTGGT | 90 | 2-16-2 |
| 372390 | GCCR | ATATTTCCATTTGAATATT | 91 | 2-16-2 |
| 372329 | GCCR | TTTTTGATATTTCCATTGA | 92 | 2-16-2 |
| 361132 | GCCR | TCTGTCTCTCCCATATACAG | 5 | 5-10-5 |
| 361133 | GCCR | TGTTTCTGTCTCTCCCATAT | 6 | 5-10-5 |
| 361134 | GCCR | CTTTTGTTTCTGTCTCTCCC | 7 | 5-10-5 |
| 361135 | GCCR | ATCACTTTTGTTTCGTGTCTC | 8 | 5-10-5 |
| 180272 | GCCR | GTTTGCAATGCTTTCTTCCA | 9 | 5-10-5 |
| 345188 | GCCR | TGAGGTTTGCAATGCTTTCT | 10 | 5-10-5 |
| 361136 | GCCR | CTATTGAGGTTTGCAATGCT | 11 | 5-10-5 |
| 361137 | GCCR | CGACCTATTGAGGTTTGCAA | 12 | 5-10-5 |
| 180274 | GCCR | CTGGTCGACCTATTGAGGTT | 13 | 5-10-5 |
| 180275 | GCCR | CTGTGGTATACAATTTCACA | 14 | 5-10-5 |
| 180276 | GCCR | CTTTGGTCTGTGGTATACAA | 15 | 5-10-5 |
| 345198 | GCCR | GTCAAAGGTGCTTTGGTCTG | 16 | 5-10-5 |
| 180279 | GCCR | GGTTTAGTGTCCGGTAAAAT | 17 | 5-10-5 |
| 361138 | GCCR | CTTTTTCTGTTTTCACTTGG | 18 | 5-10-5 |
| 180280 | GCCR | TTCTCTTGCTTAATTACCCC | 19 | 5-10-5 |
| 345218 | GCCR | CAGTTTCTCTTGCTTAATTA | 20 | 5-10-5 |
| 180281 | GCCR | GCCCAGTTTCTCTTGCTTAA | 21 | 5-10-5 |
| 361139 | GCCR | TTTATTACCAATTATATTTG | 22 | 5-10-5 |
| 361140 | GCCR | ACATTTATTACCAATTATA | 23 | 5-10-05 |
| 361141 | GCCR | GCAGACATTTATTACCAAT | 24 | 5-10-5 |
| 361142 | GCCR | AATGGCAGACATTTATTAC | 25 | 5-10-5 |
| 361143 | GCCR | CAGAAATGGCAGACATTTTA | 26 | 5-10-5 |
| 361144 | GCCR | TGAACAGAAATGGCAGACAT | 27 | 5-10-5 |
| 180283 | GCCR | CCATGAACAGAAATGGCAGA | 28 | 5-10-5 |
| 361145 | GCCR | CACACCATGAACAGAAATGG | 29 | 5-10-5 |
| 361146 | GCCR | TACTCACACCATGAACAGAA | 30 | 5-10-5 |
| 361147 | GCCR | GAGGTACTCACACCATGAAC | 31 | 5-10-5 |
| 361148 | GCCR | TCCAGAGGTACTCACACCAT | 32 | 5-10-5 |
| 361149 | GCCR | GTCCTCCAGAGGTACTCACA | 33 | 5-10-5 |
| 361150 | GCCR | ATCTGTCCTCCAGAGGTACT | 34 | 5-10-5 |
| 361151 | GCCR | GTACATCTGTCCTCCAGAGG | 35 | 5-10-5 |
| 361152 | GCCR | AGTGGTACATCTGTCCTCCA | 36 | 5-10-5 |
| 361153 | GCCR | TCATAGTGGTACATCTGTCC | 37 | 5-10-5 |
| 361154 | GCCR | CATGTCATAGTGGTACATCT | 38 | 5-10-5 |
| 361155 | GCCR | TATTCATGTCATAGTGGTAC | 39 | 5-10-5 |
| 361156 | GCCR | GCTGTATTCATGTCATAGTG | 40 | 5-10-5 |
| 361157 | GCCR | GGATGCTGTATTCATGTCAT | 41 | 5-10-5 |
| 361158 | GCCR | AAAGGGATGCTGTATTCATG | 42 | 5-10-5 |
| 180288 | GCCR | TGAGAAAGGGATGCTGTATT | 43 | 5-10-5 |
| 180289 | GCCR | TGGTGGAATGACATTAAAAA | 44 | 5-10-05 |
| 361159 | GCCR | GAATTGGTGGAATGACATTA | 45 | 5-10-05 |
| 361160 | GCCR | GAGCTTACATCTGGTCTCAT | 46 | 5-10-5 |
| 361161 | GCCR | AGGAGAGCTTACATCTGGTC | 47 | 5-10-05 |
| 361162 | GCCR | ATGGAGGAGAGCTTACATCT | 48 | 5-10-05 |
| 361163 | GCCR | CTGGATGGAGGAGAGCTTAC | 49 | 5-10-05 |
| 361164 | GCCR | GAGCTGGATGGAGGAGAGCT | 50 | 5-10-05 |
| 361165 | GCCR | TGTCCTTCCACTGCTCTTTT | 51 | 5-10-5 |
| 361166 | GCCR | GTGCTGTCCTTCCACTCCTC | 52 | 5-10-05 |
| 361167 | GCCR | AATTGTGCTGTCCTTCCACT | 53 | 5-10-5 |
| 361168 | GCCR | AGGTAATTGTGCTGTCCTTC | 54 | 5-10-5 |
| 361169 | GCCR | CGGCATGCTGGGCAGTTTTT | 55 | 5-10-05 |
| 361170 | GCCR | ATAGCGGCATGCTGGGCAGT | 56 | 5-10-5 |
| 361171 | GCCR | CGATAGCGGCATGCTGGGCA | 57 | 5-10-5 |
| 361172 | GCCR | ATTCCAGCCTGAAGACATTT | 58 | 5-10-5 |
| 361173 | GCCR | GTTCATTCCAGCCTGAAGAC | 59 | 5-10-5 |
| 361174 | GCCR | TTCTTTGTTTTCGAGCTTC | 60 | 5-10-5 |
| 361175 | GCCR | TTTTTTCTTTGTTTTCGAG | 61 | 5-10-5 |
| 180297 | GCCR | CAGGAACTATTGTTTTGTTA | 62 | 5-10-5 |
| 361176 | GCCR | TGCAGGAACTATTGTTTTGT | 63 | 5-10-5 |
| 361177 | GCCR | GAGCTATCATATCCTGCATA | 64 | 5-10-5 |
| 361178 | GCCR | AACAGAGCTATCATATCCTG | 65 | 5-10-5 |
| 361179 | GCCR | CTGGAACAGAGCTATCATAT | 66 | 5-10-5 |
| 361180 | GCCR | TTCACTGCTGCAATCACTTG | 67 | 5-10-5 |
| 361181 | GCCR | CCATTTCACTGCTGCAATCA | 68 | 5-10-5 |
| 361182 | GCCR | TTGCCCATTTCACTGCTGCA | 69 | 5-10-5 |
| 361183 | GCCR | ATAATCAGATCAGGAGCAAA | 70 | 5-10-5 |
| 361184 | GCCR | ATTAATAATCAGATCAGGAG | 71 | 5-10-5 |
| 361185 | GCCR | GCTCATTAATAATCAGATCA | 72 | 5-10-5 |

TABLE 1-continued

Oligonucleotide sequences (all are PS backbone) Modified nucleotides are shown in Bold (2'MOE unless otherwise indicated) and all cytosines are 5-methylcytosines

| ISIS No. | Target | Sequence | SEQ ID NO | Motif |
|---|---|---|---|---|
| 361186 | GCCR | CTCTGCTCATTAATAATCAG | 73 | 5-10-5 |
| 180302 | GCCR | CATTCTCTGCTCATTAATAA | 74 | 5-10-5 |
| 180304 | GCCR | AGCATGTGTTTACATTGGTC | 75 | 5-10-5 |
| 361187 | GCCR | AAGGTTTTCATACAGAGATA | 76 | 5-10-5 |
| 361188 | GCCR | CAGTAAGGTTTTCATACAGA | 77 | 5-10-5 |
| 361189 | GCCR | GAAGCAGTAAGGTTTTCATA | 78 | 5-10-5 |
| 180307 | GCCR | GAGAGAAGCAGTAAGGTTTT | 79 | 5-10-5 |
| 361190 | GCCR | GCTTTTCCTAGCTCTTTGAT | 80 | 5-10-5 |
| 361191 | GCCR | ATGGCTTTTCCTAGCTCTTT | 81 | 5-10-5 |
| 361192 | GCCR | ATGGTCTTATCCAAAAATGT | 82 | 5-10-5 |
| 361193 | GCCR | ACTCATGGTCTTATCCAAAA | 83 | 5-10-5 |
| 361194 | GCCR | CAATACTCATGGTCTTATCC | 84 | 5-10-5 |
| 361195 | GCCR | AATTCAATACTCATGGTCTT | 85 | 5-10-5 |
| 361196 | GCCR | ATGATTTCAGCTAACATCTC | 86 | 5-10-5 |
| 180311 | GCCR | GTGATGATTTCAGCTAACAT | 87 | 5-10-5 |
| 361197 | GCCR | GAATATTTTGGTATCTGATT | 88 | 5-10-5 |
| 361198 | GCCR | ATTTGAATATTTTGGTATCT | 89 | 5-10-5 |
| 361199 | GCCR | TTCCATTTGAATATTTTGGT | 90 | 5-10-5 |
| 361200 | GCCR | ATATTTCCATTTGAATATTT | 91 | 5-10-5 |
| 361202 | GCCR | TTTTTGATATTTCCATTTGA | 92 | 5-10-5 |
| 310457 | GCGR | GCACTTTGTGGTGCCAAGGC | 93 | 5-10-5 |
| 325448 | GCGR | GCACTTTGTGGTGCCAAGGC | 93 | 2-16-2 |
| 325568 | GCGR | GCAGTTTGTGGTGCGAAGGC | 93 | 3-14-3 |
| 356171 | GCGR | CCACTTTGTGGTACCAAGGT | 94 | 5-10-5 |
| 357368 | GCGR | GCAGTTTGTGGTACCAAGGT | 94 | Uniform deoxy |
| 357369 | GCGR | GCAGTTTGTGGTACCAAGGT | 94 | 1-18-1 |
| 357370 | GCGR | GCACTTTGTGGTACCAAGGT | 94 | 1-17-2 |
| 357371 | GCGR | GCACTTTGTGGTACCAAGGT | 94 | 2-16-2 |
| 357372 | GCGR | GCACTTTGTGGTACCAAGGT | 94 | 3-14-3 |
| 357373 | GCGR | GCACTTTGTGGTACCAAGGT | 94 | 4-12-4 |
| 217328 | DGAT2 | GCATTGCCACTCCCATTCTT | 95 | 5-10-5 |
| 334177 | DGAT2 | AGGACCCCGGAGTAGGCGGC | 96 | 5-10-5 |
| 366710 | DGAT2 | GACCTATTGAGCCAGGTGAC | 97 | 5-10-5 |
| 366714 | DGAT2 | GTAGCTGCTTTTCCACCTTG | 98 | 5-10-5 |
| 370727 | DGAT2 | AGCTGCTTTTCCACCTTGGA | 99 | 2-16-2 |
| 370747 | DGAT2 | TGGAGCTCAGAGACTCAGCC | 100 | 2-16-2 |
| 370784 | DGAT2 | GCTGCATCCATGTCATCAGC | 101 | 2-16-2 |

TABLE 2

Target sequences

| Target name | Synonyms | Species | GENBANK Accession No or description | SEQ ID NO |
|---|---|---|---|---|
| PTEN | MMAC1; TEP1; TGF beta regulated and epithelial cell-enriched phosphatase; mutated in multiple advanced cancers 1; phosphatase and tensin homologue; putative protein tyrosine phosphatase | mouse | U92437.1 | 103 |
| TRADD | TNF receptor 1 associated protein; TNFRSF1A-associated via death domain; Tumor necrosis factor receptor associated death domain | mouse | consensus sequence built from mouse ESTs: aa013629, aa914725, aa013699, aa122508, aa881900, aa423244, aa930854, w13708, aa201054, ai122320, aa611848, aa546092, and aa939422 | 104 |
| GCCR | nuclear receptor subfamily 3, group C, member 1; GR; GRL; NR3C1; glucocorticoid receptor; nuclear receptor subfamily 3, group C, member 1 | human rat mouse | NM_000176.1 NM_012576.1 NM_008173.1 | 105 106 107 |
| GCGR | glucagon receptor; GR | human rat | NM_000160.1 M96674.1 | 108 109 |
| DGAT2 | ACYL-CoA: DIACYLGLYCEROL ACYLTRANSFERASE 2; diacylglycerol acyltransferase 2; DIACYLGLYCEROL O-ACYLTRANSFERASE 2; GS1999full; LOC84649 | human rat | NM_032564.2 the complement of nucleotides 15333000 to 15365000 of GENBANK ® accession number NW_047561.1 | 110 111 |
| PTP1B | PTP-1B; PTPN1; RKPTP; protein tyrosine phosphatase; protein tyrosine phosphatase 1B; protein tyrosine phosphatase, non-receptor type 1 | human | M31724.1 | 114 |

Example 2

Assaying Modulation of Expression

Modulation of target RNA expression can be assayed in a variety of ways known in the art. GCCR mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., Current Protocols in Molecular Biology, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., Current Protocols in Molecular Biology, Volume 1, pp. 4.2.14.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Levels of proteins encoded by a target RNA can be quantitated in a variety of ways well known in the art, such as immunoprecipitation, Western blot analysis (immunoblotting), ELISA or fluorescence-activated cell sorting (FACS). Antibodies directed to a protein encoded by a target RNA can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., Current Protocols in Molecular Biology, Volume 2, pp. 11.12.1-11.12.9, John Wiley & Sons, Inc., 1997. Preparation of monoclonal antibodies is taught in, for example, Ausubel, F. M. et al., Current Protocols in Molecular Biology, Volume 2, pp. 11.4.1-11.11.5, John Wiley & Sons, Inc., 1997.

Immunoprecipitation methods are standard in the art and can be found at, for example, Ausubel, F. M. et al., Current Protocols in Molecular Biology, Volume 2, pp. 10.16.1-10.16.11, John Wiley & Sons, Inc., 1998. Western blot (immunoblot) analysis is standard in the art and can be found at, for example, Ausubel, F. M. et al., Current Protocols in Molecular Biology, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., Current Protocols in Molecular Biology, Volume 2, pp. 11.2.1-11.2.22, John Wiley & Sons, Inc., 1991.

The effect of oligomeric compounds of the present invention on target nucleic acid expression can be tested in any of a variety of cell types provided that the target nucleic acid is present at measurable levels. The effect of oligomeric compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.), the Japanese Cancer Research Resources Bank (Tokyo, Japan), or the Centre for Applied Microbiology and Research (Wiltshire, United Kingdom).

Primary cells, or those cells which are isolated from an animal and not subjected to continuous culture, can be prepared according to methods known in the art or obtained from various commercial suppliers. Additionally, primary cells include those obtained from donor human subjects in a clinical setting (i.e. blood donors, surgical patients).

Cell Types

The effects of oligomeric compounds on target nucleic acid expression were tested in the following cell types:

b.END Cells:

The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 3000 cells/well for use in oligomeric compound transfection experiments.

HepG2 Cells:

The human hepatoblastoma cell line HepG2 was obtained from the American Type Culture Collection (Manassas, Va.). HepG2 cells were routinely cultured in Eagle's MEM supplemented with 10% fetal bovine serum, 1 mM non-essential amino acids, and 1 mM sodium pyruvate (Invitrogen Life Technologies, Carlsbad, Calif.). Cells were routinely passaged by trypsinization and dilution when they reached approximately 90% confluence. Multiwell culture plates are prepared for cell culture by coating with a 1:100 dilution of type 1 rat tail collagen (BD Biosciences, Bedford, Mass.) in phosphate-buffered saline. The collagen-containing plates were incubated at 37° C. for approximately 1 hour, after which the collagen was removed and the wells were washed twice with phosphate-buffered saline. Cells were seeded into 96-well plates (Falcon-Primaria #353872, BD Biosciences, Bedford, Mass.) at a density of approximately 8,000 cells/well for use in oligomeric compound transfection experiments.

Primary Rat Hepatocytes:

Primary rat hepatocytes are prepared from Sprague-Dawley rats purchased from Charles River Labs (Wilmington, Mass.) and are routinely cultured in DMEM, high glucose (Invitrogen Life Technologies, Carlsbad, Calif.) supplemented with 10% fetal bovine serum (Invitrogen Life Technologies, Carlsbad, Calif.), 100 units per mL penicillin, and 100 µg/mL streptomycin (Invitrogen Life Technologies, Carlsbad, Calif.). Cells are seeded into 96-well plates (Falcon-Primaria #353872, BD Biosciences, Bedford, Mass.) at a density of approximately 4,000-6,000 cells/well treatment with the oligomeric compounds of the invention.

Treatment with Oligomeric Compounds

When cells reached appropriate confluency, they were treated with oligonucleotide using a transfection method as described. Other suitable transfection reagents known in the art include, but are not limited to, LIPOFECTAMINE™, CYTOFECTIN™, OLIGOFECTAMINE™, and FUGENE™. Other suitable transfection methods known in the art include, but are not limited to, electroporation.

LIPOFECTIN™

When cells reach 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture iss incubated at room temperature for approximately 0.5 hours. For cells grown in 96-well plates, wells are washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium. Cells are harvested 16-24 hours after oligonucleotide treatment.

Example 2

Real-Time Quantitative PCR Analysis of GCCR mRNA Levels

Quantitation of GCCR mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Gene target quantities obtained by RT, real-time PCR were normalized using either the expression level of GAPDH, a gene whose expression is constant, or by quantifying total RNA using RiboGreen™ (Molecular Probes, Inc. Eugene; OR). Total RNA was quantified using RiboGreen™ RNA quantification reagent (Molecular Probes, Inc. Eugene, Oreg.). 170 µL of RiboGreen™ working reagent (RiboGreen™ reagent diluted 1:350 in 10 mM Tris-HCl, 1 mM EDTA, pH 7.5) was pipetted into a 96-well plate containing 30 µL purified cellular RNA. The plate was read in a CytoFluor 4000 (PE Applied Biosystems) with excitation at 485 nm and emission at 530 nm.

GAPDH expression was quantified by RT, real-time PCR, either simultaneously with the quantification of the target or separately. For measurement simultaneous with measurement of target levels, primer-probe sets specific to the target gene being measured were evaluated for their ability to be "multiplexed" with a GAPDH amplification reaction prior to quantitative PCR analysis. Multiplexing refers to the detection of multiple DNA species, in this case the target and endogenous GAPDH control, in a single tube, which requires that the primer-probe set for GAPDH does not interfere with amplification of the target.

Probes and primers for use in real-time PCR were designed to hybridize to target-specific sequences. Methods of primer and probe design are known in the art. Design of primers and probes for use in real-time PCR can be carried out using commercially available software, for example Primer Express®, PE Applied Biosystems, Foster City, Calif. The target-specific PCR probes have FAM covalently linked to the 5' end and TAMRA or MGB covalently linked to the 3' end, where FAM is the fluorescent dye and TAMRA or MGB is the quencher dye.

After isolation, the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 µL PCR cocktail (2.5×PCR buffer minus MgCl2, 6.6 mM MgCl2, 375 µM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Example 3

Increased Potency of ISIS 344266 (2-16-2) In Vivo Compared to 5-10-5 Compound is not Due to Enhanced Oligonucleotide Accumulation Mice were dosed with ISIS 116847 (SEQ ID NO: 1) or ISIS 344266 (SEQ ID NO: 1) at 6, 3, 1.5 or 0.75 micromol/kg (approx 40, 20, 10 or 5 mg per kg), twice a week for three weeks and sacrificed 48 hours after the last dose was given. The left panel of FIG. 1 is a graph showing percent reduction of target RNA in liver following administration of saline, ISIS 141923 (negative unrelated control oligonucleotide, incorporated herein as SEQ ID NO: 2), ISIS 116847 at four concentrations, or ISIS 344266 at four concentrations. Both ISIS 116847 and ISIS 344266 are targeted to mouse PTEN (GENBANK® Accession No: U92437.1, herein incorporated as SEQ ID NO: 103), and are cross-species oligonucleotides with perfect complementary to human, rat, and rabbit PTEN. Neither saline nor negative control ISIS 141923 (6 micromoles/kg) reduced PTEN RNA levels. ISIS 116847 reduced PTEN RNA levels by approximately 21%, 44%, 64% and 81% at doses of 0.75, 1.5, 3 and 6 micromol/kg, respectively. ISIS 344266, the gap-widened antisense oligonucleotide, reduced PTEN RNA levels by approximately 54%, 79%, 88% and 91% at doses of 0.75, 1.5, 3 and 6 micromol/kg, respectively. A corresponding reduction of PTEN protein was demonstrated by Western blot as shown in the right panel of FIG. 1.

The ID50 (dose resulting in 50% reduction of PTEN RNA) calculated from these results was 1.9 micromol/kg for 116847 and 0.63 micromol/kg for 344266. The IC50 for ISIS 116847 was also over three-fold that of ISIS 344266. These results indicate that the gap-widened antisense oligonucleotide is three-fold more potent than the 5-10-5 compound of equivalent sequence.

ISIS 344266 (2-16-2) supports similar persistence of action compared to ISIS 116847 (5-10-5). Mice were treated as described above with ISIS 344266 (1.5 or 6 micromol/kg) or ISIS 116847 (6 micromol/kg), or with saline. PTEN RNA levels were measured in mouse liver at days 1, 7, 14 and 28. As shown in FIG. 2, the two compounds show similar durability of reduction of PTEN RNA levels, and even after 28 days the PTEN RNA levels in antisense-treated animals (either 116847 or 344266) had not returned to control levels.

The advantage conveyed by the gap-widened antisense oligonucleotides of the present invention for target reduction in vivo is surprising because it is not observed in vitro. An in vitro comparison of the same PTEN oligonucleotides, ISIS 116847 (5-10-5) and ISIS 344266 (2-16-2) was performed in cultured mouse bEND cells. Cells were transfected with oligonucleotide at doses of 0.1 nM, 0.3 nM, 0.9 nM, 2.7 nM, 8.1 nM and 24.3 nM in the presence of 3 microgram/ml LIPOFECTIN. Reduction of target expression was assayed by quantitative RT real-time PCR as described herein. FIG. 3 shows that the 5-10-5 gapmer was less potent than the 2-16-2 gapmer. The IC50 for reduction of PTEN RNA by the 5-10-5 gapmer (ISIS 116847) was 3.4 nM and 6.2 nM for the 2-16-2 gapmer (ISIS 344266). Thus the advantage conveyed by the gap-widened antisense oligonucleotides for target reduction in liver is not observed in cultured cells.

The enhanced potency of the gap-widened (2-16-2) PTEN antisense oligonucleotide in liver is not due to increased concentrations in liver compared to the 5-10-5 gapmer. Oligonucleotide concentration in kidney and liver tissue from mice treated as described above with ISIS 116847 or ISIS 344266 were determined. Methods to determine oligonucleotide concentration in tissues are known in the art (Geary et al., Anal Biochem, 1999, 274, 241-248). Oligonucleotide concentrations (micrograms/gram) in mouse liver and kidney were determined. As shown in FIG. 4, there was consistently less ISIS 344266 than ISIS 116847 in liver at every oligonucleotide dosage. The same is true for kidney although overall concentrations of both compounds were lower in kidney. Thus, the enhanced potency of the gap-widened antisense oligonucleotide (2-16-2 chimera) in the liver is not due to enhanced accumulation of compound in the liver.

Serum transaminases (AST/ALT) were higher for mice treated with 2-16-2 compound (ISIS 344266) than for those treated with ISIS 116847. However, because ISIS 344266 is more potent (active at lower doses), the therapeutic window for the two compounds is roughly comparable.

Example 3

Effect of Gap Size on In Vitro and In Vivo Potency

A series of MOE gapmers (2-14-2 through 6-6-6) were designed to target mouse TRADD (consensus sequence built from mouse ESTs: aa013629, aa914725, aa013699, aa122508, aa881900, aa423244, aa930854, w13708, aa201054, ai122320, aa611848, aa546092, and aa939422, incoporated herein as SEQ ID NO: 104). As shown in Table 2, a series of 18mer chimeric antisense oligonucleotides were synthesized, all having the same sequence (GCTCATACTCGTAGGCCA, incorporated herein as SEQ ID NO: 3). Plain text indicates a deoxynucleotide, and nucleobases designated with bold, underlined text are 2'-O-(2-methoxyethyl) nucleotides. Internucleoside linkages are phosphorothioate throughout, and all cytosines are 5-methylcytosines. Indicated in Table 2 is the "motif" of each compound indicative of chemically distinct regions comprising the oligonucleotide.

TABLE 2

Antisense oligonucleotides targeting mouse TRADD

| ISIS Number | Chemistry | Motif |
| --- | --- | --- |
| ISIS 325589 | GCTCATACTCGTAGGCCA | 5-8-5 |
| ISIS 117405 | GCTCATACTCGTAGGCCA | 4-10-4 |
| ISIS 325588 | GCTCATACTCGTAGGCCA | 3-12-3 |
| ISIS 325587 | GCTCATACTCGTAGGCCA | 2-14-2 |
| ISIS 325590 | GCTCATACTCGTAGGCCA | 6-6-6 |

The compounds were tested in vitro in mouse bEND cells at concentrations of 0.1 nM, 0.5 nM, 2.5 nM, 12.5 nM and 62.5 nM for their ability to reduce target mRNA levels using real-time PCR as described herein. As shown in FIG. 5, in vitro IC50s for these compounds were 9.2 nM for the 5-8-5 gapmer (ISIS 325589), 11 nM for the 4-10-4 gapmer (ISIS 117405), 19 nM for the 3-12-3 gapmer (ISIS 325588), 49 nM for the 2-14-2 gapmer (ISIS 325587) and 82 nM for the 6-6-6 gapmer (ISIS 325590). Thus in this in vitro experiment, larger gaps did not appear to convey added potency.

When these compounds were tested in vivo, a different rank order potency was observed. Mice were treated with TRADD gapmer oligos (described above) ranging from 2-14-2 chimeras to 6-6-6 chimeras, each at doses of 1.56 micromole/kg, 3.12 micromol/kg and 6.24 micromol/kg. The negative control was ISIS 29837 (SEQ ID NO: 4) and animals treated with saline alone served as the control group to which data were normalized. As shown in FIG. 6, potency in liver increased with increasing gap size (from 6 to 14 contiguous deoxynucleotides). In a subsequent experiment (not shown) the 2-14-2 compound was approximately two-fold better than the 4-10-4 compound.

The effect of these gapmer compounds on mouse body weight, liver weight and spleen weights was compared and no meaningful differences were seen. Mice gained weight at roughly the same rate (indicating general good health) and liver and spleen weights were comparable to saline in all the treatment groups.

Example 4

Antisense Inhibition of Human GCCR Expression by 5-10-5 Gapmers or 2-16-2 Gapmers In Vitro A series of oligomeric compounds was designed to target different regions of human GCCR, using published sequences (GENBANK® accession no: NM_000176.1, incoporated herein as SEQ ID NO: 105). The compounds are shown in Table 3. All compounds in Table 3 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. Shown in Table 3 is the sequence of the oligonucleotide, and the target site which is the first (5' most) position on the target sequence to which the compound binds. The compounds were analyzed for their effect on gene target mRNA levels by quantitative real-time PCR as described in other examples herein, using a primer-probe set designed to hybridize to human GCCR.

Data are averages from three experiments in which HepG2 cells were treated with 50 nM of the disclosed oligomeric compounds using LIPOFECTIN™. A reduction in expression is expressed as percent inhibition in Table 3. If present, "N.D." indicates "not determined". The target regions to which these oligomeric compounds are inhibitory are herein referred to as "validated target segments."

TABLE 3

Inhibition of human GCCR mRNA levels by 5-10-5 gapmers

| ISIS No of 5-10-5 | Target SEQ ID NO | Target Site | Sequence | % Inhib w/5-10-5 | SEQ ID NO |
|---|---|---|---|---|---|
| 361132 | 105 | 394 | TCTGTCTCTCCCATATACAG | 65 | 5 |
| 361133 | 105 | 398 | TGTTTCTGTCTCTCCCATAT | 56 | 6 |
| 361134 | 105 | 402 | CTTTTGTTTCTGTCTCTCCC | 60 | 7 |
| 361135 | 105 | 406 | ATCACTTTTGTTTCTGTCTC | 80 | 8 |
| 180272 | 105 | 497 | GTTTGCAATGCTTTCTTCCA | 74 | 9 |
| 345188 | 105 | 501 | TGAGGTTTGCAATGCTTTCT | 71 | 10 |
| 361136 | 105 | 505 | CTATTGAGGTTTGCAATGCT | 10 | 11 |
| 361137 | 105 | 509 | CGACCTATTGAGGTTTGCAA | 80 | 12 |
| 180274 | 105 | 514 | CTGGTCGACCTATTGAGGTT | 68 | 13 |
| 180275 | 105 | 672 | CTGTGGTATACAATTTCACA | 44 | 14 |
| 180276 | 105 | 679 | CTTTGGTCTGTGGTATACAA | 78 | 15 |
| 345198 | 105 | 689 | GTCAAAGGTGCTTTGGTCTG | 79 | 16 |
| 180279 | 105 | 877 | GGTTTAGTGTCCGGTAAAAT | 60 | 17 |
| 361138 | 105 | 954 | CTTTTCTGTTTTCACTTGG | 70 | 18 |
| 180280 | 105 | 1000 | TTCTCTTGCTTAATTACCCC | 77 | 19 |
| 345218 | 105 | 1004 | CAGTTTCTCTTGCTTAATTA | 67 | 20 |
| 180281 | 105 | 1007 | GCCCAGTTTCTCTTGCTTAA | 74 | 21 |
| 361139 | 105 | 1058 | TTTATTACCAATTATATTTG | 0 | 22 |
| 361140 | 105 | 1062 | ACATTTTATTACCAATTATA | 35 | 23 |
| 361141 | 105 | 1066 | GCAGACATTTTATTACCAAT | 78 | 24 |
| 361142 | 105 | 1070 | AATGGCAGACATTTTATTAC | 40 | 25 |
| 361143 | 105 | 1074 | CAGAAATGGCAGACATTTTA | 63 | 26 |
| 361144 | 105 | 1078 | TGAACAGAAATGGCAGACAT | 61 | 27 |
| 180283 | 105 | 1081 | CCATGAACAGAAATGGCAGA | 69 | 28 |
| 361145 | 105 | 1085 | CACACCATGAACAGAAATGG | 30 | 29 |

TABLE 3-continued

Inhibition of human GCCR mRNA levels by 5-10-5 gapmers

| ISIS No of 5-10-5 | Target SEQ ID NO | Target Site | Sequence | % Inhib w/5-10-5 | SEQ ID NO |
|---|---|---|---|---|---|
| 361146 | 105 | 1089 | TACTCACACCATGAACAGAA | 60 | 30 |
| 361147 | 105 | 1093 | GAGGTACTCACACCATGAAC | 71 | 31 |
| 361148 | 105 | 1097 | TCCAGAGGTACTCACACCAT | 75 | 32 |
| 361149 | 105 | 1101 | GTCCTCCAGAGGTACTCACA | 69 | 33 |
| 361150 | 105 | 1105 | ATCTGTCCTCCAGAGGTACT | 53 | 34 |
| 361151 | 105 | 1109 | GTACATCTGTCCTCCAGAGG | 75 | 35 |
| 361152 | 105 | 1113 | AGTGGTACATCTGTCCTCCA | 62 | 36 |
| 361153 | 105 | 1117 | TCATAGTGGTACATCTGTCC | 52 | 37 |
| 361154 | 105 | 1121 | CATGTCATAGTGGTACATCT | 57 | 38 |
| 361155 | 105 | 1125 | TATTCATGTCATAGTGGTAC | 41 | 39 |
| 361156 | 105 | 1129 | GCTGTATTCATGTCATAGTG | 67 | 40 |
| 361157 | 105 | 1133 | GGATGCTGTATTCATGTCAT | 67 | 41 |
| 361158 | 105 | 1137 | AAAGGGATGCTGTATTCATG | 45 | 42 |
| 180288 | 105 | 1141 | TGAGAAAGGGATGCTGTATT | 62 | 43 |
| 180289 | 105 | 1181 | TGGTGGAATGACATTAAAAA | 54 | 44 |
| 361159 | 105 | 1185 | GAATTGGTGGAATGACATTA | 24 | 45 |
| 361160 | 105 | 1324 | GAGCTTACATCTGGTCTCAT | 59 | 46 |
| 361161 | 105 | 1328 | AGGAGAGCTTACATCTGGTC | 65 | 47 |
| 361162 | 105 | 1332 | ATGGAGGAGAGCTTACATCT | 18 | 48 |
| 361163 | 105 | 1336 | CTGGATGGAGGAGAGCTTAC | 50 | 49 |
| 361164 | 105 | 1339 | GAGCTGGATGGAGGAGAGCT | 49 | 50 |
| 361165 | 105 | 1468 | TGTCCTTCCACTGCTCTTTT | 61 | 51 |
| 361166 | 105 | 1472 | GTGCTGTCCTTCCACTGCTC | 65 | 52 |
| 361167 | 105 | 1476 | AATTGTGCTGTCCTTCCACT | 62 | 53 |
| 361168 | 105 | 1480 | AGGTAATTGTGCTGTCCTTC | 52 | 54 |
| 361169 | 105 | 1543 | CGGCATGCTGGGCAGTTTTT | 78 | 55 |
| 361170 | 105 | 1547 | ATAGCGGCATGCTGGGCAGT | 58 | 56 |
| 361171 | 105 | 1549 | CGATAGCGGCATGCTGGGCA | 65 | 57 |
| 361172 | 105 | 1570 | ATTCCAGCCTGAAGACATTT | 24 | 58 |
| 361173 | 105 | 1574 | GTTCATTCCAGCCTGAAGAC | 52 | 59 |
| 361174 | 105 | 1597 | TTCTTTGTTTTTCGAGCTTC | 62 | 60 |
| 361175 | 105 | 1601 | TTTTTTCTTTGTTTTTCGAG | 48 | 61 |
| 180297 | 105 | 1680 | CAGGAACTATTGTTTTGTTA | 33 | 62 |
| 361176 | 105 | 1682 | TGCAGGAACTATTGTTTTGT | 46 | 63 |
| 361177 | 105 | 1765 | GAGCTATCATATCCTGCATA | 71 | 64 |
| 361178 | 105 | 1769 | AACAGAGCTATCATATCCTG | 51 | 65 |
| 361179 | 105 | 1773 | CTGGAACAGAGCTATCATAT | 67 | 66 |

TABLE 3-continued

Inhibition of human GCCR mRNA levels by 5-10-5 gapmers

| ISIS No of 5-10-5 | Target SEQ ID NO | Target Site | Sequence | % Inhib w/5-10-5 | SEQ ID NO |
|---|---|---|---|---|---|
| 361180 | 105 | 1840 | TTCACTGCTGCAATCACTTG | 52 | 67 |
| 361181 | 105 | 1844 | CCATTTCACTGCTGCAATCA | 55 | 68 |
| 361182 | 105 | 1848 | TTGCCCATTTCACTGCTGCA | 70 | 69 |
| 361183 | 105 | 1999 | ATAATCAGATCAGGAGCAAA | 36 | 70 |
| 361184 | 105 | 2003 | ATTAATAATCAGATCAGGAG | 10 | 71 |
| 361185 | 105 | 2007 | GCTCATTAATAATCAGATCA | 43 | 72 |
| 361186 | 105 | 2011 | CTCTGCTCATTAATAATCAG | 0 | 73 |
| 180302 | 105 | 2015 | CATTCTCTGCTCATTAATAA | 23 | 74 |
| 180304 | 105 | 2053 | AGCATGTGTTTACATTGGTC | 73 | 75 |
| 361187 | 105 | 2119 | AAGGTTTTCATACAGAGATA | 38 | 76 |
| 361188 | 105 | 2123 | CAGTAAGGTTTTCATACAGA | 22 | 77 |
| 361189 | 105 | 2127 | GAAGCAGTAAGGTTTTGATA | 46 | 78 |
| 180307 | 105 | 2131 | GAGAGAAGCAGTAAGGTTTT | 32 | 79 |
| 361190 | 105 | 2212 | GCTTTTCCTAGCTCTTTGAT | 74 | 80 |
| 361191 | 105 | 2215 | ATGGCTTTTCCTAGCTCTTT | 68 | 81 |
| 361192 | 105 | 2347 | ATGGTCTTATCCAAAAATGT | 63 | 82 |
| 361193 | 105 | 2351 | ACTCATGGTCTTATCGAAAA | 66 | 83 |
| 361194 | 105 | 2355 | CAATACTCATGGTCTTATCC | 54 | 84 |
| 361195 | 105 | 2359 | AATTCAATACTCATGGTCTT | 69 | 85 |
| 361196 | 105 | 2383 | ATGATTTCAGCTAACATCTC | 1 | 86 |
| 180311 | 105 | 2386 | GTGATGATTTCAGCTAACAT | 59 | 87 |
| 361197 | 105 | 2407 | GAATATTTTGGTATCTGATT | 59 | 88 |
| 361198 | 105 | 2411 | ATTTGAATATTTTGGTATCT | 20 | 89 |
| 361199 | 105 | 2415 | TTCCATTTGAATATTTTGGT | 65 | 90 |
| 361200 | 105 | 2419 | ATATTCCATTTGAATATTT | 51 | 91 |
| 361202 | 105 | 2425 | TTTTTGATATTTCCATTTGA | 20 | 92 |

Gap-widened oligonucleotides having the same sequences as the compounds described in Table 4 were also tested. All compounds in Table 4 are chimeric oligonucleotides ("gapmers") 20 nucleotides in length, composed of a central "gap" region consisting of 16 2'-deoxynucleotides, which is flanked on both sides (5' and 3') by two-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. Shown in Table 4 is the sequence of the oligonucleotide, and the target site which is the first (5' most) position on the target sequence to which the compound binds. The 2-16-2 motif compounds were analyzed for their effect on gene target mRNA levels by quantitative real-time PCR as described herein.

Data are averages from three experiments in which HepG2 cells were treated with 50 nM of the disclosed oligomeric compounds using LIPOFECTIN™. A reduction in expression is expressed as percent inhibition in Table 4. If present, "N.D." indicates "not determined". The target regions to which these oligomeric compounds are inhibitory are herein referred to as "validated target segments."

TABLE 4

Inhibition of human GCCR mRNA levels by 2-16-2 gapmers

| ISIS No of 2-16-2 | Target SEQ ID NO | Target Site | Sequence | % Inhib w/2-16-2 | SEQ ID NO |
|---|---|---|---|---|---|
| 372350 | 105 | 394 | TCTGTCTCTCCCATATACAG | 69 | 5 |
| 372376 | 105 | 398 | TGTTTCTGTGTCTCCCATAT | 72 | 6 |
| 372331 | 105 | 402 | CTTTTGTTTCTGTCTCTCCC | 67 | 7 |
| 372341 | 105 | 406 | ATCACTTTTGTTTCTGTCTC | 63 | 8 |
| 352983 | 105 | 497 | GTTTGCAATGCTTTCTTCCA | 64 | 9 |
| 372365 | 105 | 501 | TGAGGTTTGCAATGCTTTCT | 69 | 10 |
| 372387 | 105 | 505 | CTATTGAGGTTTGCAATGCT | 70 | 11 |
| 372316 | 105 | 509 | CGACCTATTGAGGTTTGCAA | 73 | 12 |
| 372310 | 105 | 514 | CTGGTCGACCTATTGAGGTT | 70 | 13 |
| 372315 | 105 | 672 | CTGTGGTATACAATTTCACA | 35 | 14 |
| 372326 | 105 | 679 | CTTTGGTCTGTGGTATACAA | 54 | 15 |
| 372339 | 105 | 689 | GTCAAAGGTGCTTTGGTCTG | 81 | 16 |
| 372322 | 105 | 877 | GGTTTAGTGTCCGGTAAAAT | 78 | 17 |
| 372361 | 105 | 954 | CTTTTTCTGTTTTCACTTGG | 70 | 18 |
| 372308 | 105 | 1000 | TTCTCTTGCTTAATTACCCC | 84 | 19 |
| 372304 | 105 | 1004 | CAGTTTCTCTTGCTTAATTA | 66 | 20 |
| 352984 | 105 | 1007 | GCCCAGTTTCTCTTGCTTAA | 80 | 21 |
| 372372 | 105 | 1058 | TTTATTACCAATTATATTTG | 0 | 22 |
| 372327 | 105 | 1062 | ACATTTTATTACCAATTATA | 11 | 23 |
| 372311 | 105 | 1066 | GCAGACATTTTATTACCAAT | 65 | 24 |
| 372352 | 105 | 1070 | AATGGCAGACATTTTATTAC | 54 | 25 |
| 372337 | 105 | 1074 | CAGAAATGGCAGACATTTTA | 36 | 26 |
| 372323 | 105 | 1078 | TGAACAGAAATGGCAGACAT | 73 | 27 |
| 372347 | 105 | 1081 | CCATGAACAGAAATGGCAGA | 86 | 28 |
| 372383 | 105 | 1085 | CACACCATGAACAGAAATGG | 73 | 29 |
| 372348 | 105 | 1089 | TACTCACACCATGAACAGAA | 82 | 30 |
| 372363 | 105 | 1093 | GAGGTACTCACACCATGAAC | 47 | 31 |
| 372334 | 105 | 1097 | TCCAGAGGTACTCACACCAT | 82 | 32 |
| 372359 | 105 | 1101 | GTCCTCCAGAGGTACTCACA | 69 | 33 |
| 372344 | 105 | 1105 | ATCTGTCCTCCAGAGGTACT | 72 | 34 |
| 372307 | 105 | 1109 | GTACATGTGTCCTCCAGAGG | 74 | 35 |
| 372370 | 105 | 1113 | AGTGGTACATCTGTCCTCCA | 69 | 36 |
| 372374 | 105 | 1117 | TCATAGTGGTACATCTGTCC | 0 | 37 |
| 372355 | 105 | 1121 | CATGTCATAGTGGTACATCT | 65 | 38 |
| 372385 | 105 | 1125 | TATTCATGTCATAGTGGTAC | 18 | 39 |
| 372319 | 105 | 1129 | GGTGTATTCATGTCATAGTG | 23 | 40 |
| 372366 | 105 | 1133 | GGATGCTGTATTCATGTCAT | 37 | 41 |
| 372330 | 105 | 1137 | AAAGGGATGCTGTATTCATG | 80 | 42 |
| 372333 | 105 | 1141 | TGAGAAAGGGATGCTGTATT | 68 | 43 |
| 372358 | 105 | 1181 | TGGTGGAATGACATTAAAAA | 67 | 44 |
| 372381 | 105 | 1185 | GAATTGGTGGAATGACATTA | 30 | 45 |
| 372377 | 105 | 1324 | GAGCTTACATCTGGTCTCAT | 45 | 46 |
| 372309 | 105 | 1328 | AGGAGAGCTTACATCTGGTC | 63 | 47 |
| 372388 | 105 | 1332 | ATGGAGGAGAGCTTACATCT | 55 | 48 |
| 372321 | 105 | 1336 | CTGGATGGAGGAGAGCTTAC | 51 | 49 |
| 372312 | 105 | 1339 | GAGCTGGATGGAGGAGAGGT | 60 | 50 |
| 372324 | 105 | 1468 | TGTCCTTCCACTGCTCTTTT | 73 | 51 |
| 372332 | 105 | 1472 | GTGCTGTCCTTCCACTGCTC | 81 | 52 |
| 372335 | 105 | 1476 | AATTGTGCTGTCCTTCCACT | 42 | 53 |
| 372342 | 105 | 1480 | AGGTAATTGTGCTGTCCTTC | 100 | 54 |
| 372345 | 105 | 1543 | CGGCATGCTGGGCAGTTTTT | 82 | 55 |
| 372356 | 105 | 1547 | ATAGCGGCATGCTGGGCAGT | 73 | 56 |
| 372305 | 105 | 1549 | CGATAGCGGCATGCTGGGCA | 80 | 57 |
| 372367 | 105 | 1570 | ATTCCAGCCTGAAGACATTT | 78 | 58 |
| 372353 | 105 | 1574 | GTTCATTCCAGCCTGAAGAC | 70 | 59 |
| 372364 | 105 | 1597 | TTCTTTGTTTTTCGAGCTTC | 47 | 60 |
| 372340 | 105 | 1601 | TTTTTTCTTTGTTTTTGGAG | 100 | 61 |
| 372369 | 105 | 1680 | CAGGAACTATTGTTTTGTTA | 56 | 62 |
| 372378 | 105 | 1682 | TGCAGGAACTATTGTTTTGT | 41 | 63 |
| 372317 | 105 | 1765 | GAGCTATCATATCCTGCATA | 84 | 64 |
| 372351 | 105 | 1769 | AACAGAGCTATCATATCCTG | 69 | 65 |
| 372389 | 105 | 1773 | CTGGAACAGAGCTATCATAT | 76 | 66 |
| 372362 | 105 | 1840 | TTCACTGCTGCAATCACTTG | 64 | 67 |
| 372328 | 105 | 1844 | CCATTTCACTGCTGCAATCA | 81 | 68 |
| 372338 | 105 | 1848 | TTGCCCATTTCACTGCTGCA | 82 | 69 |
| 372349 | 105 | 1999 | ATAATCAGATCAGGAGCAAA | 10 | 70 |
| 372373 | 105 | 2003 | ATTAATAATCAGATCAGGAG | 30 | 71 |
| 372360 | 105 | 2007 | GCTCATTAATAATCAGATCA | 27 | 72 |
| 372384 | 105 | 2011 | CTCTGCTGATTAATAATCAG | 100 | 73 |
| 372380 | 105 | 2015 | CATTCTCTGCTCATTAATAA | 2 | 74 |
| 372320 | 105 | 2053 | AGCATGTGTTTACATTGGTC | 75 | 75 |
| 372371 | 105 | 2119 | AAGGTTTTCATACAGAGATA | 37 | 76 |
| 372382 | 105 | 2123 | CAGTAAGGTTTTCATACAGA | 44 | 77 |

TABLE 4-continued

Inhibition of human GCCR mRNA levels by 2-16-2 gapmers

| ISIS No of 2-16-2 | Target SEQ ID NO | Target Site | Sequence | % Inhib w/2-16-2 | SEQ ID NO |
|---|---|---|---|---|---|
| 372306 | 105 | 2127 | GAAGGAGTAAGGTTTTCATA | 48 | 78 |
| 372343 | 105 | 2131 | GAGAGAAGCAGTAAGGTTTT | 46 | 79 |
| 372313 | 105 | 2212 | GCTTTTCCTAGCTCTTTGAT | 66 | 80 |
| 372325 | 105 | 2215 | ATGGCTTTTCCTAGCTCTTT | 69 | 81 |
| 372336 | 105 | 2347 | ATGGTCTTATCCAAAAATGT | 65 | 82 |
| 372318 | 105 | 2351 | ACTCATGGTCTTATCCAAAA | 70 | 83 |
| 372375 | 105 | 2355 | CAATACTCATGGTCTTATCC | 85 | 84 |
| 372346 | 105 | 2359 | AATTCAATACTCATGGTCTT | 47 | 85 |
| 372386 | 105 | 2383 | ATGATTTCAGCTAACATCTC | 74 | 86 |
| 372354 | 105 | 2386 | GTGATGATTTCAGCTAACAT | 66 | 87 |
| 372357 | 105 | 2407 | GAATATTTTGGTATCTGATT | 13 | 88 |
| 372368 | 105 | 2411 | ATTTGAATATTTTGGTATCT | 0 | 89 |
| 372379 | 105 | 2415 | TTCCATTTGAATATTTTGGT | 44 | 90 |
| 372390 | 105 | 2419 | ATATTTCCATTTGAATATTT | 0 | 91 |
| 372329 | 105 | 2425 | TTTTTGATATTTCCATTTGA | 0 | 92 |

The 2-16-2 oligonucleotides shown in Table 4 and the 5-10-5 oligonucleotides shown in Table 3 which reduced GCCR expression by at least 30% are preferred. The target segments to which these preferred sequences are complementary are herein referred to as "preferred target segments" and are therefore preferred for targeting by compounds of the present invention.

Example 5

Cross-Species Oligonucleotides Targeting GCCR

Some oligonucleotides described in the previous example are complementary across species and are therefore expected to reduce expression of glucocorticoid receptor across species. Shown in Table 5 is the sequence of such cross-species oligonucleotides, and the ISIS numbers of the 5-10-5 motif version and the 2-16-2 motif version of the oligonucleotide. Also indicated for each sequence is the target site which is the first (5' most) position on the human target sequence (NM_000176.1, incorporated herein as SEQ ID NO: 105) to which the compound binds. The complementarity for human, cynomolgus monkey, rat, and mouse GCCR mRNA is indicated ("yes" means perfect complementarity and "1 mm" means one mismatch from perfect complementarity).

TABLE 5

Cross-species oligonucleotides targeted to GCCR

| ISIS # of 5-10-5 gapmer | ISIS # of 2-16-2 gapmer | SEQ ID NO | Sequence | Pos'n on SEQ ID NO: 1 | Perfect complement to: | | | |
|---|---|---|---|---|---|---|---|---|
| | | | | | Human | Monkey | Rat | Mouse |
| 361137 | 372316 | 12 | cgacctattgaggtttgcaa | 509 | yes | yes | yes | yes |
| 180276 | 372326 | 15 | ctttggtctgtggtatacaa | 679 | yes | 1 mm | 1 mm | yes |
| 345198 | 372339 | 16 | gtcaaaggtgctttggtctg | 689 | yes | yes | yes | yes |
| 180304 | 372320 | 75 | agcatgtgtttacattggtc | 2053 | yes | yes | yes | yes |
| 180275 | 372315 | 14 | ctgtggtatacaatttcaca | 672 | yes | 1 mm | 1 mm | yes |
| 361141 | 372311 | 24 | gcagacattttattaccaat | 1066 | yes | yes | yes | 1 mm |
| 180281 | 352984 | 21 | gcccagtttctcttgcttaa | 1007 | yes | yes | yes | yes |
| 361151 | 372307 | 35 | gtacatctgtcctccagagg | 1109 | yes | yes | yes | yes |
| 180274 | 372310 | 13 | ctggtcgacctattgaggtt | 514 | yes | yes | yes | yes |
| 361156 | 372319 | 40 | gctgtattcatgtcatagtg | 1129 | yes | yes | yes | yes |

Example 6

Antisense Inhibition of Human and Rat GCCR mRNA Level—Dose-Response Studies with 5-10-5 Gapmers In a further embodiment of the present invention, eleven oligonucleotides were selected for additional dose-response studies. Primary rat hepatocytes were treated with 5, 10, 25, 50, 100 or 200 nM of ISIS 180274, ISIS 180275, ISIS 180276, ISIS 180281, ISIS 180304, ISIS 361137, ISIS 361141, ISIS 361151, ISIS 361156, ISIS 345198, ISIS 361137 or the negative control oligonucleotide ISIS 141923 (CCTTCCCTGAAGGTTCCTCC, incorporated herein as SEQ ID NO: 2), and mRNA levels were measured as described in other examples herein. ISIS 141923 is a 5-10-5 gapmer comprising a ten deoxynucleotide gap flanked by 2'-MOE wings and a phosphorothioate backbone. All cytosines are 5-methylcytosines. Untreated cells served as the control to which the data were normalized.

Results of these studies are shown in Table 6. Target mRNA levels were measured by real-time PCR as described herein. Data are averages from three experiments and are expressed as percent inhibition relative to untreated control.

TABLE 6

Dose-dependent inhibition of GCCR expression in rat primary hepatocytes

| ISIS # | SEQ ID NO | % Inhibition Dose of Oligonucleotide (nM) | | | | | |
|---|---|---|---|---|---|---|---|
| | | 5 | 10 | 25 | 50 | 100 | 200 |
| 180274 | 13 | 16 | 33 | 29 | 65 | 84 | 89 |
| 180275 | 14 | 0 | 13 | 56 | 84 | 84 | 90 |
| 180276 | 15 | 23 | 43 | 43 | 68 | 89 | 93 |
| 180281 | 21 | 0 | 20 | 33 | 75 | 86 | 87 |
| 180304 | 75 | 42 | 51 | 47 | 75 | 86 | 91 |
| 361137 | 12 | 40 | 30 | 48 | 81 | 83 | 89 |
| 361141 | 24 | 36 | 61 | 48 | 77 | 87 | 92 |
| 361151 | 35 | 10 | 28 | 42 | 77 | 90 | 94 |
| 361156 | 40 | 22 | 47 | 46 | 66 | 84 | 92 |
| 345198 | 16 | 0 | 35 | 53 | 81 | 77 | 85 |
| 361158 | 42 | 34 | 50 | 47 | 79 | 91 | 93 |
| 141923 | 2 | 0 | 10 | 18 | 43 | 0 | 12 |

In a further embodiment of the present invention, the same oligonucleotides were tested in the human HepG2 cell line for their ability to reduce GCCR mRNA expression at the indicated doses. Untreated cells served as the control to which the data were normalized.

Results of these studies are shown in Table 7. Target mRNA levels were measured by real-time PCR as described herein. Data are averages from three experiments and are expressed as percent inhibition relative to untreated control.

TABLE 7

Dose-dependent inhibition of GCCR expression in HepG2 cells

| ISIS # | SEQ ID NO | % Inhibition Dose of Oligonucleotide (nM) | | | | | |
|---|---|---|---|---|---|---|---|
| | | 1 | 10 | 25 | 50 | 100 | 200 |
| 180274 | 13 | 0 | 31 | 54 | 66 | 77 | 83 |
| 180275 | 14 | 13 | 54 | 75 | 86 | 93 | 94 |
| 180276 | 15 | 26 | 77 | 87 | 92 | 94 | 98 |
| 180281 | 21 | 3 | 46 | 68 | 80 | 90 | 84 |
| 180304 | 75 | 0 | 64 | 90 | 90 | 92 | 91 |
| 361137 | 12 | 18 | 71 | 84 | 91 | 92 | 86 |
| 361141 | 24 | 1 | 49 | 81 | 85 | 73 | 78 |
| 361151 | 35 | 22 | 42 | 71 | 82 | 89 | 91 |
| 361156 | 40 | 7 | 75 | 75 | 79 | 80 | 82 |
| 345198 | 16 | 17 | 71 | 79 | 86 | 80 | 82 |
| 361158 | 42 | 11 | 35 | 78 | 80 | 82 | 77 |
| 141923 | 2 | 15 | 12 | 20 | 12 | 14 | 3 |

As shown in Table 6 and Table 7, antisense oligonucleotides targeting GCCR are effective at reducing both human and rat target mRNA levels in a dose-dependent manner in vitro.

Example 7

Antisense Inhibition of Rat GCCR mRNA Levels—In Vivo Dose-Response Studies with 5-10-5 Gapmers Five of the 5-10-5 gapmer motif oligonucleotides (ISIS 180281, ISIS 361137, ISIS 345198, ISIS 180304, and ISIS 361141) were evaluated at various doses in rats for their ability to reduce GCCR mRNA levels in liver. Eight week-old Sprague Dawley rats were divided into treatment groups which received doses of 50, 25 or 12.5 mg/kg of one the indicated oligonucleotides via injection. Each treatment group was comprised of four animals, and was dosed twice weekly for 3 weeks. Animals injected with saline alone served as a control group. The animals were evaluated weekly for standard blood parameters (ALT/AST, cholesterol, triglycerides, and glucose). Animals were sacrificed at the end of the study and liver tissue was collected and analyzed for target reduction using real-time PCR analysis methods described herein. Results are shown in Tables 8a and 8b (separate experiments) as the percentage reduction in GCCR mRNA measured after treatment with the indicated doses of the indicated oligonucleotides.

TABLE 8a

In vivo rat screen-GCCR antisense oligonucleotides

| Compound | % Reduction in GCCR mRNA in rat liver (compared to saline-treated controls) | | |
|---|---|---|---|
| | 50 mg/kg | 25 mg/kg | 12.5 mg/kg |
| ISIS 180281 | 68 | 65 | 48 |
| ISIS 180304 | 52 | 34 | 0 |
| ISIS 345198 | 63 | 58 | 52 |

TABLE 8b

In vivo rat screen-GCCR antisense oligonucleotides

| Compound | % Reduction in GCCR mRNA in rat liver (compared to saline-treated controls) | | |
|---|---|---|---|
| | 50 mg/kg | 25 mg/kg | 12.5 mg/kg |
| ISIS 180281 | 62 | 62 | 59 |
| ISIS 361137 | 59 | 47 | 32 |
| ISIS 361141 | 61 | 49 | 22 |

The data in Tables 8a and 8b show that antisense oligonucleotides targeted to GCCR are effective at reducing expression in vivo in a dose-dependent manner. ISIS 345198 (GTCAAAGGTGCTTTGGTCTG; SEQ ID NO: 16) was chosen for further evaluation in structure-activity experiments focusing on gap optimization. This compound is perfectly complementary to mouse, rat, human, monkey, rabbit and guinea pig glucocorticoid receptor RNA.

Example 8

Antisense Inhibition of GCCR mRNA Levels In Vivo—Gap Optimization Study

A series of oligomeric compounds were designed to target GCCR with varying sizes of the deoxynucleotide gap and 2'-MOE wings. Each of the oligonucleotides tested has the same nucleobase sequence (GTCAAAGGTGCTTTG-GTCTG, incorporated herein as SEQ ID NO: 16) and therefore targets the same segment of SEQ ID NO: 105 (nucleobases 689 to 709). As shown in Example 5, this oligonucleotide is also perfectly complementary to rat GCCR.

The compounds are shown in Table 9. Plain text indicates a deoxynucleotide, and nucleobases designated with bold, underlined text are 2'-O-(2-methoxyethyl) nucleotides. Internucleoside linkages are phosphorothioate throughout, and all cytosines are 5-methylcytosines. Indicated in Table 9 is the "motif" of each compound indicative of chemically distinct regions comprising the oligonucleotide.

TABLE 9

Antisense compounds targeting rat GCCR

| ISIS Number | Chemistry | Motif |
|---|---|---|
| 345198 | GTCAAAGGTGCTTTGGTCTG | 5-10-5 gapmer |
| 372339 | GTCAAAGGTGCTTTGGTCTG | 2-16-2 gapmer |
| 377130 | GTCAAAGGTGCTTTGGTCTG | 3-14-3 gapmer |
| 377131 | GTCAAAGGTGCTTTGGTCTG | 4-12-4 gapmer |

Nine-week old Sprague-Dawley male rats were treated twice weekly for three weeks with doses of 50, 25, 12.5, and 6.25 mg/kg of the oligonucleotides presented in Table 9. Animals injected with saline alone served as controls. Each treatment group was comprised of four animals.

At the end of the study, animals were sacrificed, and tissues were collected for determination of target reduction and oligonucleotide concentration.

White adipose tissue was analyzed for target reduction using real-time PCR analysis methods described herein. Results are shown in Tables 10a, 10b, and 10c (separate experiments) as the percentage reduction in GCCR mRNA measured after treatment with the indicated doses of the indicated oligonucleotides. Tissues from animals treated with each gap-widened oligonucleotide were assayed for target reduction alongside tissues from animals treated with the 5-10-5 motif oligonucleotide for comparison.

TABLE 10a

In vivo reduction of GCCR levels in white adipose tissue with 2-16-2 oligonucleotides

| Treatment group | % Inhibition Dose of oligonucleotide (mg/kg) | | | |
|---|---|---|---|---|
| | 50 | 25 | 12.5 | 6.25 |
| ISIS 345198 | 56 | 26 | 17 | 7 |
| ISIS 372339 | 34 | 0 | 8 | 8 |

TABLE 10b

In vivo reduction of GCCR levels in white adipose tissue with 3-14-3 oligonucleotides

| Treatment group | % Inhibition Dose of oligonucleotide (mg/kg) | | | |
|---|---|---|---|---|
| | 50 | 25 | 12.5 | 6.25 |
| ISIS 345198 | 59 | 49 | 27 | 22 |
| ISIS 377130 | 54 | 37 | 21 | 18 |

TABLE 10c

In vivo reduction of GCCR levels in white adipose tissue with 4-12-4 oligonucleotides

| Treatment group | % Inhibition Dose of oligonucleotide (mg/kg) | | | |
|---|---|---|---|---|
| | 50 | 25 | 12.5 | 6.25 |
| ISIS 345198 | 56 | 23 | 21 | 7 |
| ISIS 377131 | 55 | 23 | 15 | 0 |

Liver tissue was also analyzed for target reduction using real-time PCR analysis methods described herein. Results are shown in Tables 11a, 11b, and 11c (separate experiments) as the percentage reduction in GCCR mRNA measured after treatment with the indicated doses of the indicated oligonucleotides. Tissues from animals treated with each gap-widened oligonucleotide were assayed for target reduction alongside tissues from animals treated with the 5-10-5 motif oligonucleotide for comparison.

TABLE 11a

In vivo reduction of GCCR levels in liver with 2-16-2 oligonucleotides

| Treatment group | % Inhibition Dose of oligonucleotide (mg/kg) | | | |
|---|---|---|---|---|
| | 50 | 25 | 12.5 | 6.25 |
| ISIS 345198 | 78 | 77 | 65 | 51 |
| ISIS 372339 | 83 | 77 | 56 | 44 |

TABLE 11b

In vivo reduction of GCCR levels in liver with 3-14-3 oligonucleotides

| Treatment group | % Inhibition Dose of oligonucleotide (mg/kg) | | | |
|---|---|---|---|---|
| | 50 | 25 | 12.5 | 6.25 |
| ISIS 345198 | 78 | 80 | 67 | 54 |
| ISIS 377130 | 87 | 78 | 68 | 43 |

TABLE 11c

In vivo reduction of GCCR levels in liver with 4-12-4 oligonucleotides

| Treatment group | % Inhibition Dose of oligonucleotide (mg/kg) | | | |
|---|---|---|---|---|
| | 50 | 25 | 12.5 | 6.25 |
| ISIS 345198 | 76 | 75 | 58 | 49 |
| ISIS 377131 | 82 | 64 | 60 | 61 |

As shown in Tables 11a, 11b, and 11c, all of the gap-widened oligonucleotides tested were effective at reducing GCCR levels in a dose-dependent manner in vivo. In addition, the gap-widened oligonucleotides show a trend toward greater potency than the 5-10-5 gapmer in the liver.

In addition, to determine effects of altering the gap size on pharmacokinetics, oligonucleotide concentration in kidney and liver were determined. Methods to determine oligonucleotide concentration in tissues are known in the art (Geary et al., *Anal Biochem*, 1999, 274, 241-248). Total oligonucleotide is the sum of all oligonucleotides metabolites detected in the tissue. Shown in Table 12 are the total concentration and the concentration of full length oligonucleotide (in µg/g) in the liver of animals treated with the indicated oligonucleotide at the indicated concentration.

TABLE 12

GCCR oligonucleotide concentration in rat liver

| Treatment | Motif | Dose | Liver Total oligo | Liver Full-length |
|---|---|---|---|---|
| ISIS 345198 | 5-10-5 | 25 mg/kg | 507 | 408 |
|  |  | 12.5 mg/kg | 318 | 224 |
| ISIS 372339 | 2-16-2 | 25 mg/kg | 450 | 306 |
|  |  | 12.5 mg/kg | 311 | 183 |
| ISIS 377130 | 3-14-3 | 25 mg/kg | 575 | 315 |
|  |  | 12.5 mg/kg | 350 | 212 |
| ISIS 377131 | 4-12-4 | 25 mg/kg | 584 | 424 |
|  |  | 12.5 mg/kg | 354 | 265 |

As shown in Table 12, the levels of full-length oligonucleotide in the liver are comparable or reduced for ISIS 372339 and ISIS 377130 as compared to ISIS 345198. Coupled with the target reduction as shown in Table 11, these data show that the enhanced potency of the gap-widened compounds is not due to enhanced accumulation of the compound in the liver. Thus, preferred oligonucleotides of the present invention include gap-widened oligonucleotides that show enhanced or comparable potency with regard to target reduction to the corresponding 5-10-5 gapmer without enhanced accumulation of the compound in a target tissue. In some embodiments, the target tissue is adipose and in some embodiments, the target tissue is liver.

Example 9

Design of "Gap-Widened" Antisense Oligonucleotides Targeting Human GCGR

A series of oligomeric compounds were designed to target human GCGR (Genbank accession number: NM_000160.1, incorporated herein as SEQ ID NO: 108), with varying sizes of the deoxynucleotide gap and 2'-MOE wings. Each of the oligonucleotides is 20 nucleobases in length and has the same nucleobase sequence (GCACTTTGTGGTGCCAAGGC, incorporated herein as SEQ ID NO: 93), and therefore targets the same segment of SEQ ID NO: 108 (nucleobases 532 to 551). The compounds are shown in Table 13. Plain text indicates a deoxynucleotide, and nucleotides designated with bold, underlined text are 2'-O-(2-methoxyethyl) nucleotides. Internucleoside linkages are phosphorothioate throughout, and all cytosines are 5-methylcytosines. Indicated in Table 13 is the "motif" of each compound, indicative of chemically distinct regions comprising the oligonucleotide.

TABLE 13

Antisense compounds targeting human GCGR

| ISIS Number | Chemistry | Motif |
|---|---|---|
| 310457 | GCACTTTGTGGTGCCAAGGC | 5-10-5 gapmer |
| 325448 | GCACTTTGTGGTGCCAAGGC | 2-16-2 gapmer |
| 325568 | GCACTTTGTGGTGCCAAGGC | 3-14-3 gapmer |

The 5-10-5 gapmer, ISIS 310457, was tested for its ability to reduce target mRNA levels in vitro. HepG2 cells were treated with ISIS 310457 using methods as described herein. ISIS 310457 was analyzed for its effect on human glucagon receptor mRNA levels by quantitative real-time PCR and was found to reduce expression of GCGR by about 96%.

Example 10

Design of "Gap-Widened" Antisense Oligonucleotides Targeting Rat GCGR

A series of oligomeric compounds were designed to target rat GCGR (Genbank accession number: M96674.1, incorporated herein as SEQ ID NO: 109) with varying sizes of the deoxynucleotide gap and 2'-MOE wings. Each of the oligonucleotides tested has the same nucleobase sequence (GCACTTTGTGGTACCAAGGT, incorporated herein as SEQ ID NO: 94) and therefore targets the same segment of SEQ ID NO: 109 (nucleobases 402 to 421). The segment targeted by the rat oligonucleotides corresponds to the segment of human GCGR targeted by ISIS 310457 (SEQ ID NO: 93). The compounds are shown in Table 14. Plain text indicates a deoxynucleotide, and nucleotides designated with bold, underlined text are 2'-O-(2-methoxyethyl) nucleotides. Internucleoside linkages are phosphorothioate throughout, and all cytosines are 5-methylcytosines. Indicated in Table 14 is the "motif" of each compound indicative of chemically distinct regions comprising the oligonucleotide.

TABLE 14

Antisense compounds targeting rat GCGR

| ISIS Number | Chemistry | Motif |
|---|---|---|
| 356171 | GCACTTTGTGGTACCAAGCT | 5-10-5 gapmer |
| 357368 | GCACTTTGTGGTACCAAGGT | Uniform deoxy |
| 357369 | GCACTTTGTGGTACCAAGGT | 1-18-1 gapmer |
| 357370 | GCACTTTGTGGTACCAAGGT | 1-17-2 gapmer |
| 357371 | GCACTTTGTGGTACCAAGGT | 2-16-2 gapmer |
| 357372 | GCACTTTGTGGTACCAAGGT | 3-14-3 gapmer |
| 357373 | GCACTTTGTGGTACCAAGCT | 4-12-4 gapmer |

TABLE 14-continued

Antisense compounds targeting rat GCGR

| ISIS Number | Chemistry | Motif |
| --- | --- | --- |

Example 11

Effects of Antisense Oligonucleotides Targeting GCGR—In Vivo Rat Study

In accordance with the present invention, the oligonucleotides designed to target rat GCGR were tested in vivo. Male Sprague Dawley rats, eight weeks of age, were injected with 50, 25, 12.5, or 6.25 mg/kg of ISIS 356171, ISIS 357368, ISIS 357369, ISIS 357370, ISIS 357371, ISIS 357372, or ISIS 357373 twice weekly for 3 weeks for a total of 6 doses. Saline-injected animals served as a control. Each of the oligonucleotides tested has the same nucleobase sequence (GCACTTTGTGGTACCAAGGT, incorporated herein as SEQ ID NO: 94), and the chemistry and motif of each compound is described above.

After the treatment period, rats were sacrificed and target nucleic acid levels were evaluated in liver. RNA isolation and target mRNA expression level quantitation are performed as described by other examples herein using RIBOGREEN™. RNA from each treatment group was assayed alongside RNA from the group treated with ISIS 356171. Results are presented in Table 15a, 15b, 15c, 15d, 15e, and 15f as a percentage of saline-treated control levels.

TABLE 15a

Reduction of target levels in liver of rats treated with 2-16-2 antisense oligonucleotides targeted to GCGR

| | | % Control Dose of oligonucleotide (mg/kg) | | | |
| --- | --- | --- | --- | --- | --- |
| Treatment | Motif | 50 | 25 | 12.5 | 6.25 |
| ISIS 356171 | 5-10-5 | 7 | 20 | 26 | 36 |
| ISIS 357371 | 2-16-2 | 11 | 22 | 35 | 39 |

TABLE 15b

Reduction of target levels in liver of rats treated with 3-14-3 antisense oligonucleotides targeted to GCGR

| | | % Control Dose of oligonucleotide (mg/kg) | | | |
| --- | --- | --- | --- | --- | --- |
| Treatment | Motif | 50 | 25 | 12.5 | 6.25 |
| ISIS 356171 | 5-10-5 | 10 | 24 | 28 | 50 |
| ISIS 357372 | 3-14-3 | 12 | 23 | 37 | 56 |

TABLE 15c

Reduction of target levels in liver of rats treated with 4-12-4 antisense oligonucleotides targeted to GCGR

| | | % Control Dose of oligonucleotide (mg/kg) | | | |
| --- | --- | --- | --- | --- | --- |
| Treatment | Motif | 50 | 25 | 12.5 | 6.25 |
| ISIS 356171 | 5-10-5 | 10 | 25 | 36 | 47 |
| ISIS 357373 | 4-12-4 | 13 | 22 | 48 | 47 |

TABLE 15d

Reduction of target levels in liver of rats treated with 1-17-2 antisense oligonucleotides targeted to GCGR

| | | % Control Dose of oligonucleotide (mg/kg) | | | |
| --- | --- | --- | --- | --- | --- |
| Treatment | Motif | 50 | 25 | 12.5 | 6.25 |
| ISIS 356171 | 5-10-5 | 8 | 24 | 32 | 43 |
| ISIS 357370 | 1-17-2 | 20 | 41 | 62 | 68 |

TABLE 15e

Reduction of target levels in liver of rats treated with 1-18-1 antisense oligonucleotides targeted to GCGR

| | | % Control Dose of oligonucleotide (mg/kg) | | | |
| --- | --- | --- | --- | --- | --- |
| Treatment | Motif | 50 | 25 | 12.5 | 6.25 |
| ISIS 356171 | 5-10-5 | 9 | 27 | 34 | 46 |
| ISIS 357369 | 1-18-1 | 33 | 35 | 58 | 70 |

TABLE 15f

Reduction of target levels in liver of rats treated with uniform deoxy oligonucleotides targeted to GCGR

| | | % Control Dose of oligonucleotide (mg/kg) | | | |
| --- | --- | --- | --- | --- | --- |
| Treatment | Motif | 50 | 25 | 12.5 | 6.25 |
| ISIS 356171 | 5-10-5 | 8 | 23 | 30 | 45 |
| ISIS 357368 | Uniform deoxy | 31 | 43 | 77 | 73 |

As shown in Tables 15a, 15b, 15c, 15d, and 15e the gap-widened antisense oligonucleotides were effective at reducing GCGR levels in vivo in a dose-dependent manner.

In addition, oligonucleotide concentration in kidney and liver were determined. Methods to determine oligonucleotide concentration in tissues are known in the art (Geary et al., *Anal. Biochem.*, 1999, 274, 241-248). Shown in Table 16 are the total oligonucleotide concentration and the concentration of full length oligonucleotide (in µg/g) in the kidney or liver of animals treated with 25 mg/kg of the indicated oligonucleotide. Total oligonucleotide is the sum of all oligonucleotides metabolites detected in the tissue.

TABLE 16

Concentration of oligonucleotide in liver and kidney

| Treatment | Motif | Kidney Total oligo | Kidney Full-length | Liver Total oligo | Liver Full-length |
|---|---|---|---|---|---|
| ISIS 356171 | 5-10-5 gapmer | 1814 | 1510 | 621 | 571 |
| ISIS 356368 | Uniform deoxy | 801 | 183 | 282 | 62 |
| ISIS 356369 | 1-18-1 | 1237 | 475 | 309 | 171 |
| ISIS 356370 | 1-17-2 | 1127 | 590 | 370 | 271 |
| ISIS 356371 | 2-16-2 | 871 | 515 | 345 | 253 |
| ISIS 356372 | 3-14-3 | 1149 | 774 | 497 | 417 |
| ISIS 356373 | 4-12-4 | 902 | 687 | 377 | 326 |

As shown in Table 16, the concentrations of the gap-widened oligonucleotides in kidney were generally reduced with respect to those found for ISIS 356171 in these tissues. Taken with the target reduction data shown in Table 15 wherein potency was maintained with ISIS 356371, ISIS 356372, and ISIS 356373 with respect to ISIS 356171, these data suggest that gap-widened oligos, particularly ISIS 356371, ISIS 356372, and ISIS 356373 are, in essence, more effective than ISIS 356171 at reducing target levels in the liver.

Example 12

Effects of Antisense Oligonucleotides Targeting GCGR—In Vivo Study in Cynomolgus Monkeys To evaluate alterations in tissue distribution, potency, or therapeutic index caused by modification of the antisense oligonucleotide motif in a primate, cynomolgus monkeys were injected with ISIS 310457 (5-10-5 motif) or ISIS 325568 (2-16-2 motif) at doses of 3, 10, or 20 mg/kg per week. These antisense compounds show 100% complementarity to the monkey GCGR target sequence. Animals injected with saline alone served as controls. The duration of the study was 7 weeks, and the animals were dosed three times during the first week, followed by once-weekly dosing for 6 weeks. Each treatment group was comprised of 5 animals. One group treated with 20 mg/kg of ISIS 310457 and one group treated with 20 mg/kg of ISIS 325568 recovered for three weeks after cessation of dosing prior to sacrifice ("20 mg/kg recovery"). Other treatment groups were sacrificed at the end of the study. Liver tissues were collected to assess target reduction.

RNA isolation and target mRNA expression level quantitation were performed as described by other examples herein using RIBOGREEN™. Results are presented in Table 17 as a percentage of saline-treated control levels.

TABLE 17

Reduction of target levels in liver of monkeys treated with antisense oligonucleotides targeted to GCGR

| | | % Control Dose of oligonucleotide | | | |
|---|---|---|---|---|---|
| Treatment | Motif | 20 mg/kg, recovery | 20 mg/kg | 10 mg/kg | 3 mg/kg |
| ISIS 310457 | 5-10-5 | 27 | 34 | 43 | 71 |
| ISIS 325568 | 2-16-2 | 43 | 45 | 54 | 49 |

As shown in Table 17, treatment with ISIS 310457 and 325568 caused decreases in GCGR levels at all of the doses tested, and reduction in target levels was still observed in the 20 mg/kg recovery groups. ISIS 325568 caused greater reduction than ISIS 310457 at the 3 mg/kg dose.

In addition, oligonucleotide concentration in kidney and liver were determined. Methods to determine oligonucleotide concentration in tissues are known in the art (Geary et al., Anal Biochem, 1999, 274, 241-248). Shown in Table 18 are the total concentration and the concentration of full length oligonucleotide (in µg/g) in the kidney or liver of animals treated with the indicated oligonucleotide.

TABLE 18

Concentration of oligonucleotide in liver and kidney

| Treatment | Motif | Dose | Kidney Total oligo | Kidney Full-length | Liver Total oligo | Liver Full-length |
|---|---|---|---|---|---|---|
| ISIS 310457 | 5-10-5 | 3 mg/kg | 471 | 423 | 449 | 330 |
| | | 10 mg/kg | 1011 | 911 | 710 | 606 |
| | | 20 mg/kg | 1582 | 1422 | 981 | 867 |
| | | 20 mg/kg recovery | 449 | 347 | 648 | 498 |
| ISIS 325568 | 2-16-2 | 3 mg/kg | 356 | 298 | 309 | 228 |
| | | 10 mg/kg | 830 | 685 | 477 | 339 |
| | | 20 mg/kg | 1390 | 1101 | 739 | 544 |
| | | 20 mg/kg recovery | 264 | 161 | 344 | 205 |

As shown in Table 18, the kidney concentration of the 5-10-5 motif oligonucleotide ISIS 310457 is higher than that measured for the 2-16-2 motif oligonucleotide ISIS 325568 at all concentrations tested. Taken with the target reduction data in Table 9 for the 2-16-2 motif oligonucleotide, these data suggest that the gap-widened oligonucleotide is more potent than the corresponding 5-10-5 motif oligonucleotide, providing a more robust lowering of target mRNA levels in the liver without enhanced accumulation of oligonucleotide.

Example 13

Effects of Gap-Widened Oligonucleotides on Reduction of DGAT2 mRNA Levels—In Vitro Analysis In accord with the present invention, oligonucleotides were designed to target DGAT2.

Shown in Table 19 is the sequence of each oligonucleotide. Plain text indicates a deoxynucleotide, and nucleotides designated with bold, underlined text are 2'-O-(2-methoxyethyl) nucleotides. Also shown for each oligonucleotide in Table 19 is its motif, the target site on human DGAT2 mRNA (GENBANK® accession number NM_032564.2, incorporated herein as SEQ ID NO: 110), and its cross-species identity. For each species listed, an "X" denotes perfect complementarity to the target sequence for that species, "1 MM" denotes one mismatch to the target sequence for the species, etc.

TABLE 19

Antisense compounds targeting DGAT2

SEQ

| ISIS # | Sequence | ID NO | Target Site | Motif | Human | Monkey | Rat | Mouse |
|---|---|---|---|---|---|---|---|---|
| 217328 | GCATTGCCACTCCCATTCTT | 95 | 909 | 5-10-5 | X | X | 1 MM | X |
| 334177 | AGGACCCCGGAGTAGGCGGC | 96 | 246 | 5-10-5 | X | X | 1 MM | X |
| 366710 | GACCTATTGAGCCAGGTGAC | 97 | 396 | 5-10-5 | X | X | 2 MM | 2 MM |
| 366714 | GTAGCTGCTTTTCCACCTTG | 98 | 416 | 5-10-5 | X | X | 2 MM | 3 MM |
| 370727 | AGCTGCTTTTCCACCTTGGA | 99 | 414 | 2-16-2 | X | X | 2 MM | 2 MM |
| 370747 | TGGAGCTCAGAGACTCAGCC | 100 | 953 | 2-16-2 | X | X | 3 MM | 2 MM |
| 370784 | GCTGCATCCATGTCATCAGC | 101 | 2099 | 2-16-2 | X | X | >3 MM | >3 MM |

Each of these oligonucleotides was tested in vitro for their ability to reduce human DGAT2 mRNA levels using real time RT-PCR methods as described herein. In HepG2 and A549 cells, each of the oligonucleotides in Table 19 demonstrated $IC_{50}$ values of about 20 nM.

Example 14

Effects of Gap-Widened Oligonucleotides on Reduction of DGAT2 mRNA Levels—In Vivo Analysis The oligonucleotides described in Table 19, along with ISIS 217357 (ACACACTAGAAGTGAGCTTA, SEQ ID NO: 102), which is targeted to rat DGAT2, the complement of nucleotides 15333000 to 15365000 of GENBANK® accession number NW_047561.1, herein incorporated as SEQ ID NO: 111 were tested for their ability to reduce DGAT2 levels in vivo. Eight week-old male Sprague-Dawley rats were injected with 20 mg/kg of oligonucleotide per week for 2 weeks. Each treatment group was comprised of 6 animals. Animals injected with saline alone served as controls.

At the end of the treatment period, animals were sacrificed and liver and kidney tissues were harvested. To determine effects of altering the gap size on pharmacokinetics, oligonucleotide concentration in kidney and liver were determined. Methods to determine oligonucleotide concentration in tissues are known in the art (Geary et al., *Anal Biochem*, 1999, 274, 241-248). Total oligonucleotide is the sum of all oligonucleotides metabolites detected in the tissue. Shown in Table 20 are the total concentration and the concentration of full length oligonucleotide (in μg/g) in the liver of animals treated with the indicated oligonucleotide concentration.

TABLE 20

Concentration of DGAT2 oligonucleotides in rat liver and kidney

| Treatment group | Motif | Total Liver | Total Kidney | Full length Liver | Full length Kidney |
|---|---|---|---|---|---|
| ISIS 217357 | 5-10-5 | 91 | 441 | 70 | 328 |
| ISIS 217328 | 5-10-5 | 145 | 399 | 121 | 294 |
| ISIS 334177 | 5-10-5 | 164 | 650 | 114 | 392 |
| ISIS 366710 | 5-10-5 | 166 | 625 | 123 | 401 |
| ISIS 366714 | 5-10-5 | 278 | 674 | 214 | 488 |
| ISIS 370727 | 2-16-2 | 209 | 355 | 131 | 166 |
| ISIS 370747 | 2-16-2 | 195 | 480 | 150 | 342 |
| ISIS 370784 | 2-16-2 | 303 | 669 | 256 | 421 |

As shown in Table 20, kidney concentrations of gap-widened oligonucleotides, particularly ISIS 370727 and ISIS 370747, were generally lower than those of oligonucleotides with a 10-deoxynucleotide gap.

Example 15

Effects of Gap-Widened Oligonucleotides on Reduction of DGAT2 mRNA Levels—In Vivo Analysis In another arm of the experiment described in Example 14, eight-week old male Sprague-Dawley rats were treated with the oligonucleotides at doses of 50 mg/kg per week for four weeks. Each treatment group was comprised of 4 animals. At the end of the treatment period, animals were sacrificed and target mRNA levels were determined using real-time RT-PCR as described herein. Results are shown in Table 21 as the average % inhibition for each treatment group.

TABLE 21

Reduction of target levels in rat liver with oligonucleotides targeting DGAT2

| Treatment group | Motif | % Inhibition |
|---|---|---|
| ISIS 217357 | 5-10-5 | 25 |
| ISIS 217328 | 5-10-5 | 48 |
| ISIS 334177 | 5-10-5 | 51 |
| ISIS 366710 | 5-10-5 | 63 |
| ISIS 366714 | 5-10-5 | 67 |
| ISIS 370727 | 2-16-2 | 77 |
| ISIS 370747 | 2-16-2 | 79 |
| ISIS 370784 | 2-16-2 | 52 |

As shown in Table 21, the gap-widened oligonucleotides targeted to DGAT2 show excellent inhibitory activity in the liver. ISIS 370727 and ISIS 370747, in particular, showed superior ability to reduce target expression. Taken with the distribution of these oligonucleotides in the liver as shown in Table 20, these data suggest that gap-widened oligonucleotides provide excellent to superior target reduction without enhanced accumulation of oligonucleotide in target tissues. In addition, the gap-widened oligonucleotides possess a preferred liver to kidney ratio as compared to the 5-10-5 motif oligonucleotides targeting DGAT2.

Example 16

Effects of Gap-Widened Oligonucleotides on Reduction of CRP mRNA Levels—In *Vivo Analysis*

Monkey-human cross-species oligonucleotides targeted to C-reactive protein (CRP) were designed to target CRP using sequences known in the art (see US application publication number U.S. 2005-0014257, herein incorporated by reference in its entirety). Shown in Table 22 is the sequence of oligonucleotides targeted to CRP tested in cynomologus monkeys. Plain text indicates a deoxynucleotide, and nucleotides designated with bold, underlined text are 2'-O-(2-methoxyethyl) nucleotides. Also shown for each oligonucleotide in Table 22 is its motif

TABLE 22

Antisense oligonucleotides targeting CRP

| Isis # | Sequence | SEQ ID NO | Motif |
|---|---|---|---|
| 353512 | TCCCATTTCAGGAGACCTGG | 115 | 3-14-3 |
| 330012 | TCCCATTTCAGGAGACCTGG | 115 | 5-10-5 |
| 353491 | GCACTCTGGACCCAAACCAG | 116 | 3-14-3 |
| 133726 | GCACTCTGGACCCAAACCAG | 116 | 5-10-5 |

Methods of assaying for activity of CRP compounds in vivo and in vitro are known in the art (see US application publication number U.S. 2005-0014257, herein incorporated by reference). Toxicity profiles of gap-widened oligonucleotides were compared to the 5-10-5 oligonucleotides by treating monkeys with 14 or 40 mg/kg/wk for 4 weeks. Activity was compared in a dose-escalation study with each cycle containing four subcutaneous doses administered (Mon., Wed., Fri., Mon.) in 4 dosing cycles over 8 weeks. Doses were 2, 4 and 10 mg/kg. At 48 hr following the last dose in each treatment cycle, monkeys were challenged with 1 to 2 µg/kg IL-6 (administered subcutaneously) and serum CRP levels were quantified over 36 hours. Serum CRP levels may be measured by ELISA using a commercially available kit (for example, ALerCHEK Inc., Portland, Me.). Animals were sacrificed after the second and fourth cycles and liver CRP mRNA, tissue oligonucleotide concentration, clinical signs, serum chemistry, hematology, body weight, and histology were assessed. With regard to tissue oligonucleotide concentration and histology, the primary difference was 30% lower kidney concentration and fewer histologic changes in the 3-14-3 treated animals. Plasma cytokine and CRP levels were examined but not significantly increased.

Several CRP inhibitors were pharmacologically active, with the greatest reductions in serum CRP (30-66%) and hepatic CRP mRNA (60-85%) observed at both the 4 and 10 mg/kg treatment cycles.

We have surprisingly found that chimeric antisense compounds with gaps at least 11 nucleobases long and wings which are from independently from 1 to 4 nucleobases in length which are 2'-MOE-modified. This enhanced efficacy is not predicted by the rank order potency of these compounds in vitro (cell culture). 2-16-2 and 3-14-3 gapmer compounds as well as 3-10-7 and 7-10-3 gapmer compounds have been shown to be more effective than 5-10-5 chimeras of the equivalent sequence and wing modification. 4-12-4 gapmers are also believed to be a useful embodiment.

DETAILED DESCRIPTION OF EMBODIMENTS

Non-limiting examples of 2'-modified nucleosides useful in the compounds of the present invention, include but are not limited to 2'-O-alkyl, 2'-O-alkyl-O-alkyl wherein alkyl is a $C_1$ to $C_6$ alkyl or $C_1$ to $C_6$ alkylene when alkyl is not a terminal substituent. These include 2'-O-methyl, 2'-O-propyl and 2'-O-methoxyethyl nucleosides.

Details

The present invention uses antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide-mediated inhibition of gene expression. The cleavage of RNA:RNA hybrids can, in like fashion, be accomplished through the actions of endoribonucleases, such as RNAseL which cleaves both cellular and viral RNA. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been, referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference in its entirety.

Synthesis of Nucleoside Phosphoramidites

The following compounds, including amidites and their intermediates were prepared as described in U.S. Pat. No. 6,426,220 and published PCT WO 02/36743; 5'-ODimethoxytrityl-thymidine intermediate for 5-methyl dC amidite, 5'-O-Dimethoxytrityl2'-deoxy-5-methylcytidine intermediate for 5-methyl-dC amidite, 5'-O-Dimethoxytrityl2'-deoxy-N-4-benzoyl-5-methylcytidine penultimate intermediate for 5-methyl dC amidite, [5'-O-(4,4'-Dimethoxytriphenylmethyl)-2'-deoxy-N-4-benzoyl-5-methylcytidin-3'O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'Fluorodeoxycytidine, 2'-O-(2-Methoxyethyl) modified amidites, 2'-O-(2-methoxyethyl)5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'O-dimethoxytrityl-2'-O-(2-methoxyethyl)-N-4-benzoyl-5-methyl-cytidine penultimate intermediate, [5'-O-(4,4'-Dimethoxytriphenylmethyl)-2'-O-(2-methoxyethyl)-N-4-benzoyl5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N6benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-

N4isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tertButyldiphenylsilyl-O2-2'-anhydro-5-methyluridine, 5'-O-tert-Butyldiphenylsilyl-2'-O-(2hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5methyluridine, 5'-O-tert-Butyldiphenylsilyl-2'-O-[N,N dimethylaminooxyethyl]-5methyluridine, 2'-O-(dimethylaminooxyethyl)-5-methyluridine, 5'-O-DMT-2'-O(dimethylaminooxyethyl)-5-methyluridine, 5'-O-DMT-2'-O-(2-N, Ndimethylaminooxyethyl)-5-methyluridine-3'-[(2-cyanoethyl)-N,N-diisopropylphosphoramidite], 2'-(Aminooxyethoxy) nucleoside amidites, N2-isobutyryl6-O-diphenylcarbamoyl-2'-O-(2-ethylacetyl)-5'-O-(4,4'-dimethoxytrityl)guanosine-3'-[(2cyanoethyl)-N,N-diisopropylphosphoramidite], 2'-dimethylaminoethoxyethoxy (2'DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine. Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH4OAc solution. Phosphinate oligonucleotides are prepared as described in U.S. Pat. No. 5,508,270, herein incorporated by reference. Alkyl phosphonate oligonucleotides are prepared as described in U.S. Pat. No. 4,469,863, herein incorporated by reference.3'-Deoxy-3'-methylene phosphonate oligonucleotides are prepared as described in U.S. Pat. No. 5,610,289 or 5,625,050, herein incorporated by reference. Phosphoramidite oligonucleotides are prepared as described in U.S. Pat. No. 5,256, 775 or U.S. Pat. No. 5,366,878, herein incorporated by reference. Alkylphosphonothioate oligonucleotides are prepared as described in published PCT applications PCT/US94/00902 and PCT/US93/06976 (published as WO 94/17093 and WO 94/02499, respectively), herein incorporated by reference. 3'-Deoxy-3'-amino phosphoramidate oligonucleotides are prepared as described in U.S. Pat. No. 5,476,925, herein incorporated by reference. Phosphotriester oligonucleotides are prepared as described in U.S. Pat. No. 5,023, 243, herein incorporated by reference. Borano phosphate oligonucleotides are prepared as described in U.S. Pat. Nos. 5,130,302 and 5,177,198, both herein incorporated by reference. Oligonucleosides: Methylenemethylimino linked oligonucleosides, also identified as MMI linked oligonucleosides, methylenedimethylhydrazo linked oligonucleosides, also identified as MDH linked oligonucleosides, and methylenecarbonyl amino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378, 825, 5,386,023, 5,489,677, 5,602,240 and 5,610,289, all of which are herein incorporated by reference. Formacetal and thioformacetal linked oligonucleosides are prepared as described in U.S. Pat. Nos. 5,264,562 and 5,264,564, herein incorporated by reference. Ethylene oxide linked oligonucleosides are prepared as described in U.S. Pat. No. 5,223, 618, herein incorporated by reference.

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl. Following this procedure for the sequential protection of the 5'-hydroxyl in combination with protection of the 2'-hydroxyl by protecting groups that are differentially removed and are differentially chemically labile, RNA oligonucleotides were synthesized. RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide. Following synthesis, the methyl protecting groups on the phosphates are cleaved in 30 minutes utilizing 1 M disodium-2-carbamoyl-2-cyanoethylene-1,1-dithiolate trihydrate (S2Na2) in DMF. The deprotection solution is washed from the solid supportbound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties.

It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed, Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product. Additionally, methods of RNA synthesis are well known in the art (Scaringe, S. A. Ph.D. Thesis, University of Colorado, 1996; Scaringe, S. A., et al., J. Am. Chem. Soc., 1"8, 120, 11820-11821; Matteucci, M. D. and Caruthers, M. H. J. Am. Chem. Soc., 1981, 103, 3185-3191; Beaucage, S. L. and Caruthers, M. H. Tetrahedron Lett., 1981, 22, 1859-1862; Dahl, B. J., et al., Acta Chem. Scand, 1990, 44, 639-641; Reddy, M. P., et al., Tetrahedron Lett., 1994, 25, 4311-4314; Wincott, F. et al., Nucleic Acids Res., 1995, 23, 2677-2684; Griffin, B. E., et al., Tetrahedron, 1967, 23, 2301-2313; Griffin, B. E., et al., Tetrahedron, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 uM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid.

Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH4OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]; -[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2Methoxyethyl) Phosphodiester] Chimeric Oligonucleotides

[2'-O-(2-methoxyethyl phosphodiester]-[2'-deoxy phosphorothioate]-[2'-O(methoxyethyl) phosphodiester] chimeric oligonucleotides are prepared as per the above procedure for the 2'-O-methyl chimeric oligonucleotide with the substitution of 2'-O(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

The methods of the present invention are particularly useful in antisense therapeutics. It is not necessary that the antisense target be associated with liver disease per se, since many current antisense targets are expressed to high levels in liver and other organs. In particular, targets associated with metabolic and cardiovascular diseases and conditions are particularly amenable to knockdown in the liver and have been shown in animals and in clinical studies to have therapeutic effects).

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The invention claimed is:

1. A method of reducing expression of a target RNA in an animal, in need of reducing expression of said target RNA, comprising administering to said animal a gap-widened antisense oligonucleotide 18-24 nucleotides in length targeting a preselected RNA target in the liver, wherein said oligonucleotide comprises:
   (a) a gap region having 12 to 18 contiguous 2'-deoxyribonucleotides;
   (b) a first wing region having 2 to 4 contiguous nucleosides; and
   (c) a second wing region having 2 to 4 contiguous nucleosides; wherein the gap region is located between said first wing region and said second wing region and, wherein each nucleoside of said first and second wing regions comprises a 2'-O-(2-methoxyethyl) modification;
   thereby reducing expression of said preselected RNA target in the liver of said animal.

2. The method of claim 1, wherein the target RNA is associated with a metabolic or a cardiovascular disease or condition.

3. The method of claim 1, wherein the metabolic disease or condition is selected from metabolic syndrome, diabetes, obesity, hyperlipidemia, hypercholesterolemia, hypertriglyceridemia, Type 2 diabetes, diet-induced obesity, hyperglycemia, insulin resistance, hepatic steatosis, fatty liver disease, or non-alcoholic steatohepatitis.

4. The method of claim 1, wherein the cardiovascular disease or condition is selected from familial hypercholesterolemia, nonfamilial hypercholesterolemia, mixed dyslipidemia, dysbetalipoproteinemia, atherosclerosis, coronary artery disease, myocardial infarction, hypertension, carotid artery disease, stroke, cerebrovascular disease, peripheral vascular disease, thrombosis, or arterial aneurism.

5. The method of claim 1, wherein the gap-widened antisense oligonucleotide has at least one phosphorothioate internucleotide linkage.

6. The method of claim 5, wherein the gap-widened antisense oligonucleotide has all phosphorothioate internucleotide linkages.

7. The method of claim 1, wherein gap-widened antisense oligonucleotide has at least one 5-methylcytosine.

8. A method of modulating gene expression in an animal comprising the step of contacting said animal with a pharmaceutical composition comprising a gap-widened antisense oligonucleotide 18-24 nucleotides in length targeting a preselected RNA target in the liver in the manufacture of a medicament for the treatment of disorders and diseases related to said RNA, wherein the antisense oligonucleotide comprises:
   (a) a gap region having 12 to 18 contiguous 2'-deoxyribonucleotides;
   (b) a first wing region having 2 to 4 contiguous nucleosides; and
   (c) a second wing region having 2 to 4 contiguous nucleosides; wherein the gap region is located between said first wing region and said second wing region and, wherein each nucleoside of said first and second wing regions comprises a 2'-O-(2-methoxyethyl) modification;

thereby modulating the expression of said preselected RNA target in the liver of said animal.

9. The method of claim 1, wherein said wing-gap-wing motif is selected from 2-16-2, 3-14-3, 2-14-2, 3-12-3 and 4-12-4.

10. The method of claim 9, wherein said wing-gap-wing motif is 2-16-2.

11. The method of claim 9, wherein said wing-gap-wing motif is 3-14-3.

12. The method of claim 9, wherein said wing-gap-wing motif is 2-14-2.

13. The method of claim 9, wherein said wing-gap-wing motif is 3-12-3.

14. The method of claim 9, wherein said wing-gap-wing motif is 4-12-4.

15. The method of claim 8, wherein said wing-gap-wing motif is selected from 2-16-2, 3-14-3, 2-14-2, 3-12-3 and 4-12-4.

16. The method of claim 15, wherein said wing-gap-wing motif is 2-16-2.

17. The method of claim 15, wherein said wing-gap-wing motif is 3-14-3.

18. The method of claim 15, wherein said wing-gap-wing motif is 2-14-2.

19. The method of claim 15, wherein said wing-gap-wing motif is 3-12-3.

20. The method of claim 15, wherein said wing-gap-wing motif is 4-12-4.

* * * * *

SEQUENCE LISTING

<160> NUMBER OF SEQ ID NOS: 116

<210> SEQ ID NO 1
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 1
ctgctagcct ctggatttga          20

<210> SEQ ID NO 2
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 2
ccttccctga aggttcctcc          20

<210> SEQ ID NO 3
<211> LENGTH: 18
<212> TYPE: DNA
<213> ORGANISM: Artificial Sequence
<220> FEATURE:
<223> OTHER INFORMATION: Oligomeric Compound

<400> SEQUENCE: 3
gctcatactc gtaggcca          18

<210> SEQ ID NO 4
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 4
tcgatctcct tttatgcccg          20

<210> SEQ ID NO 5
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 5
tctgtctctc ccatatacag          20

<210> SEQ ID NO 6
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 6
tgtttctgtc tctcccatat          20

<210> SEQ ID NO 7
<211> LENGTH: 20
<212> TYPE: DNA

```
<213> ORGANISM: Artificial Sequence
<220> FEATURE:
<223> OTHER INFORMATION: Oligomeric Compound

<400> SEQUENCE: 7
cttttgtttc tgtctctccc                                                    20

<210> SEQ ID NO 8
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 8
atcacttttg tttctgtctc                                                    20

<210> SEQ ID NO 9
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 9
gtttgcaatg ctttcttcca                                                    20

<210> SEQ ID NO 10
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 10
tgaggtttgc aatgctttct                                                    20

<210> SEQ ID NO 11
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 11
ctattgaggt ttgcaatgct                                                    20

<210> SEQ ID NO 12
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 12
cgacctattg aggtttgcaa                                                    20

<210> SEQ ID NO 13
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 13
ctggtcgacc tattgaggtt                                                    20
```

-continued

```
<210> SEQ ID NO 14
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 14
ctgtggtata caatttcaca                                           20

<210> SEQ ID NO 15
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 15
ctttggtctg tggtatacaa                                           20

<210> SEQ ID NO 16
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 16
gtcaaaggtg ctttggtctg                                           20

<210> SEQ ID NO 17
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 17
ggtttagtgt ccggtaaaat                                           20

<210> SEQ ID NO 18
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 18 cttttctgt tttcacttgg                                            20

<210> SEQ ID NO 19
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 19
ttctcttgct taattacccc                                           20

<210> SEQ ID NO 20
<211> LENGTH: 20
<212> TYPE: DNA
<213> ORGANISM: Artificial Sequence
<220> FEATURE:
<223> OTHER INFORMATION: Oligomeric Compound
```

```
<400> SEQUENCE: 20
cagtttctct tgcttaatta                                          20

<210> SEQ ID NO 21
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 21
gcccagtttc tcttgcttaa                                          20

<210> SEQ ID NO 22
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 22
tttattacca attatatttg                                          20

<210> SEQ ID NO 23
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 23
acattttatt accaattata                                          20

<210> SEQ ID NO 24
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 24
gcagacattt tattaccaat                                          20

<210> SEQ ID NO 25
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 25
aatggcagac attttattac                                          20

<210> SEQ ID NO 26
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 26
cagaaatggc agacatttta                                          20

<210> SEQ ID NO 27
<211> LENGTH: 20
<212> TYPE: DNA
```

-continued

```
<213> ORGANISM: Artificial Sequence
<220> FEATURE:
<223> OTHER INFORMATION: Oligomeric Compound

<400> SEQUENCE: 27
tgaacagaaa tggcagacat                                                 20

<210> SEQ ID NO 28
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 28
ccatgaacag aaatggcaga                                                 20

<210> SEQ ID NO 29
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 29
cacaccatga acagaaatgg                                                 20

<210> SEQ ID NO 30
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 30
tactcacacc atgaacagaa                                                 20

<210> SEQ ID NO 31
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 31
gaggtactca caccatgaac                                                 20

<210> SEQ ID NO 32
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 32
tccagaggta ctcacaccat                                                 20

<210> SEQ ID NO 33
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 33
gtcctccaga ggtactcaca                                                 20
```

```
<210> SEQ ID NO 34
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 34
atctgtcctc cagaggtact                                               20

<210> SEQ ID NO 35
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 35
gtacatctgt cctccagagg                                               20

<210> SEQ ID NO 36
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 36
agtggtacat ctgtcctcca                                               20

<210> SEQ ID NO 37
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 37
tcatagtggt acatctgtcc                                               20

<210> SEQ ID NO 38
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 38
catgtcatag tggtacatct                                               20

<210> SEQ ID NO 39
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 39
tattcatgtc atagtggtac                                               20

<210> SEQ ID NO 40
<211> LENGTH: 20
<212> TYPE: DNA
<213> ORGANISM: Artificial Sequence
<220> FEATURE:
<223> OTHER INFORMATION: Oligomeric Compound
```

-continued

```
<400> SEQUENCE: 40
gctgtattca tgtcatagtg                                           20

<210> SEQ ID NO 41
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 41
ggatgctgta ttcatgtcat                                           20

<210> SEQ ID NO 42
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 42
aaagggatgc tgtattcatg                                           20

<210> SEQ ID NO 43
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 43
tgagaaaggg atgctgtatt                                           20

<210> SEQ ID NO 44
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 44
tggtggaatg acattaaaaa                                           20

<210> SEQ ID NO 45
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 45
gaattggtgg aatgacatta                                           20

<210> SEQ ID NO 46
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 46
gagcttacat ctggtctcat                                           20

<210> SEQ ID NO 47
<211> LENGTH: 20
<212> TYPE: DNA
```

```
<213> ORGANISM: Artificial Sequence
<220> FEATURE:
<223> OTHER INFORMATION: Oligomeric Compound

<400> SEQUENCE: 47
aggagagctt acatctggtc                                               20

<210> SEQ ID NO 48
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 48
atggaggaga gcttacatct                                               20

<210> SEQ ID NO 49
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 49
ctggatggag gagagcttac                                               20

<210> SEQ ID NO 50
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 50
gagctggatg gaggagagct                                               20

<210> SEQ ID NO 51
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 51
tgtccttcca ctgctctttt                                               20

<210> SEQ ID NO 52
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 52
gtgctgtcct tccactgctc                                               20

<210> SEQ ID NO 53
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 53
aattgtgctg tccttccact                                               20
```

```
<210> SEQ ID NO 54
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 54
aggtaattgt gctgtccttc                                               20

<210> SEQ ID NO 55
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 55
cggcatgctg ggcagttttt                                               20

<210> SEQ ID NO 56
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 56
atagcggcat gctgggcagt                                               20

<210> SEQ ID NO 57
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 57
cgatagcggc atgctgggca                                               20

<210> SEQ ID NO 58
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 58
attccagcct gaagacattt                                               20

<210> SEQ ID NO 59
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 59
gttcattcca gcctgaagac                                               20

<210> SEQ ID NO 60
<211> LENGTH: 20
<212> TYPE: DNA
<213> ORGANISM: Artificial Sequence
<220> FEATURE:
<223> OTHER INFORMATION: Oligomeric Compound
```

```
<400> SEQUENCE: 60
ttctttgttt ttcgagcttc                                               20

<210> SEQ ID NO 61
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 61
tttttctttt gtttttcgag                                               20

<210> SEQ ID NO 62
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 62
caggaactat tgttttgtta                                               20

<210> SEQ ID NO 63
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 63
tgcaggaact attgttttgt                                               20

<210> SEQ ID NO 64
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 64
gagctatcat atcctgcata                                               20

<210> SEQ ID NO 65
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 65
aacagagcta tcatatcctg                                               20

<210> SEQ ID NO 66
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 66
ctggaacaga gctatcatat                                               20

<210> SEQ ID NO 67
<211> LENGTH: 20
<212> TYPE: DNA
```

```
<213> ORGANISM: Artificial Sequence
<220> FEATURE:
<223> OTHER INFORMATION: Oligomeric Compound

<400> SEQUENCE: 67
ttcactgctg caatcacttg                                              20

<210> SEQ ID NO 68
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 68
ccatttcact gctgcaatca                                              20

<210> SEQ ID NO 69
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 69
ttgcccattt cactgctgca                                              20

<210> SEQ ID NO 70
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 70
ataatcagat caggagcaaa                                              20

<210> SEQ ID NO 71
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 71
attaataatc agatcaggag                                              20

<210> SEQ ID NO 72
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 72
gctcattaat aatcagatca                                              20

<210> SEQ ID NO 73
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 73
ctctgctcat taataatcag                                              20
```

-continued

```
<210> SEQ ID NO 74
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 74
cattctctgc tcattaataa                                                  20

<210> SEQ ID NO 75
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 75
agcatgtgtt tacattggtc                                                  20

<210> SEQ ID NO 76
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 76
aaggttttca tacagagata                                                  20

<210> SEQ ID NO 77
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 77
cagtaaggtt ttcatacaga                                                  20

<210> SEQ ID NO 78
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 78
gaagcagtaa ggttttcata                                                  20

<210> SEQ ID NO 79
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 79
gagagaagca gtaaggtttt                                                  20

<210> SEQ ID NO 80
<211> LENGTH: 20
<212> TYPE: DNA
<213> ORGANISM: Artificial Sequence
<220> FEATURE:
<223> OTHER INFORMATION: Oligomeric Compound
```

-continued

```
<400> SEQUENCE: 80
gcttttccta gctctttgat                                              20

<210> SEQ ID NO 81
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 81
atggcttttc ctagctcttt                                              20

<210> SEQ ID NO 82
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 82
atggtcttat ccaaaaatgt                                              20

<210> SEQ ID NO 83
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 83
actcatggtc ttatccaaaa                                              20

<210> SEQ ID NO 84
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 84
caatactcat ggtcttatcc                                              20

<210> SEQ ID NO 85
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 85
aattcaatac tcatggtctt                                              20

<210> SEQ ID NO 86
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 86
atgatttcag ctaacatctc                                              20

<210> SEQ ID NO 87
<211> LENGTH: 20
<212> TYPE: DNA
```

-continued

<210> SEQ ID NO 87 (implied continuation)
<213> ORGANISM: Artificial Sequence
<220> FEATURE:
<223> OTHER INFORMATION: Oligomeric Compound

<400> SEQUENCE: 87
gtgatgattt cagctaacat                                          20

<210> SEQ ID NO 88
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 88
gaatattttg gtatctgatt                                          20

<210> SEQ ID NO 89
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 89
atttgaatat tttggtatct                                          20

<210> SEQ ID NO 90
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 90
ttccatttga atattttggt                                          20

<210> SEQ ID NO 91
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 91
atatttccat ttgaatattt                                          20

<210> SEQ ID NO 92
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 92
tttttgatat ttccatttga                                          20

<210> SEQ ID NO 93
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 93
gcactttgtg gtgccaaggc                                          20

```
<210> SEQ ID NO 94
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 94
gcactttgtg gtaccaaggt                                               20

<210> SEQ ID NO 95
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 95
gcattgccac tcccattctt                                               20

<210> SEQ ID NO 96
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 96
aggaccccgg agtaggcggc                                               20

<210> SEQ ID NO 97
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 97
gacctattga gccaggtgac                                               20

<210> SEQ ID NO 98
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 98
gtagctgctt ttccaccttg                                               20

<210> SEQ ID NO 99
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 99
agctgctttt ccaccttgga                                               20

<210> SEQ ID NO 100
<211> LENGTH: 20
<212> TYPE: DNA
<213> ORGANISM: Artificial Sequence
<220> FEATURE:
<223> OTHER INFORMATION: Oligomeric Compound
```

```
<400> SEQUENCE: 100
tggagctcag agactcagcc                                               20

<210> SEQ ID NO 101
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 101
gctgcatcca tgtcatcagc                                               20

<210> SEQ ID NO 102
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 102
acacactaga agtgagctta                                               20

<210> SEQ ID NO 103
<211> LENGTH: 2160
<212> TYPE: DNA
<213> ORGANISM: M. musculus

<400> SEQUENCE: 103
ggcgccctgc tctcccggcg gggcggcgga gggggcgggc tggccggcgc acggtgatgt    60
ggcgggactc tttgtgcact gcggcaggat acgcgcttgg gcgtcgggac gcggctgcgc   120
tcagctctct cctctcggaa gctgcagcca tgatggaagt ttgagagttg agccgctgtg   180
aggccaggcc cggcgcaggc gagggagatg agagacggcg gcggccacgg cccagagccc   240
ctctcagcgc ctgtgagcag ccgcggggcc agcgccctcg gggagccggc cgggcggcgg   300
cggcggcagc ggcggcgggc ctcgcctcct cgtcgtctgt tctaaccggg cagcttctga   360
gcagcttcgg agagagacgg tggaagaagc cgtgggctcg agcggagcc ggcgcaggct    420 cggcggctgc acctcccgct cctggagcgg gggggagaag cggcggcggc ggccgcggct   480
ccggggaggg ggtcggagtc gcctgtcacc attgccaggg ctgggaacgc cggagagttg   540
ctctctcccc ttctcctgcc tccaacacgg cggcggcggc ggcggcacgt ccagggaccc   600 gggcggtgt taagcctccc gtccgccgcc gccgcacccc cctggcccg ggctccggag     660 gccgccggag gaggcagccg ctgcgaggat tatccgtctt ctccccattc cgctgcctcg   720
gctgccaggc ctctggctgc tgaggagaag caggcccagt tctgcaacc atccagcagc    780 cgccgcagca gccattaccc ggctgcggtc cagggccaag cggcagcaga gcgaggggca   840
tcagcgaccg ccaagtccag agccatttcc atcctgcaga agaagcctcg ccaccagcag   900
cttctgccat ctctctcctc cttttttcttc agccacaggc tcccagacat gacagccatc   960
atcaaagaga tcgttagcag aaacaaaagg agatatcaag aggatggatt cgacttagac  1020
ttgacctata tttatccaaa tattattgct atgggatttc ctgcagaaag acttgaaggt  1080
gtatacagga acaatattga tgatgtagta aggttttggg attcaaagca taaaaaccat  1140
tacaagatat acaatctatg tgctgagaga cattatgaca ccgccaaatt taactgcaga  1200
gttgcacagt atcctttga agaccataac ccaccacagc tagaacttat caaacccttc  1260
tgtgaagatc ttgaccaatg gctaagtgaa gatgacaatc atgttgcagc aattcactgt  1320
```

```
aaagctggaa agggacggac tggtgtaatg atttgtgcat atttattgca tcggggcaaa      1380 ttttaaagg cacaagaggc cctagatttt tatggggaag taaggaccag agacaaaaag      1440
ggagtcacaa ttcccagtca gaggcgctat gtatattatt atagctacct gctaaaaaat      1500
cacctggatt acagacccgt ggcactgctg tttcacaaga tgatgtttga aactattcca      1560
atgttcagtg gcggaacttg caatcctcag tttgtggtct gccagctaaa ggtgaagata      1620
tattcctcca attcaggacc cacgcggcgg aggacaagt tcatgtactt tgagttccct      1680
cagccattgc ctgtgtgtgg tgatatcaaa gtagagttct ccacaaaca gaacaagatg      1740 ctcaaaaagg acaaaatgtt tcactttggg gtaaatacgt tcttcatacc aggaccagag      1800
gaaacctcag aaaaagtgga aaatggaagt ctttgtgatc aggaaatcga tagcatttgc      1860
agtatagagc gtgcagataa tgacaaggag tatcttgtac tcaccctaac aaaaaacgat      1920
cttgacaaag caaacaaaga caaggccaac cgatacttct ctccaaattt taaggtgaaa      1980
ctatacttta caaaaacagt agaggagcca tcaaatccag aggctagcag ttcaacttct      2040
gtgactccag atgttagtga caatgaacct gatcattata gatattctga caccactgac      2100
tctgatccag agaatgaacc ttttgatgaa gatcagcatt cacaaattac aaaagtctga      2160

<210> SEQ ID NO 104
<211> LENGTH: 986
<212> TYPE: DNA
<213> ORGANISM: M. musculus

<400> SEQUENCE: 104
ttgaattaca tcttagccca gaagcccgac cggctcagga cgaaggaact cgcggagctg       60
gaggatgagc tctgcaaaact gacgtgtgac tgcactggcc aggtggagc catacaggta      120 gcttctgcag gttcgaagtt cccggttcc tctccgaccg aggagaaacc actgccggcc      180
gcctgccaga cttttctgtt ccacgggcag ctcgtagtga accggccact gactcttcaa      240
gaccagcaga cgtttgcgcg ctcggtgggt ctcaagtggc gcagggtggg gcgctccctg      300
cagcgtaact gtcgggcact gagagatcct gccctcgact cgctgcccta cgagtatgag      360
cgtgatgggc tatacgagca ggccttccag ctgctgcgcc gtttcatgca agccgagggc      420
cgccgtgcca cactgcagcg cctggtggag gcgctggagg agaacgaact cactagtcta      480
gcagaggatc tgttgggcca ggcggagccg gatggcggcc tggcctaagt ctagtactgt      540
ggggaagggc ggccaaccag cagttcagtg tttgaaaccc acgggtggct gttggggtat      600 tttttaccg ctgatgttgc tactgctgac cactttccat ctactggact tggagagcat      660
acgcacgccc cacctagctg agctgctgga gtgcaactaa ctgcccctcc ccccgccccc      720
caggagccag gcaagcagcg caggggtaaa tcactgatga tcatacaaaa agaggacttg      780
ctgcaaagac cctctaagta cccggacctt ctgaaaccta gctcaaggtg ctacaaaaac      840
tgtcgggagc aggatgcacg attttcccg cccttggcat atactcatcg tgggaccgaa      900
gcaccttgtc tgcagcgata ataaaatgta actcttttac agacatgcgg agatgctgag      960
gtctagacct ggttgggtt agtcac                                           986

<210> SEQ ID NO 105
<211> LENGTH: 4788
<212> TYPE: DNA
<213> ORGANISM: H. sapiens

<400> SEQUENCE: 105
tttttagaaa aaaaaatat atttccctcc tgctccttct gcgttcacaa gctaagttgt       60
```

```
ttatctcggc tgcggcggga actgcggacg gtggcgggcg agcggctcct ctgccagagt    120
tgatattcac tgatggactc caaagaatca ttaactcctg gtagagaaga aaaccccagc    180
agtgtgcttg ctcaggagag gggagatgtg atggacttct ataaaaccct aagaggagga    240
gctactgtga aggtttctgc gtcttcaccc tcactggctc tcgcttctca atcagactcc    300
aagcagcgaa gacttttggt tgattttcca aaaggctcag taagcaatgc gcagcagcca    360
gatctgtcca aagcagtttc actctcaatg ggactgtata tggagagac  agaaacaaaa    420 gtgatgggaa atgacctggg attcccacag cagggccaaa tcagccttcc ctcggggga    480 acagacttaa agcttttgga agaaagcatt gcaaacctca ataggtcgac cagtgttcca    540 gagaaccccca agagttcagc atccactgct gtgtctgctg cccccacaga aaggagttt    600 ccaaaaactc actctgatgt atcttcagaa cagcaacatt tgaagggcca gactggcacc    660
aacggtggca atgtgaaatt gtataccaca gaccaaagca cctttgacat tttgcaggat    720
ttggagtttt cttctgggtc cccaggtaaa gagacgaatg agagtccttg agatcagac    780 ctgttgatag atgaaaactg tttgctttct cctctggcgg gagaagacga ttcattcctt    840
ttggaaggaa actcgaatga ggactgcaag cctctcattt taccggacac taaacccaaa    900
attaaggata atggagatct ggttttgtca agccccagta atgtaacact gccccaagtg    960
aaaacagaaa aagaagattt catcgaactc tgcacccctg gggtaattaa gcaagagaaa   1020
ctgggcacag tttactgtca ggcaagcttt cctggagcaa atataattgg taataaaatg   1080
tctgccattt ctgttcatgg tgtgagtacc tctggaggac agatgtacca ctatgacatg   1140
aatacagcat cccttttctca acagcaggat cagaagccta ttttttaatgt cattccacca   1200 attcccgttg gttccgaaaa ttggaatagg tgccaaggat ctggagatga caacttgact   1260
tctctgggga ctctgaactt ccctggtcga acagtttttt ctaatggcta ttcaagcccc   1320
agcatgagac cagatgtaag ctctcctcca tccagctcct caacagcaac aacaggacca   1380
cctcccaaac tctgcctggt gtgctctgat gaagcttcag gatgtcatta tggagtctta   1440
acttgtggaa gctgtaaagt tttcttcaaa agagcagtgg aaggacagca caattaccta   1500
tgtgctggaa ggaatgattg catcatcgat aaaattcgaa gaaaaactg cccagcatgc   1560 cgctatcgaa aatgtcttca ggctggaatg aacctggaag ctcgaaaaac aaagaaaaaa   1620 ataaaggaa ttcagcaggc cactacagga gtctcacaag aaacctctga aaatcctggt   1680
aacaaaacaa tagttcctgc aacgttacca caactcaccc ctaccctggt gtcactgttg   1740
gaggttattg aacctgaagt gttatatgca ggatatgata gctctgttcc agactcaact   1800
tggaggatca tgactacgct caacatgtta ggagggcggc aagtgattgc agcagtgaaa   1860
tgggcaaagg caataccagg tttcaggaac ttacacctgg atgaccaaat gaccctactg   1920
cagtactcct ggatgtttct tatggcattt gctctggggt ggagatcata tagacaatca   1980
agtgcaaacc tgctgtgttt tgctcctgat ctgattatta tgagcagag aatgactcta   2040 ccctgcatgt acgaccaatg taaacacatg ctgtatgttt cctctgagtt acacaggctt   2100
caggtatctt atgaagagta tctctgtatg aaaacccttac tgcttctctc ttcagttcct   2160
aaggacggtc tgaagagcca agagctattt gatgaaatta aatgaccta catcaaagag   2220 ctaggaaaag ccattgtcaa gagggaagga aactccagcc agaactggca gcggttttat   2280
caactgacaa aactcttgga ttctatgcat gaagtggttg aaaatctcct taactattgc   2340
ttccaaacat ttttggataa gaccatgagt attgaattcc ccgagatgtt agctgaaatc   2400
atcaccaatc agataccaaa atattcaaat ggaaatatca aaaaacttct gtttcatcaa   2460
```

```
aagtgactgc cttaataaga atggttgcct taaagaaagt cgaattaata gcttttattg    2520
tataaactat cagtttgtcc tgtagaggtt ttgttgtttt atttttatt gttttcatct     2580 gttgttttgt tttaaatacg cactacatgt ggtttataga gggccaagac ttggcaacag    2640
aagcagttga gtcgtcatca cttttcagtg atgggagagt agatggtgaa atttattagt    2700
taatatatcc cagaaattag aaaccttaat atgtggacgt aatctccaca gtcaaagaag    2760
gatggcacct aaaccaccag tgcccaaagt ctgtgtgatg aactttctct tcatactttt    2820
tttcacagtt ggctggatga aattttctag actttctgtt ggtgtatccc ccccctgtat    2880
agttaggata gcattttga tttatgcatg gaaacctgaa aaaagtttta caagtgtata     2940
tcagaaaagg gaagttgtgc cttttatagc tattactgtc tggttttaac aatttccttt    3000
atatttagtg aactacgctt gctcattttt tcttacataa tttttttattc aagttattgt   3060 acagctgttt aagatgggca gctagttcgt agctttccca aataaactct aaacattaat    3120
caatcatctg tgtgaaaatg ggttggtgct tctaacctga tggcacttag ctatcagaag    3180
accacaaaaa ttgactcaaa tctccagtat tcttgtcaaa aaaaaaaaa aaaaagctca     3240 tattttgtat atatctgctt cagtggagaa ttatataggt tgtgcaaatt aacagtccta    3300
actggtatag agcaccctagt ccagtgacct gctgggtaaa ctgtggatga tggttgcaaa   3360
agactaattt aaaaaataac taccaagagg ccctgtctgt acctaacgcc ctattttgc     3420 aatggctata tggcaagaaa gctggtaaac tatttgtctt tcaggacctt ttgaagtagt    3480
ttgtataact tcttaaaagt tgtgattcca gataaccagc tgtaacacag ctgagagact    3540
tttaatcaga caaagtaatt cctctcacta aactttaccc aaaaactaaa tctctaatat    3600
ggcaaaaatg gctagacacc cattttcaca ttcccatctg tcaccaattg gttaatcttt    3660
cctgatggta caggaaagct cagctactga ttttttgtgat ttagaactgt atgtcagaca   3720
tccatgtttt taaaactaca catccctaat gtgtgccata gagtttaaca caagtcctgt    3780
gaatttcttc actgttgaaa attattttaa acaaaataga agctgtagta gccctttctg    3840
tgtgcacctt accaacttttc tgtaaactca aaacttaaca tatttactaa gccacaagaa   3900
atttgatttc tattcaaggt ggccaaatta tttgtgtaat agaaaactga aaatctaata    3960
ttaaaaatat ggaacttcta atatatttt atatttagtt atagtttcag atatatatca    4020
tattggtatt cactaatctg ggaagggaag ggctactgca gctttacatg caatttatta    4080
aaatgattgt aaaatagctt gtatagtgta aaataagaat gatttttaga tgagattgtt    4140
ttatcatgac atgttatata ttttttgtag gggtcaaaga aatgctgatg gataacctat    4200 atgattata gtttgtacat gcattcatac aggcagcgat ggtctcagaa accaaacagt     4260
ttgctctagg ggaagaggga gatggagact ggtcctgtgt gcagtgaagg ttgctgaggc    4320
tctgacccag tgagattaca gaggaagtta tcctctgcct cccattctga ccaccccttct   4380 cattccaaca gtgagtctgt cagcgcaggt ttagtttact caatctcccc ttgcactaaa    4440
gtatgtaaag tatgtaaaca ggagacagga aggtggtgct tacatcctta aaggcaccat    4500
ctaatagcgg gttactttca catacagccc tcccccagca gttgaatgac aacagaagct    4560
tcagaagttt ggcaatagtt tgcatagagg taccagcaat atgtaaatag tgcagaatct    4620
cataggttgc caataataca ctaattcctt tctatcctac aacaagagtt tatttccaaa    4680
taaaatgagg acatgttttt gttttctttg aatgcttttt gaatgttatt tgttattttc    4740
agtatttggg agaaattatt taataaaaaa acaatcattt gcttttg                  4788
```

<210> SEQ ID NO 106

```
<211> LENGTH: 6322
<212> TYPE: DNA
<213> ORGANISM: R. norvegicus
<220> FEATURE:
<221> NAME/KEY: misc_feature
<222> LOCATION: 24, 3663, 3680, 3684, 3685, 3791, 3805, 3806, 3813,
      3854, 3861, 4162, 4177, 4205, 4206, 4240, 4246, 4247, 4262,
      4283, 4284, 4293, 4295, 4311, 4354, 4358, 4359, 4360, 4398,
      6010, 6011, 6013, 6014, 6065, 6069, 6145, 6161
<223> OTHER INFORMATION: n = A,T,C or G

<400> SEQUENCE: 106
```

| | | |
|---|---|---|
| gacgctgcgg gggtggggga cctncggcgg cacggagtcc cccccgggc tcacattaat | 60 |
| atttgccaat ggactccaaa gaatccttag ctcccctgg tagagacgaa gtccctggca | 120 |
| gtttgcttgg ccaagggagg gggagcgtaa tggactttta taaaagcctg aggggaggag | 180 |
| ctacagtcaa ggtttctgca tcttcgccct cagtggctgc tgcttctcag gcagattcca | 240 |
| agcagcagag gattctcctt gatttctcga aaggctccac aagcaatgtg cagcagcgac | 300 |
| agcagcagca gcagcagcag cagcagcagc agcagcagca gcagcagcag cagcagccag | 360 |
| gcttatccaa agccgtttca ctgtccatgg ggctgtatat gggagagaca gaaacaaaag | 420 |
| tgatggggaa tgacttgggc tacccacagc agggccaact tggcctttcc tctggggaaa | 480 |
| cagactttcg gcttctggaa gaaagcattg caaacctcaa taggtcgacc agcgttccag | 540 |
| agaaccccaa gagttcaacg tctgcaactg ggtgtgctac cccgacagag aaggagtttc | 600 |
| ccaaaactca ctcggatgca tcttcagaac agcaaaatcg aaaaagccag accggcacca | 660 |
| acggaggcag tgtgaaattg tatcccacag accaaagcac cttgacctc ttgaaggatt | 720 |
| tggagttttc cgctgggtcc ccaagtaaag acacaaacga gagtccctgg agatcagatc | 780 |
| tgttgataga tgaaaacttg ctttctcctt tggcgggaga agatgatcca ttccttctcg | 840 |
| aagggaacac gaatgaggat tgtaagcctc ttattttacc ggacactaaa cctaaaatta | 900 |
| aggatactgg agatacaatc ttatcaagtc ccagcagtgt ggcactaccc caagtgaaaa | 960 |
| cagaaaaaga tgatttcatt gaactttgca cccccgggt aattaagcaa gagaaactgg | 1020 |
| gcccagttta ttgtcaggca agcttttctg gacaaatat aattggtaat aaaatgtctg | 1080 |
| ccatttctgt tcatggtgtg agtacctctg gaggacagat gtaccactat gacatgaata | 1140 |
| cagcatccct ttctcagcag caggatcaga agcctgttt taatgtcatt ccaccaattc | 1200 |
| ctgttggttc tgaaaactgg aataggtgcc aaggctccgg agaggacagc ctgacttcct | 1260 |
| tgggggctct gaacttccca ggccggtcag tgttttctaa tgggtactca agccctggaa | 1320 |
| tgagaccaga tgtaagctct cctccatcca gctcgtcagc agccacggga ccacctccca | 1380 |
| agctctgcct ggtgtgctcc gatgaagctt caggatgtca ttacgggtg ctgacatgtg | 1440 |
| gaagctgcaa agtattcttt aaaagagcag tggaaggaca gcacaattac ctttgtgctg | 1500 |
| gaagaaacga ttgcatcatt gataaaattc gaaggaaaaa ctgcccagca tgccgctatc | 1560 |
| ggaaatgtct tcaggctgga atgaaccttg aagctcgaaa aacaaagaaa aaaatcaaag | 1620 |
| ggattcagca agccactgca ggagtctcac aagacacttc ggaaaatcct aacaaaacaa | 1680 |
| tagttcctgc agcattacca cagctcaccc ctaccttggt gtcactgctg gaggtgattg | 1740 |
| aacccgaggt gttgtatgca ggatatgata gctctgttcc agattcagca tggagaatta | 1800 |
| tgaccacact caacatgtta ggtgggcgtc aagtgattgc agcagtgaaa tgggcaaagg | 1860 |
| cgatactagg cttgagaaac ttacacctcg atgaccaaat gaccctgcta cagtactcat | 1920 |
| ggatgttct catggcattt gccttgggtt ggagatcata cagacaatca agcggaaacc | 1980 |
| tgctctgctt tgctcctgat ctgattatta atgagcagag aatgtctcta ccctgcatgt | 2040 |

```
atgaccaatg taaacacatg ctgtttgtct cctctgaatt acaaagattg caggtatcct    2100
atgaagagta tctctgtatg aaaaccttac tgcttctctc ctcagttcct aaggaaggtc    2160
tgaagagcca agagttattt gatgagattc gaatgactta tatcaaagag ctaggaaaag    2220
ccatcgtcaa aagggaaggg aactccagtc agaactggca acggttttac caactgacaa    2280
agcttctgga ctccatgcat gaggtggttg agaatctcct tacctactgc ttccagacat    2340
ttttggataa gaccatgagt attgaattcc cagagatgtt agctgaaatc atcactaatc    2400
agataccaaa atattcaaat ggaaatatca aaaagcttct gtttcatcaa aaatgactgc    2460
cttactaaga aaggttgcct taaagaaagt tgaatttata gcttttactg tacaaactta    2520
tcaatttgtc ttgtagatgt tttgttgttc ttttgtttc tgtcttgttt tgttttaaac    2580
acgcagtaca tgtggtttat agagggccaa gacttggcga cagaagcagt tgagtcaaca    2640
ctctgaagtg atgacacagc acacagtgaa gtgtattgtt ggtgtatcac agaaactaac    2700
agttacgtgg aggcatggcc actgtcagag agggaccgca cctaaaccac cgtgcccaag    2760
tccatgtggt tcaactttct gactcagaac tttacagttg ctgggtaaa actttctaga    2820
cttttctgttg gtgtattttt cccatgtata gttaggatgt tattttgatt tatgcatgca    2880
aacctgaaaa aagtttacaa gtgtatatca gaaagggaa gttgtgcctt ttatagctat    2940
tactgtctgg ttttaacaat ttcctttata ttcagtgaac tatgcttgct cgtttctctt    3000
caataatttt tgtattccag ttattgtaca gctgtttaag atgggcagct gcttcacagc    3060
tttcctagac gctaacatta atttccgtgt gaaaatgggc cggtgcttct acctgttgg    3120
caccagctat cagaagacca cagaaattga ctcagatctc cagtattctt gttaaaaagc    3180
tcttactctg tatatatctg cttccatgga gaattacata ggctgagcag attacatagg    3240
ctgagcagat taaccgtcct aactggtgta gagcacctag tccagtgacc ttctgggtaa    3300
accgtggatg atggttacag aagactggtg ggaaaacagt aactaccaaa aggcccctttt   3360
ccatctaatg caccatctct tcaatgggga gatagcaacc aagcccgtaa atcagctctt    3420
tcaggacctt ctggagtggt ttgcataaca ttttaaaatg tattattcca gatagccagc    3480
tctgataaag ccgagagatt gtttaatcag accaagtaac ttctctcatt aaacttaccc    3540
ccaactaaat cgctaataca gcaagaatgg ctagacaccc atttttcacat ctcacccgca    3600
ccgattggtc tagctctcat ggtggtcagg agaatcagct actgatttt gttacttaga    3660
atnttcagga ctcgcattn tccnnctaca catccctaca tgtgccatag aatttaacac    3720
aagtcctgtg aacttcttca cattgagaat tatcatttta aacaaaacag aagcagtagt    3780
agccctttct ntgtgcacct taccnncttt ctntgactca aagcttaata tgcttactaa    3840
gccacaagaa atcngatttc nacttaaagg cgccaaatta tttgtgtaat agaaaaactg    3900
aaaatctaat attaaaaata tgaaacttct aatatatttt tatatttagt tatagtttcg    3960
atatatatca tatcggtatt cactgatctt gggaagga aagggctact gcagctttac     4020
atgcaattta ttaactgact gtaaaatagc tgtatagtaa taagaatgac ttttagtgag    4080
attgctttat catgacatgt tatatatttt tcgtagggt caaagaaata ttgatggata    4140
tgatagccta tatgattttaa tngtatataa agcatncaa acaggcctta acgcgtcttg     4200
gaaannaaaa tacctttgtt ctaagctagg gaagggagcn ggagannggc cccgtgtgta    4260
tnggaggttc cgaggctcgg atnnaagaga tcnanagggg atctaattcc ntacctccat    4320
ctaattacct caccacccat gatcctgtca gtgnaggnnn ggttattaaa tccccgtta    4380
tactaatata aataggganag aagggtggcg ctcacgtctg ttccaggcgc cgcagtagca    4440
```

```
gggttatttt ccatgcagcc tcccgacaag gttagcagag ggaggctttg gcaagtttgg      4500
cgtggcgtgc atagaggcac cagcaacatg taaacctaaa gagcccatag gaagccaaga      4560
atacactaat cctccccacc cttcaatagt ccatttccaa gtaagatgag gacatgctta      4620
tgttttcttt gaatgctttt agaatgttgt tattttcagt attttgcaga aattatttaa      4680
taaaaaagta taatttgaat tctctctaaa agggattgtt cagtttgtaa tggtttaaat      4740
tggtctcaaa gtactttaag ataattgtaa cccagctgga tgtgaaattt atggtgccta      4800
agaaatacca cttgaatatt atcaagacag tgttaagttt taaaatgagc ttctcaaaaa      4860
tagattattg tacatttatg gaatgttata tggttaaacc caaaaagca catcacacat       4920 aaatctgctt tcagcttggc tttcaaaaat agagctccaa aaacgaaaaa ggagaagaaa      4980
aagtatatat atgcgttgtt attaacagaa ggcaacagac attcataaaa ctactaccga      5040
agctttcctt gaagcgtata aagagccatg ctcctttagt atgtggggaa gaagagagcc      5100
gtcatagttt cgagtacaga gagaagatgc ggtactgtct ccgtgtgtgg cttcataccg      5160
ttcctaacta tttaggttta taataacttc agtgagactc ggtgacatgc ctgtatgact      5220
catgaccgat cttgaaagat atctttaatt actggtagga caaaagggac actctggtta      5280
ttttaggcct tggcttggga tactgtatat ccagaagaaa ggagacagga aacttgggga      5340
agggaaggga acctaggaag cactgccttc tgtaggaaaa aacacaccaa taagtgagag      5400
tacccaaagg gacaaggcca cacagtgtgg ggtctaagga tgagtcaggg tgagctctgg      5460
tgggcatgga gaagccagca actccagtgc tacagagcag ggcagggcag ggatgggaca      5520
agatggatgc ggatcccagt cccagtagtt tgctccctct tatttaccat gggatgaacc      5580
atggagtatt gatctgtcag cactcaagga tcatggagct tgagattccg gttggtcacc      5640
ccaacggtaa gctgagattg aatgtgtttc ttatgtgccg gtttcagtgt tagaaggcga      5700
aacagagtgt acagaagaca ctgcaaaccg gtcagatgaa agtcttctca ttcccaaact      5760
attttcagtc agcctgctct atcaggactg gtgaccagct gctaggacag ggtcggcgct      5820
tctgtctaga atatgcctga aaggatttta ttttctgata aatggctgta tgaaaatacc      5880
ctcctcaata acctgcttaa ctacatagag atttcagtgt gtcaatattc tattttgtat      5940
attaaacaaa ggctatataa tggggacaaa tctatattat actgtgtatg gcattattaa      6000
gaagcttttn nannattttt tatcacagta attttaaat gtgtaaaaaa ttaaaaatta      6060
gtgantccng tttaaaaata aaagttgtag tttttttattc atgctgaata acctgtagtt      6120
taaaaatccg tctttctacc tacanagtga aatgtcagac ngtaaaattt tgtgtggaaa      6180
tgtttaactt ttattttct ttaaatttgc tgtcttggta ttaccaaacc acacattgta      6240
ctgaattggc agtaaatgtt agtcagccat ttacagcaat gccaaatatg gataaacatc      6300
ataataaaat atctgctttt tc                                              6322
```

<210> SEQ ID NO 107
<211> LENGTH: 2575
<212> TYPE: DNA
<213> ORGANISM: M. musculus

<400> SEQUENCE: 107

```
ggaagttaat atttgccaat ggactccaaa gaatccttag ctcccctgg tagagacgaa        60 gtccccagca gtttgcttgg ccgggggagg ggaagcgtga tggacttgta taaaccctg       120 aggggtggag ctacagtcaa ggtttctgcg tcttcaccct cagtggctgc tgcttctcag      180
gcagattcca agcagcagag gattctcctt gattttcaa aaggctcagc aagcaatgca      240
```

```
cagcagcagc agcagcagca gcagccgcag ccagatttat ccaaagccgt ttcactgtcc    300
atgggactgt atatgggaga gaccgaaaca aaagtgatgg ggaatgactt gggctaccca    360
cagcagggcc agcttggcct ctcctctggg gaaacagact ttcggcttct ggaagaaagc    420
attgcaaacc tcaataggtc gaccagccgt ccagagaatc ccaagagttc aacacctgca    480
gctgggtgtg ctaccccgac agagaaggag tttccccaga ctcactctga tccatcttca    540
gaacagcaaa atagaaaaag ccagcctggc accaacggtg gcagtgtgaa attgtatacc    600
acagaccaaa gcacctttga catcttgcag gatttggagt tttctgccgg gtccccaggt    660
aaagagacaa acgagagtcc ttggaggtca gacctgttga tagatgaaaa cttgctttct    720
cctttggcgg gagaagatga tccattcctt ctggaagggg acgtgaatga ggattgcaag    780
cctcttattt taccggacac taaacctaaa attcaggata ctggagatac aatcttatca    840
agccccagca gtgtggcact gccccaagtg aaaacagaga aagatgattt cattgagctt    900
tgcaccccctg ggtaattaa gcaagagaaa ctgggcccgg tttattgcca ggcaagcttt    960
tctgggacaa atataattgg gaataaaatg tctgccattt ctgttcatgg cgtgagtacc   1020
tctggaggac agatgtacca ctatgacatg aatacagcat ccctttctca gcagcaggat   1080
cagaagcctg ttttttaatgt cattccacca attcctgttg gttctgaaaa ctggaatagg   1140
tgccaagggt ctgagagga caacctgact tccttggggg ctatgaactt cgcaggccgc   1200
tcagtgtttt ctaatggata ttcaagccct ggaatgagac cagatgtgag ttctcctccg   1260
tccagctcct ccacagcaac gggaccacct cccaaactct gcctggtgtg ctccgatgaa   1320
gcttcggtat gccattatgg ggtgctgacg tgtggaagct gtaaagtctt cttttaaaaga   1380
gcagtggaag gacagcacaa ttacctttgt gctggaagaa atgattgcat cattgataaa   1440
attcgaagaa aaaactgtcc agcatgccgc tatcgaaaat gtcttcaagc tggaatgaac   1500
ctggaagctc gaaaaacgaa gaaaaaaatt aaggaattca gcaagccac tgcaggagtc   1560
tcacaagaca cttctgaaaa cgctaacaaa acaatagttc ctgccgcgct gccacagctt   1620
acccctaccc tggtgtcact gctggaggtg atcgagcctg aggtgttata tgcaggatat   1680
gacagctctg ttccagactc agcatggaga attatgacca cgctcaacat gttaggtggg   1740
cgccaagtga ttgccgcagt gaaatgggca aaggcgatac caggattcag aaacttacac   1800
ctggatgacc aaatgacccct tctacagtac tcatggatgt ttctcatggc atttgccctg   1860
ggttggagat catacagaca agcaagtgga aacctgctat gctttgctcc tgatctgatt   1920
attaatgagc agagaatgac tctaccctgc atgtatgacc aatgtaaaca catgctgttt   1980
atctccactg aattacaaag attgcaggta tcctatgaag agtatctctg tatgaaaacc   2040
ttactgcttc tctcctcagt tcctaaggaa ggtctgaaga gccaagagtt atttgatgag   2100
attcgaatga cttatatcaa agagctagga aaagccattg tcaaaaggga aggaaactcc   2160
agtcagaatt ggcagcggtt ttatcaactg acaaaacttt tggactccat gcatgatgtg   2220
gttgaaaatc tccttagcta ctgcttccaa acattttttgg ataagtccat gagtattgaa   2280
ttcccagaga tgttagctga aatcatcact aatcagatac caaaatactc aaatggaaat   2340
atcaaaaagc ttctgtttca tcagaaatga ctgccttact aagaaaggct gccttaaaga   2400
aagttgaatt tatagctttt actgtacaaa cttatcaact tgtcttgtag atgttttgtc   2460
gttcttttttg tttgtcttgt ttgttttcta tacgcactac atgtggtctc tagagggcca   2520
agacttggca acagaagcag atgagccatc acttttcagt gacaggaaag cagac        2575
```

<210> SEQ ID NO 108
<211> LENGTH: 2034
<212> TYPE: DNA
<213> ORGANISM: H. sapiens

<400> SEQUENCE: 108

| | | | | | |
|---|---|---|---|---|---|
| ggatctggca | gcgccgcgaa | gacgagcggt | caccggcgcc | cgacccgagc | gcgcccagag | 60 |
| gacggcgggg | agccaagccg | accccgagc | agcgccgcgc | gggccctgag | gctcaaaggg | 120 |
| gcagcttcag | gggaggacac | cccactggcc | aggacgcccc | aggctctgct | gctctgccac | 180 |
| tcagctgccc | tcggaggagc | gtacacacac | accaggactg | cattgcccca | gtgtgcagcc | 240 |
| cctgccagat | gtgggaggca | gctagctgcc | cagaggcatg | cccccctgcc | agccacagcg | 300 |
| accccctgctg | ctgttgctgc | tgctgctggc | ctgccagcca | caggtcccct | ccgctcaggt | 360 |
| gatggacttc | ctgtttgaga | gtggaagct | ctacggtgac | cagtgtcacc | acaacctgag | 420 |
| cctgctgccc | cctcccacgg | agctggtgtg | caacagaacc | ttcgacaagt | attcctgctg | 480 |
| gccggacacc | cccgccaata | ccacggccaa | catctcctgc | cctggtacc | tgccttggca | 540 |
| ccacaaagtg | caacaccgct | tcgtgttcaa | gagatgcggg | cccgacggtc | agtgggtgcg | 600 |
| tggaccccgg | gggcagcctt | ggcgtgatgc | ctcccagtgc | cagatggatg | cgaggagat | 660 |
| tgaggtccag | aaggaggtgg | ccaagatgta | cagcagcttc | caggtgatgt | acacagtggg | 720 |
| ctacagcctg | tccctggggg | ccctgctcct | cgccttggcc | atcctggggg | gcctcagcaa | 780 |
| gctgcactgc | acccgcaatg | ccatccacgc | gaatctgttt | gcgtccttcg | tgctgaaagc | 840 |
| cagctccgtg | ctggtcattg | atgggctgct | caggaccccgc | tacagccaga | aaattggcga | 900 |
| cgacctcagt | gtcagcacct | ggctcagtga | tgagcggtg | gctggctgcc | gtgtggccgc | 960 |
| ggtgttcatg | caatatggca | tcgtggccaa | ctactgctgg | ctgctggtgg | agggcctgta | 1020 |
| cctgcacaac | ctgctgggcc | tggccaccct | ccccgagagg | agcttcttca | gcctctacct | 1080 |
| gggcatcggc | tggggtgccc | ccatgctgtt | cgtcgtccccc | tgggcagtgg | tcaagtgtct | 1140 |
| gttcgagaac | gtccagtgct | ggaccagcaa | tgacaacatg | ggcttctggt | ggatcctgcg | 1200 |
| gttccccgtc | ttcctggcca | tcctgatcaa | cttcttcatc | ttcgtccgca | tcgttcagct | 1260 |
| gctcgtggcc | aagctgcggg | cacggcagat | gcaccacaca | gactacaagt | tccggctggc | 1320 |
| caagtccacg | ctgaccctca | tccctctgct | gggcgtccac | gaagtggtct | ttgccttcgt | 1380 |
| gacggacgag | cacgcccagg | gcaccctgcg | ctccgccaag | ctcttcttcg | acctcttcct | 1440 |
| cagctccttc | cagggcctgc | tggtggctgt | cctctactgc | ttcctcaaca | aggaggtgca | 1500 |
| gtcggagctg | cggcggcgtt | ggcaccgctg | gcgcctgggc | aaaagtgctat | gggaggagcg | 1560 |
| gaacaccagc | aaccagggg | cctcatcttc | gccccggccac | ggccctccca | gcaaggagct | 1620 |
| gcagtttggg | aggggtggtg | gcagccagga | ttcatctgcg | gagacccct | tggctggtgg | 1680 |
| cctcccctaga | ttggctgaga | gccccttctg | aaccctgctg | ggaccccagc | tagggctgga | 1740 |
| ctctggcacc | cagaggcgtc | gctggacaac | ccagaactgg | acgcccagct | gaggctgggg | 1800 |
| gcggggagc | caacagcagc | ccccacctac | ccccaccccc | cagtgtggct | gtctgcgaga | 1860 |
| ttgggcctcc | tctccctgca | cctgccttgt | ccctggtgca | gaggtgagca | gaggagtcca | 1920 |
| gggcgggagt | gggggctgtg | ccgtgaactg | cgtgccagtg | tccccacgta | tgtcggcacg | 1980 |
| tcccatgtgc | atggaaatgt | cctccaacaa | taaagagctc | aagtggtcac | cgtg | 2034 |

<210> SEQ ID NO 109
<211> LENGTH: 1875
<212> TYPE: DNA
<213> ORGANISM: R. norvegicus

<400> SEQUENCE: 109

```
gaattcgcgg ccgccgccgg gccccagatc ccagtgcgcg aggagcccag tcctagaccc      60
agcaacctga ggagaggtgc acacacccccc aaggacccag gcacccaacc tctgccagat    120
gtggggggt ggctacccag aggcatgctc ctcacccagc tccactgtcc ctacctgctg     180
ctgctgctgg tggtgctgtc atgtctgcca aaggcaccct ctgcccaggt aatggacttt     240
ttgtttgaga agtggaagct ctatagtgac cagtgccacc acaacctaag cctgctgccc     300
ccacctactg agctggtctg caacagaact ttcgacaagt actcctgctg gcctgacacc     360
cctcccaaca ccactgccaa catttcctgc ccctggtacc taccttggta ccacaaagtg     420
cagcaccgcc tagtgttcaa gaggtgtggg cctgatgggc agtgggttcg agggccacgg     480
gggcagtcat ggcgcgacgc ctcccaatgt cagatggatg atgacgagat cgaggtccag     540
aaggggtag ccaagatgta tagcagctac caggtgatgt acactgtggg ctacagtctg      600
tccctggggg ccttgctcct ggcgctggtc atcctgctgg gcctcaggaa gctgcactgc     660
acccggaact acatccacgg gaacctgttc gcgtccttcg tgctcaaggc tggctctgtg     720
ctggtcattg attggctgct caagacacgc tatagccaga agattggaga tgacctcagt     780
gtgagcgtct ggctcagtga tggggcggtg gctggctgca gagtggccac agtgatcatg     840
cagtacggca tcatagccaa ctactgctgg ttgctggtga agggtgtgta cctgtacagc     900
ctgctgagca tcaccacctt ctcggagaag agcttcttct ccctctatct gtgcatcggc     960
tggggatctc ccctgctgtt tgtcatcccc tgggtggtgg tcaagtgtct gtttgagaat    1020
gtccagtgct ggaccagcaa tgacaatatg ggattctggt ggatcctgcg tatccctgta    1080
ctcctggcca tactgatcaa tttttttcatc tttgtccgca tcattcatct tcttgtggcc   1140
aagctgcgtg cccatcagat gcactatgct gattacaagt tccggctagc caggtccacg    1200
ctgacccctca ttcctctgct gggagtccac gaagtggtct ttgcctttgt gactgatgag   1260
catgcccagg gcaccctgcg ctccaccaag ctcttttttg acctgttctt cagctccttt    1320
cagggtctgc tggtggctgt tctctactgt ttcctcaaca aggaggtgca ggcagagcta    1380
ctgcggcgtt ggaggcgatg gcaagaaggc aaagctcttc aggaggaaag gatggccagc    1440
agccatggca gccacatggc cccagcaggg acttgtcatg gtgatccctg tgagaaactt    1500
cagcttatga gtgcaggcag cagcagtggg actggctgtg agccctctgc gaagacctca    1560
ttggccagta gtctcccaag gctggctgac agccccacct gaatctccac tggactccag    1620
ccaagttgga ttcagaaagg gcctcacaag acaacccaga aacagatgcc tggccaaggc    1680
tgaagaggca aagcagcaag acagcagctt gtactatcca cactcccta  acctgtcctg    1740
gccgggtaca ggccacattg atggagtagg ggctggatat gatggagtag ccatgctatg    1800
aactatgggt gttcccatga gtgttgccat gttccatgca cacagatatg accttcagta    1860
aagagctccc gtagg                                                    1875
```

<210> SEQ ID NO 110
<211> LENGTH: 2439
<212> TYPE: DNA
<213> ORGANISM: H. sapiens

<400> SEQUENCE: 110

```
ctccgggaac gccagcgccg cggctgccgc ctctgctggg gtctaggctg tttctctcgc      60
gccaccactg gccgccggcc gcagctccag gtgtcctagc cgcccagcct cgacgccgtc    120
ccgggacccc tgtgctctgc gcgaagccct ggccccgggg gccggggcat gggccagggg    180
```

```
cgcggggtga agcggcttcc cgcggggccg tgactgggcg ggcttcagcc atgaagaccc    240
tcatagccgc ctactccggg gtcctgcgcg gcgagcgtca ggccgaggct gaccggagcc    300
agcgctctca cggaggacct gcgctgtcgc gcgaggggtc tgggagatgg ggcactggat    360
ccagcatcct ctccgccctc caggacctct tctctgtcac ctggctcaat aggtccaagg    420
tggaaaagca gctacaggtc atctcagtgc tccagtgggt cctgtccttc cttgtactgg    480
gagtggcctg cagtgccatc ctcatgtaca tattctgcac tgattgctgg ctcatcgctg    540
tgctctactt cacttggctg gtgtttgact ggaacacacc caagaaaggt ggcaggaggt    600
cacagtgggt ccgaaactgg gctgtgtggc gctactttcg agactacttt cccatccagc    660
tggtgaagac acacaacctg ctgaccacca ggaactatat ctttggatac cacccccatg    720
gtatcatggg cctgggtgcc ttctgcaact tcagcacaga ggccacagaa gtgagcaaga    780
agttcccagg catacggcct tacctggcta cactggcagg caacttccga atgcctgtgt    840
tgagggagta cctgatgtct ggaggtatct gccctgtcag ccgggacacc atagactatt    900
tgctttcaaa gaatgggagt ggcaatgcta tcatcatcgt ggtcgggggt gcggctgagt    960
ctctgagctc catgcctggc aagaatgcag tcacgctgcg gaaccgcaag ggcttgtga   1020
aactggccct gcgtcatgga gctgacctgg ttcccatcta ctcctttgga gagaatgaag   1080
tgtacaagca ggtgatcttc gaggagggct cctggggccg atgggtccag aagaagttcc   1140
agaaatacat tggtttcgcc ccatgcatct tccatggtcg aggcctcttc cctccgaca   1200
cctgggggct ggtgccctac tccaagccca tcaccactgt tgtgggagag cccatcacca   1260
tccccaagct ggagcaccca acccagcaag acatcgacct gtaccacacc atgtacatgg   1320
aggccctggt gaagctcttc gacaagcaca agaccaagtt cggcctcccg gagactgagg   1380
tcctggaggt gaactgagcc agccttcggg gccaactccc tggaggaacc agctgcaaat   1440
cacttttttg ctctgtaaat ttggaagtgt catgggtgtc tgtgggttat ttaaaagaaa   1500
ttataacaat tttgctaaac cattacaatg ttaggtcttt tttaagaagg aaaaagtcag   1560
tatttcaagt tcttttcactt ccagcttgcc ctgttctagg tggtggctaa atctgggcct   1620
aatctgggtg gctcagctaa cctctcttct tcccttcctg aagtgacaaa ggaaactcag   1680
tcttcttggg gaagaaggat tgccattagt gacttggacc agttagatga ttcactttt   1740
gcccctaggg atgagaggcg aaagccactt ctcatacaag ccccctttatt gccactaccc   1800
cacgctcgtc tagtcctgaa actgcaggac cagtttctct gccaagggga ggagttggag   1860
agcacagttg ccccgttgtg tgagggcagt agtaggcatc tggaatgctc cagtttgatc   1920
tcccttctgc caccctacc tcaccccctag tcactcatat cggagcctgg actggcctcc   1980
aggatgagga tggggtggc aatgacaccc tgcagggaa aggactgccc cccatgcacc   2040
attgcaggga ggatgccgcc accatgagct aggtggagta actggttttt cttgggtggc   2100
tgatgacatg gatgcagcac agactcagcc ttggcctgga gcacatgctt actggtggcc   2160
tcagtttacc ttccccagat cctagattct ggatgtgagg aagagatccc tcttcagaag   2220
gggcctggcc ttctgagcag cagattagtt ccaaagcagg tggccccga acccaagcct   2280
cacttttctg tgccttcctg aggggttgg gccgggagg aaacccaacc ctctcctgtg   2340
tgttctgtta tctcttgatg agatcattgc accatgtcag acttttgtat atgccttgaa   2400
aataaatgaa agtgagaatc caaaaaaaaa aaaaaaaa                           2439
```

<210> SEQ ID NO 111
<211> LENGTH: 31737

```
<212> TYPE: DNA
<213> ORGANISM: R. norvegicus
<220> FEATURE:
<221> NAME/KEY: misc_feature
<222> LOCATION: (26994)...(27191)
<223> OTHER INFORMATION: n = A,T,C or G

<400> SEQUENCE: 111
```

| | | | | | |
|---|---|---|---|---|---|
| aaccccccac | aaaaacatgg | tacagtccgg | ggcggaccct | tttgcccgc | cctatagcgt | 60 |
| catgacccgc | cccgttgtga | ggttataaag | cgcgcgcgcg | cgcggcggcg | ctaggcgccg | 120 |
| tggccgcgct | tcgctagctt | tctgattgcc | tagggtggca | gcggctacct | acctcggatc | 180 |
| tcgacctgct | gccaccacgg | cctgagcgct | gtccctcggc | tcccggagct | cagcgcgaag | 240 |
| ccctggcccc | ggcggctggg | gcatggatca | ggggcgctgc | gtgaggcggc | ttcctgcacg | 300 |
| gccgtgacgt | gcaccggctt | cagcatgaag | accctcatcg | ctgcctactc | cggggtcctg | 360 |
| cggggtgagc | gtcgggccga | agctgcccgc | agcgagaaca | agaataaagg | atctgccctg | 420 |
| tcacgcgagg | ggtctgggcg | atggggtgag | tgccagtcat | ccctagggct | ttcatcctga | 480 |
| gggacaagga | cccacagcaa | gacgactttc | agggactatg | ccaaggcgt | gctgccctgt | 540 |
| gctggacgga | cggctagcta | gttcaggttg | gcgtcccaga | caattacttc | cagttttaa | 600 |
| aaggtctcac | cttgtagcct | aggctggctt | ccaactctca | cccctgtct | cggcatccca | 660 |
| ggtgccggga | ttgcaggtgt | gccaacacag | ctggcttctc | tttaggggaa | cctgacttct | 720 |
| gcatcctgtc | attttggtca | aggatgaggc | aagattcacg | cttacctagt | ttggttaccc | 780 |
| agtttgagtc | tgccaacctg | gtatcctagt | ctagcctggg | ttcattctcc | atcctggtac | 840 |
| tcaccaatgt | tgcaacatgt | gttacatcac | ttcccatccc | ccagctgatg | agggcgacac | 900 |
| cacctactca | gctcagttat | tagtgatatt | tcactctcca | gcccccagta | ctgttctacc | 960 |
| tcacaaggtg | gagcaggatt | tggctgggag | gaactggatg | gggtggtaag | tagggttttg | 1020 |
| caatcccccg | aaacagccac | tggatggaga | acatgcctgc | ctggaacagg | tgtgccccaa | 1080 |
| ctgtcctctt | ccccagcttt | tgtgtgccaa | cccagactgt | gaaaccccta | ggcacaaccc | 1140 |
| tgagtctgac | atacttagaa | gtggagtggg | agacccttgg | ggttttttc | gttttttagt | 1200 |
| tggtctctgt | gtaacaactc | ggtttgtcct | ggtactctat | agaccaggct | ggccttgaac | 1260 |
| tcacagagat | ccacctaagt | tgattttcct | cctggaaggg | tctgcccttta | aggtagaact | 1320 |
| gaggccttca | gggaatggag | gaggggggaca | tataatttaa | attacaccac | agcttttccc | 1380 |
| atacaaggca | aagcacccca | cattgcttag | ctgaagttgc | agaaactggg | tgaggaagaa | 1440 |
| catgctaccc | aagttttcct | tagaagggca | acggcggtgc | agaccttcaa | tcccagtgct | 1500 |
| tgggaggcag | aggcgggtgg | atctcttgag | tctgagtcta | gcctggtcta | cagaaggagt | 1560 |
| tccaggacat | gctaattatg | gtaatcttga | aagtataggc | aatcaggaag | gaaggaagat | 1620 |
| tgctggcaca | tcaactatct | agtggttaca | tccactagta | catgttatat | aaagtcaaga | 1680 |
| acatgatata | tatatatata | tatatatata | tatatatata | tatatatata | tatatataaa | 1740 |
| attctaaatt | ccgtcttctc | ttaatggtac | agcgtgagta | tttctcgcca | ttcgtacatc | 1800 |
| tgccactctc | ctatgctgga | gctccatccc | ggctttccca | cttggcattg | gcgctagtcc | 1860 |
| tgattggcac | tagtcctggc | tgactgctgc | tgtggttatc | tgcccctgga | gaggtcctca | 1920 |
| agcgtttcca | tcctaggggg | caagccttcg | gagctgcccc | gcacacagcc | tacagcttct | 1980 |
| gatggcctct | tttcccagtg | cttctctctt | cactgtgcct | tttgatgccc | taacagggaa | 2040 |
| ggatgtgact | tgctggtgtt | gatgctttta | agtactctca | gtcactgggt | aatgggacgg | 2100 |
| gtctgctgtc | tgctgtggct | cctcctggag | gttacttgtt | cttcctgggc | tcccctctgt | 2160 |

```
cttccaagat cagggcacct gttaaattca ttttttttgac agggttttgt gttttatttt    2220
ttttagctca ggagaatttg tcctccctca gctcttgagc agttcttcgt agcaagggga    2280
tttctccatg ttgttgttca gtgtagaaaa tacagtggaa gaaagtgggt gtggttacct    2340
catagactag ggactaatat gagaagcaaa ctagtcagtt tagctctctg ggatctgctt    2400
gggtgaagga ctaggtggag agggcagggt gctcaagcaa attttatgtt atcttgacat    2460
cttcaggagg cctccttcta cctccttggt ccgtgtagac actccctcgt ggcctagttt    2520
gcctccgcag atcagttccc actaaccacc ctgcttagtg gcagtgttca agtaaggaag    2580
gaagatcatg gattctctga agggaagctc tgtaatgggt gagagattgc actgacagct    2640
tggtaacttg gttttttgtt gaagtttgga tggtgtgcaa agtttgttgg aagagaggag    2700 tctttttta atgttttttt atttatgtgt gtgtggggag gggtggtttt tcaagacagg    2760 tgttttgtt ttgttttgtc ttgtttgttt tttcttgctg gctgtcctgt aactccctct    2820
ttagaccagg ttggccttag agaaccacct gcctgcctcc tgagtgccac gattaaaggc    2880
atgtgccgcc catcctggct tgccttggta ttttctgatc tccgaaagac tggcttagac    2940
tgtggcttag aggctggtaa gaggcagcag gtacatccct gcctttgctc ctggataggg    3000
aacttctcat ggtagagccc ttggatgctt gtggctattc ttagtttagt ccaggaccca    3060
gtatgaggta ggggcagtag agttctgagc tgggacattg tgtggcttcc aaagcctagg    3120 acagggtgg agtcatagtt gggattttaa tagaagaatc ccagcagctg tttgttgatg    3180
actgcatagc ttgatggtg gagatggaga tccctccc tgggtatacg ctaggtggag    3240
ggtaaaacta agtggccaga ttgttggggg ataattctgg aactgagagt tggcaggcat    3300
ctgacatagt cctgtagttc tgtgatcgag gaaagaaaac cccggttgcc cctactcctc    3360
ggttccgtgt ggcttttctc ttggttgagg tatatctgtt gccaaaggct cacctctgcc    3420
agaaaaggag ggcccagtac agtgctttct tagcagggaa gtgactcagt tgcaagtgtg    3480
gaaatcctgc tccacctcta ccctccttct cctgaatcca gcagcaagta cctgaattat    3540
cgaattacag ctaccatggt gctgggtctg gcccaacctt cagagcacag actaaaaact    3600
tgatttcccc aagaaggact ggtccaggag tagaaaagac atgctagaac cccgatccat    3660
ctctgtctgt gcctatcagc ctccttaaac ccgagatgta tggggacagg aacacatagg    3720
taccgcgcag ttgccagatg aatgctgatc caaactgcat gctgggtatg gtgtctcctc    3780
ccaagctttc tgaggaaact cccccaggct tggtggctag ggagatacca acaacccaca    3840
gaacttttgt ctggcttgat aaattgctcc cctctcccca atacttcaga cctcagctcc    3900 tgtgggttg cccaaacact tcccaccatc tcacgatgtc ctgtggtgag gacgctacgt    3960
gccacgtgct ggtggtcttt ctgaccctcc accattgtct gtagtagctc tctctcaggg    4020
tctctgccct tggttaccct tctcagatct tggcgtgcct gcccagatgg tcagagcatc    4080
ctccagctcc caaagcttgt gctttggtag tccttatcat tacctagtta tgacatgtgg    4140
gtattgttta ggtaattgtc agcccttgag gacagggaac tcgttggtct tcctcagtgc    4200
cgtgtctcta gtgtctgacc ctgtgcaggc aggtggtagg agcccctagag gtatttattg    4260 agtgagtgaa tcattagtgg gacttccagg tcctctaggc agaaagccct gcttttagct    4320
tcagtgtaat tcctcagctg tccccagagc tctttgcttg tgtgtgctga gtgtccttga    4380
gatactcagt ctggctaaga gcttgtcttg gggggttga gtgccaagtg ggtagaggca    4440
ggtgtactgt gatccacaca gagttccata ctgtacaagg ccaaagccag gattcctatc    4500
ccacctttat tcctgccccc tctgggacac gatgggtttg ctgtctctga agatttcatt    4560
```

```
ttcctgtttt gaaatagatt ccaagctggg tgtggtggtg cacaccttaa tcccagcact    4620
caggcagagg ctggtggatc tccgagttcc cagacagcca gggtgttggg aacctggtat    4680
cctaagtggc atactccctt ggccgcatca tcaaagacga ctaccttact ttgtaaaaac    4740
ggagtatgtg aagactctag ttcctggagc ggactctcct gggtatgagc ttgcagtctg    4800
gtggctgaac acttgtgtgt cagccagcct gcctgacttt gcctcagcaa gccacggtct    4860
cttgctgatt gtcagtccct tccaatggga gacggacaag ggtgtggtca aagtgtttcc    4920
actgttctgg tgctgagcct gtgagaccct gtgctaagc cacaggagca gaagcctgag     4980
ggtctgccct cagagcaact ggtaattctg tgccaggaca gggacctcgc tctgcttctg    5040
cttttccacat ggagccagct cctcggtgcg gtcagagagc cctgtggtt ccttccagac    5100
ctggccccct gctcttcctc atttgtgtcc tcccagaaaa tggggcttgc atcctcctta    5160
gggccctggt aagtacccta gagaaagtac ctccccgtgg attgtcataa ggacctattc    5220
tggggactcc ttggtgacgc acatgcaagc tggtggtgtt gccatagcag cccctcctac    5280
tccaggattg aatgtgctgg gtcagggagt tggggctgag aaaactggtt gctagggtct    5340
catgtcactc atggtggtcc tggttagctg atgagaacct ggcatcctac ctctcaggac    5400
tctcccttac ttaatgaaaa ctagatgtgt taggccctga ccctctgggg tagccctcgt    5460
gggagccagt gttcctatta gaaagatcgt ttgtagatta aaaatccatt aggaattcaa    5520
gcagagtaca ataggtccaa gttggcaaga cctcaggcct catctgctct gttcttatta    5580
tgtagtgctc gagggaaacc tagagagaag gagggtccca gaaaatcact gggatggtgg    5640
gctctctgta tcaggctctt gatggcctgg ctaggtacta cccaagtcca gcatggatcc    5700
gtgttgagtt ggcctttcct tagggccaga tgtctctatg gacactattt taggacttat    5760
cgtttctata atagctctca aaggagattg ctcatctctg tggggaagaa ctcaccagtg    5820
cgttagcagg taagtggcta gcttgtgccc tgtccacagt tgttggaaag agtggaactg    5880
gataggcttt ttctggtgtt catggtagag gtcagcattt catggccttc tagtccttcc    5940
tgcctgcctc tgtcacttcc aattcagtct ctggactaga cttttatccg taagtcctca    6000
ggtttgtcct ctctttgtag atgccagttg cagggcccat gacttcctca catcagtctg    6060
acacctcagc tgagctgtta caccctcccc aggatagtct ggtgacagac atccctctgt    6120
gcctggtcct ttcaagccct ctatctaatt catacccgt ctcctcagct gtgtctaggg     6180
tgggtagtcc aagagctaac acctctggca ggtgcctggg aagcagaagg gagtcagggc    6240
tgaaaggttc ctcttggctc aggatcctta ggaagtttct ctctggagcc ttgctgttgt    6300
ccctgacatt agcccactag cagaaaaacc ttccacatag aagaaaatct ttcctgtgtg    6360
gcacaggtcg actgacttct cacccaggcc cttttaaatt gattgcagtc ccttcaagca    6420
ttcaggcatc agccagggac ctgctcttgg tatggctccg ttctgggcat aggaacccag    6480
acagagtgag atgtagttct tgcaaatgaa cacacacctc atagtctaag gggctttgag    6540
tataggattg agaggcaacc tgtcagcatg ggcaggccac cccagttggg tacaggaaga    6600
cttcccaggg gagagtgaca aggccagttg gcaaagccag tgtctgatag ggatccccaa    6660
agtatgtgct gctaaacaac tgaccagggg gacgatgcct ggtggcactg caggctgggt    6720
taagagcctg tgaggcggtg gttggggaca gctctgtgca cagggattgg cagagcctgg    6780
cactatggta ggactgcagc aggcctgacc gtccagagct ggtagttccg ccatgatggc    6840
cctgtcatca tcacatgtgt ggactttggc cgagagtacc tccctgaggt cacccagaag    6900
acagccagct cagctctggc ctcaaagaag ttgcagcagt ttgtcacttg atggggcctc    6960
```

```
ctgacttccc agcccctcat aaccatgtgg cttgtgcaca gtccttggag caacttaaaa    7020
gtagtttccc ccctcctcaa accaaggtaa agtttcagtc caggtggccc agatgcagat    7080
gtggcatcct tcggacctga gaatgtggac agggtgcttt tctgctcagg ggcctaggg     7140 cccttgctgc ctctgatttc taggtctttc catctcttaa tagctgggcc ggttctgatt    7200
ggttcttacc acaagttatt tgggttcctt acagggaccc tgggttataa ctaaggacac    7260
tggatctcaa ggagggtggc aattcgcaaa gtgttaaatc ctgggtttgt attgctttaa    7320
ggagaggcag gtgttgttac atccataagg caatgaaagg ctattgatgc tcacagataa    7380
ttagctgccg ctcatgtaga tccttgccta aacatgatcc cacctaattc cctcagcagt    7440
cttcccgagg taggtattag ccccactgtc caggtgagga acccaggct tgtatagacg      7500 tgactcatcc aagccacact tcctgtaggt tagaggccag ttttcctcac ttgggttctg    7560
tggacttctc ctgggtgtag tttctccaca gatacttctg tggaggcgac agaggagcca    7620
tgggggctgc cctaggacat ggcctcccag ctgctgtgtg tggcacatgc ttctacacct    7680
atgctcccac ctcccctgct caggccaggg actctcaggc ctggctctgg ctctggctct    7740
ggctcgttat cccaaattct tcctttatag ctcgtctcca cctgatagca cattctctcc    7800
cttatcagtt cttgagcttc cagacaggtg gggctgatcc ccaccccac cagcactccc     7860 accccctggca gcgccttta accaaccgct catgaatttg ggtcctatgt gtcacactgc    7920
tttgactata cagtcctctg tttccaactt ctctctggga cattccgatt accacccccc    7980
acctttctgg gttgttgatg acgcaccttg accctgcctt attggaacac cccgtctttg    8040
ttttgcctgt tctaccagca accgtctctg ctcgccttcc tccaaagccc attctgtgcc    8100
gtttctccta atgcacagcc ttgtcccacc attagcacac tgagtgaaaa gccgtctgcc    8160
cagtctttat gtccttccca ctgggaggag aaggctgcaa ctgcctcgcc ttactggcca    8220
cacgcacaca ctcacacacg tgcacacaca cacacaagca tgcacacaag ttacaatccc    8280
tgtatggaag tcagagcaca gcttgaagga gctggtgctc tccaccatgt gtgtccaggg    8340
attgggactc cgctcatcag gtctggtagc agctgccatg tatttctca tttaatctttt   8400 cccaacaagc ccttgaggtt attctcaagg gttatgctca gggcgctgtc ttactcatct    8460
catgttacag ccccacaggg ttgcccttcc ccacattacg ctcttaggtg cattctgcca    8520
ctcttgggca aaggtgagag agagccaaga ggccccgggg agcagtctcc ttgctcaccg    8580
atattaggta ttgaacaaga agggtctaac acaggtcacg tcattcccat tcgtgggtcc    8640
cgagatcagg cagctctggt gacctcagca ggagcttggc tatgggaacc actgggtggg    8700
gttctccctt ctcgcacagc cagtctgcac agacctgtcc ccgtgacagt gaggcacagt    8760
gtaggcagag cgggcggccc ttctcatcca ggtgttaact cggcgtttgg gtgtagactt    8820
gccatgttta gtaggggaac ccgccctctg taccatggca ttgttcaagt gattgaaggg    8880
attggtgtcc aaatacctac tctgagtctg gctggcattc tgtgccttct ccgtgaggtc    8940
aatctcttcg agtttcatca tgctggttcc ctccttgtct tgtgccctcc taagaagtac    9000
tatgagatag tggcatggcg tagggtggta agacatctgc tctgggccta tctggcattc    9060
ccttccatct gtcctccaga catggagtag cacatgagct gtgtgcaggg atctgcctcc    9120
tgagtggcct gtgggaaccc tgacttcaca ggactagtct atttatacta tcaatgttta    9180
cacgtggagg ttcccttcgt aagtcaggga gcccgtgctt agagatggca ggagaggctc    9240 agcatttcg tagcagggtt tggattcttg aaagcaaccc agtgaaattg gcacccagc       9300 ttcctctgga gccagccatg ttggatttgt ccaaccatac agcaaatctt tatattgtgc    9360
```

```
ccctcccct cgccatatcc ctgtgtgatg ttctatacac acagatgagt caggtccagt    9420
cttggcactc acaagtcact gagagaggtg ggtgagcaag ggattctgtg agactggagc    9480
cgtgttaaga acacagaaga gtgggtgtgc ccagggaggc ttgggatgag gaagttggat    9540
ttggctggat gctaagactc tcttaccacc caacctccga gtcaagcagg cagggcgtgg    9600
aggtggtggc atttgattgt agcttcctca ccagctggac ttctgccaac caagctgag    9660 tagggaagt ataacaacca gatggcaaag actggttatg ccctgtggat gtacaaggga    9720
accttcactt cctggttccc caggtgattg tcccagggct gctgcaagct ggtgaacttg    9780
aaggcccaaa ttatgaccag gaggtggaca ccagggatca tgagcttgat ctaactcact    9840
ccagaaagga aaagtcccct gaccagcttg cattggtggc acagctggaa ccagatagag    9900
cctgaaggcc tttgcccctc gctgctcttt aagaagcctt ctgtagcatg ctggtcattc    9960
agcactcagg aagctgcagc ggaattgcaa gtttgaagcc atcctgagct atacaagact   10020
caacaaaacc aaagctaatc actgaaacac aaaatgcaaa caaaaagaac atgaaacggg   10080 ttctaatttta ccctcaggtt aatttccatc ccttcccagc attccccagc ttccctgtgg   10140
ggagaagaca gaagggactt gagaccagca gcactggggc aaatgcaagc ctgaatttgg   10200
gttcgaatag agtcccacac tcatgctggt tccctccttg tcttgtgccc cctaaggag   10260 tactatgaga cagtggcatg atcagcatca cattggggtg atgatggtag attcccagga   10320
ttccaaactt taggagctcc tcctcaggta ccattcttgc tgttctgccc taggatcctg   10380
aatggctaga gttgagtgcc tttctcttat actagccagg ccttgtcagg gcactgggaa   10440
cccagatgta gatcagaact gaccaggcct cgggcagtat tgctctcacg tgacaatcaa   10500
cttgaactat gtcctttgta caaggaagag agtacaggag ctgagaggga gaacttcctt   10560
ttcatcccct gctgctctct cctcactta ctgtcacaga caacctcccg gggggctaga    10620
aagcctctgt caggctccag gcttgggtgg tccccaggga agaaaagatt gtacctccct   10680
ggaggtacag tacagccctc tccatcggaa aagcatagtg tgtcaagcag gatgtcacct   10740
ctaaggggca gtcactgttt cctaggtccc ttagggcttc cactggagcc tggacttgag   10800
gcaggccagg cagggaggat tgtaggagtg catctgagga atgtagtgtt gcagtccacc   10860
cccaacctct ccagacatct gccatttcct ctcccagaaa tgcagcaggt cctccctgga   10920
ctacattccc gttttgctgg cagggcaggc agtaggtggt tggtccagtg aggcaggata   10980
agaacaggat gggctctggc ctgcatagat atggcctgcg cagagtctct caggcccttg   11040
gttttgtctg tataatggga tgagagctta acaaaatggg gtattcctct attttaagca   11100
gtttcaaaag attggaggga cttgggatgt tgtgtgtgtt ttttgttttg ttttgttttg   11160
cttttttcct tatttaggct tactcagttt tggatggggc atataaccag taaggagttt   11220
ctacatgcct cccccaagct gagtgctgta ccagctacag ttggctgtgt tgactaaaat   11280
gcaaggcctg ctggcctagg gtgagggttt caggcctggg cttgggcctc actttccagc   11340
aggctcaagg tgtcttccta tgccccgtgt gcctttcctt aaacattcct ccaaactcta   11400
gcctgaggtt tttcctgctg tagtggtggg gctgataaca gaaggcattt gccatgcatt   11460
catttcctga caagcagaag gctgaaccct ggttcactca cttactccat gggagactaa   11520
atagttctag ttgttgttcc tcaaatttag cacctggggg tattgtcaac tgcagaatcg   11580
actcattgga ccctgtcatt tctaacctgc tcacaggtga catgatgtgt cctagaccat   11640
gcttaggaca agacattgct acagaacctt ttgtcttcct gccagtaggg tacctggcct   11700
gcccgatggt tacctatgct taaccctcac ctccattgtt gctgacagtg atgtagccaa   11760
```

```
ccagccttac gtcaggagtt tagactgcat cttggaggtt cattcctctt atacatatgt   11820
gtgagacttg tccccacata cagtccaggg aaggtcatga gacctttaga tataattgtg   11880
accaagtcat ttatctaggc tcaactggtg ggcagatgta ccaggccctg agtttggtcc   11940
acccttgaac ttgatatgtc caatggtcag agtcctttgc attcattggg tgctgtattg   12000
aacccaatat aaagtataga gaataatgtg ccctgaacag aggcaggaat cctgggttgt   12060
tctgcctggt aactctgctc atgctaaaat gtgtgatccc tttagggctc aggatgaaac   12120
ctaaagagca gtctggttg ggggaagggc cataagaga aagggccta cgacagaaga     12180 tttacaaaag aggtgaaggg gcaatgcacc agtctctgaa atggctgtgg gatccaactc   12240 tgttttttgtg cctttgcccc accattcctg ttgtatatta ttgagtactc agtgtgtgac   12300
ggtcattggc attgaatcct atactctccc ctggggtcac acatatagag tgagacggag   12360
agtttgcctc tacagtgcca cgccctcttc atctggttta ttagatcagg aggtgaaagg   12420 actgaatgt ctggcatttc ctacttacgt ctgaaaatca gagaggctgt gagctttcag    12480
ctgagaggag ttatacttct ttctgaactt ggctgtgacc tttctgctat caattttgac   12540
agagagcaaa gactcaaatg tgaacccttc gatcccttct ttcctggttc ccagcttgtg   12600
ggccagggcg gatggtcagg agacattcaa ggtcaagact gacaggcatc tgtcctgggc   12660
cctgggcagt gggcagtagg aaaggagtgt ttgggtggca cacagtaggc actcaaaata   12720
ggctgacaaa gggacacagc tgggctcaac atttagtgtg tgaagtggcc tcttttttagt 12780 ctaagactgg aatgagtggt cttgggacct cacccatact cttctctagt gccacctctc   12840
ctgtaggcac caggcttcct ggccacacta cctgtcagct gctggagccc agggtcatc    12900 ctaggtctcc aactacagag ccagtgaatt gagcacattt tgtcctgatt tccagtcttg   12960
gcacttgctt agaagcaaac ataggtacag ccctagctca ggtgcttccc cgtgtcctgt   13020
gtgtctttgc ttattaaaca ccactccaaa caccagcttg ggtttatct gcagtgtttg    13080 ggagcatagc ttccccaaca agataccccc tggatcctcc ctgagcccca gctttgggg   13140 actacagtga gacgcatgt aaatccctct tgagttgctg gcggtatagg attggttgtt    13200
gggatgggaa tgagagccaa cttaatggaa agaagggtgc ccagaataaa gggagtgggg   13260
cagtgatcca ggatgctcaa agtacacttg gacaaaaatc aaaacaaaat attgcaaatt   13320
ggatgttgaa cttctgtcct tgacctcata gccacagata tcaaagatta aatatttgta   13380
ctaggcccag ataaaggaag atatgtgttt gggggcatagg agatagaaga gatctggcct  13440
cctatatata tggcccaagt ccagggcaag ctcttagatt ccccagtacc atatcccctt   13500
gtttcctatg tagaaactat gattcaggga aggcagtaaa acagctatta ggaagacatt   13560
tggtggctga gtggggttca gttatttttg attctgtggc ccacattcac ttatctagca   13620
aggcatctgt gggatgtgtg ttatgttgag gtgtctgatg ctggagaaca ggctcttttt   13680
tttgttggat atttttttatt tacattttcaa atgttatccc ctttccctca cccaaccacc  13740
catcccttcc cgcctccctg ccctgacatt ccctacact gggaggtcca gccttgggca   13800
ggaccaaggg tttctcctcc ctttggtgcc caacaaggcc atcctctgct acataggctg   13860
ctggaaccat gggtctgtcc atgtgtactc tttggatggt ggtttagtct ctctgagctc   13920
tggttggttg gtattgttct tatagggttg caaacaccttc cagctccttc aatctttct    13980 ctaactcctc caatggggac ccagttctca gttcaatggt tggcttcgag catccacctc   14040
tgtatttgtc atgctctggc agagcctctc aggagacagc tatatcaggc tcctgtcagc   14100
atgcacttct tggcatcagc aatattgtgt ggatctggta gctgtatgta tatgggctgg   14160
```

```
attcccaggt ggggcaggct ctgaatggcc attccttcag tctctgctcc aaactttgtc   14220
tccatatctc ctgtgaatat tttgttctta cttctaagaa ggattggagc atccacactt   14280
tgatcgtcct tcttcttgag cttcatgtga tctgtggatt gtatcttggg taatccaagc   14340
ttttgggcta atataagaga tagaagagag aatctcaggg gcagaagata tcatagaaaa   14400
catcaaccca accattaaag aaaagtgtaa acgcaaaaa tctcctaacc caaaacatcc   14460
aggaatgaga agaccaaacc taaggataat agttttagaa gaaaacaaag attcccaact   14520
taaagggcca gtaaatatct tcaataaaat tatagaagaa aactccccta aacctaaaga   14580
aagagataca ggaagcctac cgaactccaa ataaattgga ccagaaaaga aattcctcct   14640
gtcacataat agtcaaaata ccaaataccc aaagcaaaga aagaatatta aaagcaataa   14700
gggaaaaagg tcaagtaaca catagaggca gacctatcag aatcacacca gacttctcac   14760
ctgagactat gaaagcctgg atagatgtca tacagatcct aagagaatac gaatgccagc   14820
ccaggctatt atatccagca aaactctcca ttaacataga tgagagcggg tttataacaa   14880
acgaacatcc tctcctgcag gcactggctc cagcatcctc tcggccctcc aagacatctt   14940
ctctgtcacc tggctcaaca gatccaaggt ggaaaaacac ctacaggtca tctcagtcct   15000
acagtgggtc ctatccttcc tggtgctagg taagctcacc tagggtggtg ctgagtgggg   15060
cggacatggt tgcattcagt gaggttatct tcttccccag cctcttgcca cttactccca   15120
tgttttaggt caaacactcc accattaggt atgcaggaaa acataatcca tagatatagt   15180
atggctttat tttgcagctt aacttgccca acttcctgga ctctggttct gtgggatgcc   15240
tgaagcatgt gcccctctta cagtcagtcc caccttgtct gtcggcaaag agcaggtgtg   15300
ttgctttgcc ttagagcatg catcgccaag tttgagaccc actccagaca agctctgact   15360
ttacgtaggc ttcttgacct ctcagaacaa gtaccctcct cttgaatgtg aaggtgctgc   15420
tgctcacctc acatgccttt tgtaggcatc ccggggatta agatgaagg ttgaaagccc   15480 ctacacagag cctgctggtg gtcccattgc atggatgctg tggttagagt gttctaggat   15540
tccaatgcca ggcctaatcc cctttgctga gtctatcccc agccactccc ctgcctgtgc   15600
tggctttgtg acactgcctg tgcagactgg ctaggtgctt caatgtttgc cagctaggaa   15660
cacccgggac cttctcatgc ccaggcctta tgtcctcagc acaggctagc gtctgataga   15720
cctgctgcag agcaccacgt gtctggctct gtgtgccagg ccttcaggct ctctcttcaa   15780
actgcccagt atgatgggag cttggcagac atccagacaa tagagaacag ctgtccttga   15840
ggcaggcata gagcctcagc cctcggtgta gaccaaaggg aacaaatccc acatgtgcca   15900
ggttcttgga atgtctttg tcaagttccc actgcacagg tgggagttgg agtttgagcc   15960
aaagcccagt gcattccctt actactccat tcagaattaa tggagaggct gtggtgattc   16020
attgattaca tttaattaaa attaaatgta agaccatgta tgcactttta ttgctaggaa   16080
ggctggagct atcctcagat tcttgcaggg tcacatggtc ccagaaaggt gaagaagcag   16140
aggtttgagg acagggccca gcccctgagt gtggttttgca tttggcctct tgttagaata   16200
ccagagtaga ggagataatg caatctcatc tttgttcaga caggaaggaa ggacctagtg   16260
gggacagagc cttgtctaga gctacagaaa aaaatggaag gaaccaagac aagacttgag   16320
tgaccccagc ctctcggtcc tctcctagtc tgttttggca gctcctgatg tctctgtttg   16380
cactagaagc caccacttgc cttagtgggt cagaacttgg ctgtggggca ctgagtaaat   16440
tgtgcaatcc tagcccagag agcatgtgat aggaactagg gactggcccc gagctgtagg   16500
ttaatgatct gtgaggccca gccacagccc agaaactggc ctggcgtgtc tttccaatat   16560
```

```
gctagttggt gtaggtgaga gctagacctg ggcaagatga tcaggcctgc ttaagctgct    16620
gttaattact acatgagcag tcacagccac tccctctgtg tcccaaacct gccggcagag    16680
gcttgctata ctgtgaagct gcaatggagc ccctttatgt ttttcttaaa cagtctttgg    16740
ttttgttttt ataatgtgcc atctagtcca ctagaattct ggtgaaagct gtgggccttc    16800
ttggttcttt taattgtata aataaagtac attgggtttt aaaggagcta atattgccgg    16860
aatgtaacta tgtaaacatt tgaaacccag ctggacattc agtaatgtgt gctcttttat    16920
tatgtcgagt gagaaagtgg cggcagctat aataattact aatcttaagt agtaataaat    16980
ggagtatcaa gattgctgag gctgtcataa ttcagtatga acacacccctt gtcatctgta   17040 ggtatcgtgt caacaggctt tgctaatact tctgtgactt agtgaaggaa atgctgaatt    17100
tccatgtgaa tccagaagga aatctggatg tcattttgc tcccccatac aggcccataa     17160
gcacttactg tattccagat cgtgtgttac atcccaacat catgtcattt catcttgcca    17220
gccctctata agaaaggaaa ggcccggggg tggccaagtc tctgactatg cttggtccta    17280
gagtccctct ctccacagcc ctgttgctgt gtgtccttcc aaagggcacc cacacactgc    17340
cctgtacacc agcgggggtc agagctctgc tgtgtgagtt gtgtgaggct gccatgtaca    17400
gggaggcatg tacgcaggta gttctgagca gtctctgtgg aacagcagga tgcttcagtc    17460
actgtgctaa caggtcctgg gcccagtggc attgagggc ttcagcctga ggacatggca     17520
caggcagctg ttgtaggttc tccaaaaggg agaccatttt atgggctagt tcattgttgt    17580
cttcccaagc ctcctctgtg aggttttttgg atacaggatc tcattgtgta gccctaattg   17640
gcatatctgt cagtctgtct gtctgtctgt atccacattc ctctgcctcc agagactcta    17700
aagttttcag cctccatccc agcaggtggc tcattctttt tacttaaagc cctttctgtg    17760
ttggtggctg ggctggagag attaatctca ccttgttcta gctccagagt ttctcatgga    17820
cttagctctg ttagacaggc aggtggtgag agaaaatgta catcttgagg ggcggggggg    17880 gggggggcagc tgcgtagcgc cagggctgga attaccaacc ttgggctttt ctcgcttagt   17940
catgcagaaa ggacaggtat gaagtgataa ccttcctccc catggcaacc agcctccgg     18000 cagcaagggc tgtaggatgt tttcactaca cccttctga actctgagtc ctggcccct     18060 tggactgaac tgagccttcc tctctttgct ttggacactg cagaggctgg cgccggagga    18120
acctttttct gggaccaagg aaggggggcac gaggcaaatt gttggaacgg tgtcgtatgt   18180
gcagcctaaa tataagcagg attcttctca gctgccttag gacctacatt atcctcaaca    18240
gggtgtgtgg gctgcagacg cctcccacga ctcagcgtcc tatgtgcgtg ccactgctaa    18300
actgtcctaa gaaaccacat gcctgttctc cagaaactgt cgtctggttt tagttctcct    18360
gggctcagga gagagggtga gagccacaat ttccctgttc tgagggtcac agagatctgc    18420
actcagacct gttctttgca atggaaacaa ctcaggctta acagtgtaga cggaaagggt    18480
catgaaacct gagttccgcc cccatccagt gcccctttttg aggcaagaga ttgtaggtgg   18540
ggtagtttga tatggaggag cactctgcag gaacaaggat ctgactgggg cttaaagact    18600
gggtaaaaag aagccatgat gaagggatct aggggtggcc atgagatact ggctctcctt    18660
cctctgggcc aggccattca gctgcatggc ctgccaggag gtccaaagta gatgttccag    18720
gagactctta agtgtttggg gacagggagc ctggtgggct ttggctctgt cccggggctg    18780
cctagcctcc tgtatgttaa aggggacagc tctcctgtga caacagtccc cttcactcct    18840
gactctaccc ctcaccatcc accccccatca caatctgaga gttgtcatct ttggtgaact   18900
tctaaggccg agtatggacc ttggacttca aagtctgagt ttaaaccctg gctctcctct    18960
```

```
gggtaagcat gggcaagtca ctcttgccaa gttctcctct aaaacaaaat aaaagtcacc   19020
cagctttagt gactcagtgg cttagcccat ctccaaaagg aaagggagat acttgatatt   19080
cctttcctgt gtccagtgtc tttgctggca aaggggccgt tcaaggagca gacatgaagg   19140
attgcttcac gagaaactga ggtctccctg tactgctcgt cctgctcaag ccaggtgccc   19200
ctggcactag gactcaccag aatcttaaga agtgaggcct gtgctggctc tgcactgagc   19260
cagccaccca cccactactc ccagtgccta ggcatccggg ccctctgcct agattagcac   19320
catgggaaac ttcatcccct tcaaggggga agccttggcc cagccaggag gcccgggaac   19380
ctgacctgtt gtcctctgcc cctcaggagt ggcctgcagt gtcatcctca tgtacacctt   19440
ctgcactgac tgctggctga tagctgctct ctacttcacc tggctggcat ttgactggaa   19500
cacgcccaag aaaggtgagc gtccgcgtct cccacctgtg ttcaccccgc gccctagaaa   19560
gctttctgcg cagctgccgc cccgcctcct ggctgctgcg tccttttttg gaacacctac   19620
tttgtgaagg acctgggcta ggctgtgtat ggcttggggt ggcgattca aagctccttt    19680 ggtgtgttca cagagctcac cttcttaag ggatggtggg agggaatgta tgtgggaagg    19740
ggcccactgg gcagggacag tgatcctatg tgggctggta gacacataca tccctcaggg   19800
ttcttactgt ctctgtctcg cctcgcctgc attgctcaaa tgccctcgc gcccactcct    19860 tcccaacact gtgctttgtt tcctggaagg tggcaggaga tcacagtggg tgcgaaactg   19920
ggccgtgtgg cgctattttc gagactactt tcccatccag gtaaagacgt ggtgtgctgt   19980
gttgggagga tgtagacggt gtgctgggct gaactgtctg gggttcccac catgagcgtc   20040
ggtccagact ctactgactc catgccagac aggagtttgt tggatctgtg tactgggaag   20100
tgaaatcaag gtctttgaga cagagcacta ctattttcag ccataaagag gcagagttgc   20160
cgcagttgga ctaggcagcc aaggcgatgg gagaaagcat ggtattcact ggcttctcgt   20220
ttgattcttt ggggaaagca agacttgttt ggttctaaaa gataattctg cactgagggt   20280
ctgtacgatg taaggggcag gcaggcaggc aggcaggcgg gcatcgctgt gctttgtggc   20340
cttgcttctc ctacttaaga ttgaggttat aacttaaaat gtggtgaccc aagaggtgaa   20400
gcacttagag ggtgggcta gactgttaag gcggtgtggc actgagaggg cagggagaga    20460
gcttaagcct gagtgtgaga aacagctgtg tgaggtgtga ggagaaaggg agcctctgtc   20520
cttctccaca ctgctccctc cactaccctt tggaccaaag aggaacctgg aggttagaga   20580
agaacagttt ggtgaagcca gtgaacagct gaatggtttc ctgttgctgc cctgcctcag   20640
cgcccgggtt cctcccactg gggcgcagtg cctctctact cagagcagag tccagtggag   20700
tccaggtgct cacgctggga gatggaggcc agtatcatcc agggtgggac tctgtcttcc   20760
aggacacagc ctcctgccat gtccctgtg ggtttcttcc tagtgtgcct ttggctattt     20820
gagggctctt tgcttgggag gggggcattt gtgtccccca ccccaccagg aacaatgttg   20880
gtttcttgtt ggctccaact ggccctgcct tgtatgcagg cttacagagg attgtgagtg   20940
gtgtaggttt cccacagtg ggaacctgtc tggccagcac tctgagcacc gagccctgac    21000
acacccttgc tgctaaggcc acccagcaga aggcagagaa ctgaaaacag aggcagtaag   21060
tgagtgtgaa agtgttctgt gcctgacagg gggtggtgtg cctttgttgt tgtgagtcag   21120
gcattgagat gtccagatga gctgcccag gaggtagaag tggccctgca ttcctcccct    21180
gcactgctct tgggacttga ccccagccat ctctacaact tggaagattt cctcttccca   21240
aatcttgact agaaccaggg tttaagtttt tttttttccc ccggagctgg ggaccgaacc   21300
cagggccttg cggatgctag gcaagcactc taccactgag ctaaatcccc aaccccagg    21360
```

```
gtttaagttc ttgctctgcc atccattcac cgacctgccg gtgttggggc tgtcaggtgc   21420
tgctcttggc catggtgatg gaggagagag agccctgggc tttcggtcta gtgaatccta   21480
tcacggtttt actcagtgtt agctttctca gccttcccaa atgccatttg tctcaactgc   21540
aagttggagc tgttaagtga aggcaagtga gttaatgcta gggagacgct acgaggtctg   21600
ctctgctgtc ttcccagcca ggctggtagt cccctacctg cagcaagtga ccagagcatt   21660
caattgttct actccaacgg atcctctacc acctcaaaag acccaaatga caggctggag   21720
agatggctca gtagttaaca gggctggctg ctcttccaga taacctgggt tcgaatccca   21780
gcacctacat ggcagctcat agctgtccat gactccagtt ccagaggatc cagtaccttc   21840
ttctggcctt tgagagccct gcatgtacat ggtacataga catacatgca agtaaaacca   21900
ccagacacgt gagtaaaaat aaatctcgtg ggcatggta gcacatgcct taggcagaca    21960
cagctggatt ttcaacctgg tctgcataga aaagttctag gctagccaaa gctatggagt   22020
gagaccctct tgtctcaaat aaataaatga gtaaatctta aaaagagcca gtgagccaac   22080
attttcacta tttgtgtccc actgagctca tggggcatct gttgagctgc cctgtgaggg   22140
tatctgggcc tcacccggag cgtgacgggc tctacccttt gtcctttgct gctttacgtc   22200
gggtctgagg ctctgcgccc tagagctgtg tgtgacttgc ctgttctgcc tcttttttcct  22260 gagctcctgc cacgagctct ataacagaga tctccagcta gacccaagtg tcacttgctc   22320
cattcctctt tggagctccc cctccaaagt caccgagctg gcccagggca tctcttgtgg   22380
cagtgggagg gttggctctt tctgcagcca ctgggactat aaccacctgt aacagaagtg   22440
tcccatgtcc tgggattctg ctccctttgg aaactaggaa aggctctctg ggcttcagat   22500
cagctctcta attgcctgat ttcatagatt gcagaccaag gttcagagag gagagactgt   22560
gtcacaagac gctgctgacg tgccctgctg taagcctggg caagctgctg ctgttctctc   22620
tctgggactg agagcctttc tctgaatggg gctagggtat aagcctgtcc tgggagcagg   22680
gtgtggggag tgatctgcca aggatgtgcc caggcttcta ctcaccacct ggcctgtcgt   22740
gagcaccact gggctgggac tttgctaccc agtaggcatg tcaacagcag tcagcagcag   22800
tgaccttcgc cctccctaca tcctgtccag tcttgggaag gatagtgtga caggaatcag   22860
atcaggacta tatccaaagt ctctattctt tttggtactg catgggggcc attaaccagt   22920
acagtgaccc aaagatgtta agaaccttgt gtcctatcag ataagagcct tggggaggga   22980
cgggattgtt taaagggcca gcttggttcc tgagagtagc ccatcactac cacagggtcg   23040
tgtgtgtgtg tgtgtgtgtg tgtgtgtgtg tgtgtgtgtg tgtttcattg taacttccct   23100
aggggaggta gtgactcctt tctctagact tgtttagttt gtcatcaaga aatagcctag   23160
atcatcaggg tactgtaacc cttcctgtgc tttgtctcac agtctagcca ctggctccag   23220
agacagtacc agctcccccc tcagtgcctg ccttgcagta gacactggcc acagtgcttc   23280
agtaagagct ggctggggag tggacctgcc tgctgtctca agcagagcac agagcagcag   23340
cctgtacata cagtgggtgt gcccagctcc gtggggattc ccttgctgtc caccccatcc   23400
ctggcggcgc ccactcccat tccctggtta tttggtggcc agctgagagt tgtttgctgg   23460
acagtattaa cctgcttgcc aaagggaaat gagagtcacc aacagggatg acatggaggg   23520
aggcctgctc acatttacac atgcttccac cccagagctg agagcagcag ctgacccgc   23580 tcagtcccca cctcccagc tgagcagaag ggctaggagg gtcctgggac tgaagcagag    23640
gaaagttggg tgatgaacat ccgtccacag ccagggactg tgctagccag tgcaggaagg   23700
gatgctgtca ggcacttaga tggggatggt gtgagtgccc ctccctgggg cagggcagcc   23760
```

```
tctccagatc aggaattgta cttctggaag tttatctgga tctggaaata tagataaaag     23820
ggggctattt atcaaagcat tattctagga ggggaagttt ggatacattt taaatatcta     23880
ccagtcagga tttgagtact gtcgttacag catggctgtg aggcagggaa gtgcccttg      23940 gaggacacca atactgaggg gactgtgata agctcctcag agaggatatg tttcctagaa     24000
gacagtactg atgctgcggc tgtgtggtgt gtgggatggg gggaatggta tcaccaccac     24060
tgtcatcacc accaccatca tcagtgccag tctctcactg tgtagccctg aattgcctgg     24120
cacttactat gtagacaagc ctggaatttt gtggttttg aagaaagacc tgtgcctatt      24180
taagtaggaa aatgatcaag tggtttattt caatggaagt aatagtgcag atgttcattt    24240
tcttcttact ttcctataaa aaaattctga atattgggcc ataatgggag tgcagtttga     24300
ggcaagccta caaacttaca taggtctaca aagtgagccc aggatagcca gggctctgta    24360
acacgaagaa acctgtctcg ggggggggg tctattttct aatctaagag agtgatgttt     24420
taggaacaga gagcctttcc tcctcctccc ctcagcagct ccatatgcac tttacccctag   24480 tgagctgtct cagtctcagg cttgggggcc ccctgtggct tggggtttcc cagggactca    24540
acctcaggct ccttaggaag ccagttatcc ctcagaacat ctcaggacaa cttgttgata    24600
gaacaggagt tcagaccatt agctgccaca gccacacagc cagccacctc ccccgcctcc    24660
cacagatagg gctgcctggc acgagggcga tgttgtcctg tcctatcctg cctcagaacc    24720
taagttgagc ctggatgttc ggcaaaagct ttgctctagc aggcagtact gtccttttgt     24780
cacactggag tatgaagagg tgggtggagg gctgcatgct ttgtcctttg atctgttaaa     24840
gatcctgcag tgtgcaggga ccaggcagac cctgctctga ggaatactta gtgggagacc    24900
tgaagccgtg gttctacttg ccaaacttgg gatctagact gtacccagtg aaggctagat     24960
gctccagtga tgtctgagtg tcccggcttg gttatgagtt tgggaagtca ctgtgctgag    25020
gagcccagaa gcaggaaggc aggaggctgg tggaattagt ggctttgggc tgtggttggc    25080
tgggctataa ggagaaggaa gggaaaagca gccacccggg gactctgagc ccagtagctg    25140
ccaaccactg gcactggacg tccaataaga agaactgagg acaggtttgg aaagtctctg    25200
ctgtcctact tgcctagtga caaggcacga gatgtaggtc ccttcccctt tctgggtctg    25260
ccctgtactc ctcgcccaga tgggcctaac acaggatttc cttttagctg gtgaagacac    25320
acaacctgct gaccaccagg aactatatct ttggatacca tccccatggc atcatgggcc    25380
tgggtgcctt ctgtaacttc agcacggagg ccaccgaagt tagcaagaag ttccctggca    25440
taggccctta tttggccaca ttggctggca acttccggat gcctgtgctt cgggagtacc    25500
tgatgtctgg aggtaaggat ccacttcagc tactcctcct tggctccact gtcaaagctt    25560
gagcctccct gttgatccgc aggaagttct gttccctggg cccatacagg aagacagcct    25620
gcagcagata ctctagggc atcatgggtg acatcctctc acccacttcc tagatggacc     25680
agccgttgtg ctgcctcatc tgtgcccctg ccgtggtccc caccggtgga cttcagagct    25740
agggcttctt agatcttgct taattgtttt ctcaaaacta ctctgtatct ccttccccca    25800
ttttacagat cagtaaactg agaatcagaa aaagtgagtt gcttaggtag gaaggaagga    25860
ccataatctt ctgagaggga aacaggtctg ggacctagct atagagattt ttatttcatc    25920
cctgattgta tattaggaca gggcatgcat ccatgagcaa tcctgattgt gtgtcccctc     25980
gccccaggca tctgccctgt caacagagac accatagact acttgctttc caagaatggg    26040
agtggtaatg ccattgtcat cgtggtggga ggtgcagctg aatccctgag ctccatgcct     26100
ggcaagaacg cagtcaccct gcggaaccgc aaaggctttg taaagctggc cctgcgccat    26160
```

```
gggtaagtgc ctacacacac agcggcagga tttcttctaa ccaggacaat gggtcccaga   26220
ccctaggaag gcaaagaagt gtccacactg catggcttga ccaggtgttg cgcaaaggtg   26280
tgtgtgtgtg tgtgtgtgtg tgtgtgtgtg tgtgtgtgtg tgtgggtgaa atgtgtgtat   26340
atgtgtatgt gtgtgtgtat atatatgggg gcggcggggg ggatgtacac acgtacgcac   26400
agggtggggg ggagacttct gaatcctttc agatggtaat ctgaggcttt ggaatggaag   26460
agaatgctgg gtggctcagg gtggacttcc ctctgccttc cctccctcca gacttcacat   26520
gtaaaagtcg tacatagatt tttcacccct acaagtctct ccccactttc tgctttcctc   26580
ttttccagct ttctccgggt ctcggggcac acgactctcc tccactccat gcccccttct   26640
ccccaatcct gtcatatttc tagagggggcc ctggtaataa atatatcaga gaagagagaa   26700
accatgtgtt ttgaggtaaa actttaacag aagaaagaat gctgtttatc tttggtcttt   26760
gagaaggccc aggagcgtcc aggaagaccc tccttgaaag tttccaccca ctgtcttta   26820
ttaaaccctg gtcttcccag gatgtcaaag cccaaaggtg aactttaaaa atcctgtgta   26880
gaaacttta actctttaa ttaattacgt ttctgctcaa aggtatattt ccagcagtt   26940
tctgatagaa atgcattgtg ttctaagtgg taagcctttg tccccttgtc tcannnnnnn   27000
nnnnnnnnnn nnnnnnnnnn nnnnnnnnnn nnnnnnnnnn nnnnnnnnnn nnnnnnnnnn   27060
nnnnnnnnnn nnnnnnnnnn nnnnnnnnnn nnnnnnnnnn nnnnnnnnnn nnnnnnnnnn   27120
nnnnnnnnnn nnnnnnnnnn nnnnnnnnnn nnnnnnnnnn nnnnnnnnnn nnnnnnnnnn   27180
nnnnnnnnnn nnnnnnnnnn nnnnnnnnnn nnnnnnnnnn nnnnnnnnnn nnnnnnnnnn   27240
nnnnnnnnnn nnnnnnnnnn nnnnnnnnnn nnnnnnnnnn nnnnnnnnnn nnnnnnnnnn   27300
nnnnnnnnnn nnnnnnnnnn nnnnnnnnnn nnnnnnnnnn nnnnnnnnnn nnnnnnnnnn   27360
nnnnnnnnnn nnnnnnnnnn nnnnnnnnnn nnnnnnnnnn nnnnnnnnnn nnnnnnnnnn   27420
nnnnnnnnnn nnnnnnnnnn nnnnnnnnnn nnnnnnnnnn nnnnnnnnnn nnnnnnnnnn   27480
nnnnnnnnnn nnnnnnnnnn nnnnnnnnnn nnnnnnnnnn nnnnnnnnnn nnnnnnnnnn   27540
nnnnnnnnnn nnnnnnnnnn nnnnnnnnnn nnnnnnnnnn nnnnnnnnnn nnnnnnnnnn   27600
nnnnnnnnnn nnnnnnnnnn nnnnnnnnnn nnnnnnnnnn nnnnnnnnnn nnnnnnnnnn   27660
nnnnnnnnnn nnnnnnnnnn nnnnnnnnnn nnnnnnnnnn nnnnnnnnnn nnnncttgta   27720
ctctgtcatt gctttccgct cacatcccaa ctgtgggagc cttgactagg gtgagaggac   27780
tcactgcact gacccagtag gccccatgaa tcttagaatg agctcctctc gggttttagg   27840
agaggctgtt tgatggtgtg ctctattaga ccaaactaat gacagggagc gacagggaca   27900
gctagtgtgc tgaggccata acatgaggtg aatctggggc tgtaagggag ttgagttggg   27960
ctggacagca gacatcctgt tggatgaggt cttctaggtc cccagtgatg gagtctgact   28020
aatctgggcc tccctcttac agagctgatc tggttcccac ctattccttt ggagagaatg   28080
aggtatacaa gcaggtgatc tttgaggagg gctcctgggg ccgatgggtc cagaagaagt   28140
tccagaagta tattggtttc gcccctgca tcttccatgg ccgaggtctc ttctcctctg   28200
acacctgggg gctggtgccc tactccaagc ccatcaccac cgttggtgag tcctaacctg   28260
cacgctgaag gccatcctga gcatggcaag atcctgggca agtcacctgg cttacataac   28320
aaccttgtca caggggcctg agcagttggg tcctgggggt gaggaagttg agccagggct   28380
gcaacctatt aggaaagggt attgattcca gcactggcca tgcagctgta aggaggaggc   28440
tgtcgggtta tgctgctgtt ctactcgaca gcatgcccac ccaggagaca gcctgccctg   28500
ctgcctggga actcaaagcg gaaatgaggg aggaagagcc gtacagttgt acaagcctgg   28560
```

```
aatcccagta gggagggcag aaacagaatt gctgcaagtt tggggccagt ctgatctaca   28620
tagcaagttc caggctagct ggggctacat aatgaaaccc tggctcaaaa taaaataaaa   28680
actgcctaac gagagttcta aaaaaaaggt attgattctt tgaggaacag aaagaaaagt   28740
aagcgaacat agacctaagg ggaagaccag ccgtgtatgt ttgtcttttg ggacaagtca   28800
gagcattcag aaaatcaacg atcagggctg tgggtgtgta tgcgtgcatg tgggcgtgtg   28860
tttaaggtca cagacctgag atctcatggg tacatagggc cctgaagagt ggactggaat   28920
gtccaaaggt caggcagtac ctgtgtgttg agggtaggcg tttgcctgtc ctcggtgcag   28980
ggcagcactc ctcacatggg tggctgaggg acctgggctt gagccagtgc agcctcttca   29040
actgcaggtt gtgggcagtt gggaggagct caagcacaat tgatttattc tagtgatgcc   29100
tgtgtgcacg ggatttcaga gctaagctcc tagtgttgga ctaccaaagg ggatttattc   29160
ctgggagaag acttaattct tcctctcagc catcattagt tgtgtgtggt tcttagtcta   29220
ggagtaccac ccccaagagt tccccttctg tgctagtgtt tctctgtctg gccattgttc   29280
aagcctggtt tcaggtacca tgttgttgaa atatggtcta gcttccctgt catttctagg   29340
agaccaaatc tcttatcaga cttctgctc ccctggttct cacaatcttt ctgtctcctc   29400
ctctgagatg ctccccagct ttgggtgtgg ggttggattg tagacctgtc agttagggct   29460
gagcacccca ggatgagatt ttgaccagtt gtggctttct gtaatcatct ctgcctgctg   29520
tgaagagaag ctactttgag gactgggtga gagccattcg tatctacaac tttaagtgat   29580
ccctggtgct gttaggtcga ggggaaaaca aaggttagca tgggccaaaa gcagaagcca   29640
ggcagccagc ctagggtttt cagtagcctg cactgaaggg gtggtggtgg ggagggtatg   29700
tatgcatctg ggagaagtct cagaacagtg ctgctgggcg gggttgccgg gcttgaacaa   29760
gaaacaggat gagacaaatt aagcatggtg tgaggaccgt cctcctctct ggccctcaca   29820
gctgctcaag catggtcttt cttcccagaa gccttagaag gaaagctcta tgatacagat   29880
gctgggtggg caggtggcag atgggtaaac tgaggctcta aagtagtggg gtttgtcctg   29940
agtgaagcaa aagcaaagtt tttggtccac agcttactcc ggaactccca gcagagtgtg   30000
gagcagggct tcaccagtac tcagaggcca cactcttgtg tggggtcttt cccacactgc   30060
taggctgtag tctcatctgg gcaaaaggac aggccatgat ggtcagcaca cagcatgggg   30120
tcatatcaca ttgggcaccc aagaatgggc tactccgtga cattgactga cggaacctct   30180
gtccctcttc tgcagtgggg gagcccatca ccgtccctaa gctggagcac ccgacccaga   30240
aagacatcga cctgtaccac accatgtaca tggaggccct ggtgaagctc tttgacaatc   30300
acaagaccaa attcggcctt ccagagactg aggtgctgga ggtgaactga cccagcccat   30360
gggtgccagc tcctggaagg aatgactgca aatccttttc taccaagttc tcaagtgcat   30420
tttgttctgt aaatttggaa gcgtcatggg tgtctgtggg ttatttaaaa gaaattataa   30480
tttgttaaac cattgcaatg ttagatcttt tttaagaagg gaagagtcag tattttaagc   30540
tcacttctag tgtgtcctgc ctaaggtggt ggctgacatt tataggcctt gatggtttct   30600
atccacccct tctagtgttc cccaaacaac agacacttgg ccctagttaa ttggggaagg   30660
gcagccctta gtgactcagc catttaatcc tcttcgctct agggattctc aagagacgga   30720
ggccacgttt aaaaacacct ccattcccac ccacaacacg tgactgctgg tcaggttttt   30780
cttacttagg ggaggatgag ggggcatagc tggttccgct tggggagagt ggtagataac   30840
atctggaatg cccggctcga gtgtcctctg ctccccacct actcctcttc tccaatctga   30900
gcctaccctg gcctcctgta cactgtgcta gggacagggc tgtcccacag gtgccatgtt   30960
```

-continued

```
gggttatctc gctgctgttg gctggtttta ctctggagat tggcatcgtg aacacagctc      31020
agcgtcattc tggagatgtt ctcccagcca cctgagctct cctgagccac accccaagtc      31080
tggtgtgagg agaggcctct gttcttcaca gaggtgcctg gcttcctgtg cagcacactg      31140
ggtccaggac aggaggccac ccccaaccaa gcctcacctg tgtgccttta tgaggcgtcg      31200
ggagaaagcc accctcctgt gtattctgct ttctccatga gattttgcca tgtcacactt      31260
ttgtatattc ctagactaat aaatggaaac aagaacagcc tatgcgttgt tgcttaatgc      31320
tgtactcaca ctgtctatcc cactgcacag ggcgcacttc gagggctctt tctggctggg      31380
taacaattgg cttcaaaatt tagtggctac agggatggag agatggctca atggttaaga      31440
acactgggtc ctgggggctg gggatttagc tcagtggtag agcgcttacc taggaagcgc      31500
aaggccctgg gttcggtccc cagctccgag aaaaaaaaaa aaaaaaaaaa aaaaagaac      31560 actgggtcct gtttaggacc ctggtttgat ttctgatatc ctcatggcag cttacaacta      31620
tccgtagttc cagtcctggg agatttgata tcctctgtgg gcacaaggca cataggtggt      31680
gcaacagaca tgtgcacgca acaatgccca tacacacaag cttttgtttt agaagaa        31737
```

```
<210> SEQ ID NO 112
<211> LENGTH: 264
<212> TYPE: DNA
<213> ORGANISM: Artificial Sequence
<220> FEATURE:
<223> OTHER INFORMATION: Oligomeric Compound

<400> SEQUENCE: 112
aaaagtagtg actttaagca tttgctctat tgtcctaagc taggtggttt cagggccctc       60
tgcttgctgg tgttggccag tgctaaaagc ttcccaagcc tgagcaagga agcgtcccac      120
tgttgatgcg ggtgacggca ggacgcctcc ctcactgact gttagcagag gccactgcag      180
ctcctagccc tgtattcctt tccacagggc ggctcactgc agggctgaga ggagcaagca      240
cacagcaagg agcacaagct gctg                                             264
```

```
<210> SEQ ID NO 113
<211> LENGTH: 20
<212> TYPE: DNA
<213> ORGANISM: Artificial Sequence
<220> FEATURE:
<223> OTHER INFORMATION: Oligomeric Compound

<400> SEQUENCE: 113
gctccttcca ctgatcctgc                                                   20
```

```
<210> SEQ ID NO 114
<211> LENGTH: 3247
<212> TYPE: DNA
<213> ORGANISM: H.sapiens

<400> SEQUENCE: 114
gggcgggcct cggggctaag agcgcgacgc ctagagcggc agacggcgca gtgggccgag       60
aaggaggcgc agcagccgcc ctggcccgtc atggagatgg aaaaggagtt cgagcagatc      120
gacaagtccg ggagctgggc ggccatttac caggatatcc gacatgaagc cagtgacttc      180
ccatgtagag tggccaagct tcctaagaac aaaaaccgaa ataggtacag agacgtcagt      240 cccttttgacc atagtcggat taaactacat caagaagata atgactatat caacgctagt      300
ttgataaaaa tggaagaagc ccaaaggagt tacattctta cccagggccc tttgcctaac      360
acatgcggtc acttttggga gatggtgtgg gagcagaaaa gcagggg tgt cgtcatgctc      420
```

```
aacagagtga tggagaaagg ttcgttaaaa tgcgcacaat actggccaca aaaagaagaa      480
aaagagatga tctttgaaga cacaaatttg aaattaacat tgatctctga agatatcaag      540
tcatattata cagtgcgaca gctagaattg aaaaaccttta aacccaagaa aactcgagag      600
atcttacatt tccactatac cacatggcct gactttggag tccctgaatc accagcctca      660
ttcttgaact ttcttttcaa agtccgagag tcagggtcac tcagcccgga gcacgggccc      720
gttgtggtgc actgcagtgc aggcatcggc aggtctggaa ccttctgtct ggctgatacc      780
tgcctcctgc tgatggacaa gaggaaagac ccttcttccg ttgatatcaa gaaagtgctg      840
ttagaaatga ggaagtttcg gatggggttg atccagacag ccgaccagct gcgcttctcc      900
tacctggctg tgatcgaagg tgccaaattc atcatggggg actcttccgt gcaggatcag      960
tggaaggagc tttcccacga ggacctggag cccccacccg agcatatccc cccacctccc     1020
cggccaccca aacgaatcct ggagccacac aatgggaaat gcaggagtt cttcccaaat      1080 caccagtggg tgaaggaaga gacccaggag gataaagact gccccatcaa ggaagaaaaa     1140
ggaagcccct aaatgccgc accctacggc atcgaaagca tgagtcaaga cactgaagtt      1200
agaagtcggg tcgtgggggg aagtcttcga ggtgcccagg ctgcctcccc agccaaaggg     1260
gagccgtcac tgcccgagaa ggacgaggac catgcactga gttactggaa gcccttcctg     1320
gtcaacatgt gcgtggctac ggtcctcacg gccggcgctt acctctgcta caggttcctg     1380
ttcaacagca acacatagcc tgaccctcct ccactccacc tccacccact gtccgcctct     1440
gcccgcagag cccacgcccg actagcaggc atgccgcggt aggtaagggc cgccggaccg     1500
cgtagagagc cgggcccccgg acggacgttg gttctgcact aaaacccatc ttccccggat     1560
gtgtgtctca cccctcatcc ttttactttt tgcccttcc acttgagta ccaaatccac       1620 aagccattt ttgaggagag tgaaagagag taccatgctg gcggcgcaga gggaaggggc      1680
ctacacccgt cttggggctc gccccaccca gggctccctc ctggagcatc ccaggcggcg     1740
cacgccaaca gcccccccct tgaatctgca gggagcaact ctccactcca tatttattta     1800
aacaattttt tccccaaagg catccatagt gcactagcat tttcttgaac caataatgta     1860
ttaaaatttt ttgatgtcag ccttgcatca agggctttat caaaaagtac aataataaat     1920
cctcaggtag tactgggaat ggaaggcttt gccatgggcc tgctgcgtca gaccagtact     1980
gggaaggagg acggttgtaa gcagttgtta tttagtgata ttgtgggtaa cgtgagaaga     2040
tagaacaatg ctataatata taatgaacac gtgggtattt aataagaaac atgatgtgag     2100
attactttgt cccgcttatt ctcctccctg ttatctgcta gatctagttc tcaatcactg     2160
ctcccccgtg tgtattagaa tgcatgtaag gtcttcttgt gtcctgatga aaaatatgtg     2220
cttgaaatga gaaactttga tctctgctta ctaatgtgcc ccatgtccaa gtccaacctg     2280
cctgtgcatg acctgatcat tacatggctg tggttcctaa gctgttgct gaagtcattg      2340 tcgctcagca atagggtgca gttttccagg aataggcatt tgctaattcc tggcatgaca     2400
ctctagtgac ttcctggtga ggcccagcct gtcctggtac agcagggtct tgctgtaact     2460
cagacattcc aagggtatgg gaagccatat tcacacctca cgctctggac atgatttagg     2520
gaagcaggga cacccccgc ccccccactt tgggatcagc ctccgccatt ccaagtcaac      2580
actcttcttg agcagaccgt gatttggaag agaggcacct gctggaaacc acacttcttg     2640
aaacagcctg ggtgacggtc ctttaggcag cctgccgccg tctctgtccc ggttcacctt     2700
gccgagagag gcgcgtctgc cccacctca aaccctgtgg ggcctgatgg tgctcacgac      2760
tcttcctgca aagggaactg aagacctcca cattaagtgg cttttttaaca tgaaaaacac     2820
```

```
ggcagctgta gctcccgagc tactctcttg ccagcatttt cacattttgc ctttctcgtg    2880
gtagaagcca gtacagagaa attctgtggt gggaacattc gaggtgtcac cctgcagagc    2940
tatggtgagg tgtggataag gcttaggtgc caggctgtaa gcattctgag ctggcttgtt    3000
gtttttaagt cctgtatatg tatgtagtag tttgggtgtg tatatatagt agcatttcaa    3060
aatggacgta ctggtttaac ctcctatcct tggagagcag ctggctctcc accttgttac    3120
acattatgtt agagaggtag cgagctgctc tgctatatgc cttaagccaa tatttactca    3180
tcaggtcatt atttttaca atggccatgg aataaaccat ttttacaaaa ataaaaacaa    3240
aaaaagc                                                             3247

<210> SEQ ID NO 115
<211> LENGTH: 20
<212> TYPE: DNA
<213> ORGANISM: Artificial Sequence
<220> FEATURE:
<223> OTHER INFORMATION: Oligomeric compound

<400> SEQUENCE: 115
tcccatttca ggagacctgg                                               20

<210> SEQ ID NO 116
<211> LENGTH: 20
<212> TYPE: DNA
<213> ORGANISM: Artificial Sequence
<220> FEATURE:
<223> OTHER INFORMATION: Oligomeric compound

<400> SEQUENCE: 116
gcactctgga cccaaaccag                                               20
```